US007932230B2

(12) United States Patent
McDaniel

(10) Patent No.: US 7,932,230 B2
(45) Date of Patent: *Apr. 26, 2011

(54) ANTIFUNGAL PAINTS AND COATINGS

(75) Inventor: C. Steven McDaniel, Austin, TX (US)

(73) Assignee: Reactive Surfaces, Ltd., LLP, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/543,199

(22) Filed: Aug. 18, 2009

(65) Prior Publication Data
US 2009/0312234 A1 Dec. 17, 2009

Related U.S. Application Data

(62) Division of application No. 10/884,355, filed on Jul. 2, 2004.

(60) Provisional application No. 60/485,234, filed on Jul. 3, 2003.

(51) Int. Cl.
A61K 38/00 (2006.01)
A61K 38/10 (2006.01)
A61K 31/74 (2006.01)
C07K 7/00 (2006.01)
C07K 17/00 (2006.01)

(52) U.S. Cl. ...... 514/21.4; 514/21.5; 530/326; 530/327; 424/78.09; 424/404

(58) Field of Classification Search .......... None
See application file for complete search history.

(56) References Cited

U.S. PATENT DOCUMENTS

| 4,342,751 | A | | 8/1982 | Moore et al. |
| 4,935,351 | A | | 6/1990 | Yamane et al. |
| 5,069,717 | A | | 12/1991 | Sherba et al. |
| 5,482,996 | A | | 1/1996 | Russell et al. |
| 5,602,097 | A | | 2/1997 | Edwards |
| 5,646,014 | A | | 7/1997 | Hara |
| 5,879,440 | A | * | 3/1999 | Sau ............ 106/162.1 |
| 5,882,731 | A | | 3/1999 | Owens |
| 5,885,782 | A | | 3/1999 | Edwards |
| 5,919,689 | A | | 7/1999 | Selvig et al. |
| 5,998,200 | A | | 12/1999 | Bonaventura et al. |
| 6,020,312 | A | | 2/2000 | Edwards |
| 6,054,504 | A | | 4/2000 | Dalla Riva Toma |
| 6,294,183 | B1 | | 9/2001 | Ito et al. |
| 6,858,581 | B2 | * | 2/2005 | Kuhner et al. ............ 514/2 |
| 7,041,285 | B2 | | 5/2006 | Polsenski et al. |
| 7,125,842 | B2 | | 10/2006 | Kawabe et al. |
| 7,238,669 | B2 | | 7/2007 | Bishop-Hurley et al. |
| 7,335,400 | B2 | | 2/2008 | Russell et al. |
| 2002/0010228 | A1 | | 1/2002 | Simendinger, III |
| 2002/0010229 | A1 | | 1/2002 | Medoff et al. |
| 2002/0013385 | A1 | | 1/2002 | Simendinger, III |
| 2002/0018764 | A1 | | 2/2002 | Yamamori et al. |
| 2002/0035239 | A1 | | 3/2002 | Andersen et al. |
| 2002/0106361 | A1 | | 8/2002 | Poulsen et al. |
| 2002/0132540 | A1 | | 9/2002 | Soerens et al. |
| 2003/0166237 | A1 | | 9/2003 | Allermann et al. |
| 2003/0194445 | A1 | | 10/2003 | Kuhner et al. |
| 2004/0109853 | A1 | | 6/2004 | McDaniel |
| 2004/0175407 | A1 | | 8/2004 | McDaniel |
| 2004/0248783 | A1 | | 12/2004 | Kawabe et al. |
| 2005/0147579 | A1 | | 7/2005 | Schneider et al. |

FOREIGN PATENT DOCUMENTS

| CN | 1031387 | | 3/1989 |
| CN | 2249311 | A | 5/1992 |
| EP | 1174439 | | 1/2002 |
| JP | 53119872 | A * | 10/1978 |
| JP | 58198580 | | 11/1983 |
| JP | 3239766 | | 10/1991 |
| JP | 5247378 | | 9/1993 |
| WO | 94/01459 | | 1/1994 |
| WO | 95/08341 | | 3/1995 |
| WO | 01/72911 | | 10/2001 |
| WO | 02/064183 | | 8/2002 |
| WO | 2004/055044 | | 7/2004 |

OTHER PUBLICATIONS

Ehret-Sabatier, L., et al. 1996 The Journal of Biological Chemistry 271(47): 29537-29544.*
Wang et al., "Ginkbilobin, a Novel Antifungal Protein from *Ginkgo biloba* Seeds with Sequence Similarity to Embryo-Abundant Protein," Biochem. & Biophys. Res. Comm., vol. 279, 2000, pp. 407-411.
Wang et al., "Novel Antifungal Peptides from Ceylon Spinach Seeds," Biochem. & Biophys. Res. Comm., vol. 288, 2001, pp. 765-770.
Wilde et al., "Purification and Characterization of Human Neutrophil Peptide 4, a Novel Member of the Defensin Family," The Journal of Biological Chemistry, vol. 264, No. 19, Jul. 1989, pp. 11200-11203.
Yi et al., "Solution structure of an antimicrobial peptide buforin II," FEBS Letters, vol. 398, 1996, pp. 87-90.
Yin et al., "Physical parameters of hydroxyapatite adorption and effect on candidacidal activity of histatins," Archives of Oral Biology, vol. 48, 2003, pp. 361-368.
Zhang et al., "NMR Studies of Defensin Antimicrobial Peptides: 1. Resonance Assignment and Secondary Structure Determined of Rabbit NP-2 and Human HNP-1," Biochemistry, vol. 31, 1992, pp. 11348-11356.
Zhao et al., "Identification of a new member of the protegrin family by cDNA cloning," FEBS Letters, vol. 346, 1994, pp. 285-288.
Zhao et al., "The structure of porcine protegrin genes," FEBS Letters, vol. 368, 1995, pp. 197-202.
Zhu et al., "Isolation and Mode of Action of Rabbit Corticostatic (Antiadrenocorticotropin) Peptides," Endocrinology, vol. 130, No. 3, 1992, pp. 1413-1423.
Zimmermann et al., "Solution Structure of Bovine Neutrophil β-Defensin-12: The Peptide Fold of the β-Defensin is Identical to that of the Classical Defensins," Biochemistry, vol. 34, 1995, pp. 13663-13671.

(Continued)

Primary Examiner — Maryam Monshipouri
Assistant Examiner — Marsha M Tsay
(74) Attorney, Agent, or Firm — Rissman Hendricks & Oliverio, LLP

(57) ABSTRACT

Antifungal and antibacterial peptides, polypeptides and proteins as antifungal additives for paint and other coatings are disclosed, along with antifungal compositions, and coated surfaces with antifungal properties. Methods of using the coatings for treating and/or inhibiting growth of mold, mildew and other fungi and bacteria on objects such as building materials that are susceptible to such infestation are also disclosed.

2 Claims, No Drawings

OTHER PUBLICATIONS

Cutuli et al., "Antimicrobial effects of α-MSH peptides," Journal of Leukocyte Biology, vol. 67, Feb. 2000, pp. 233-239.

Destoumieux et al., "Penaeidins, a family of antimicrobial peptides from penaeid shrimp (Crustacea, Decapoda)," CMLS, vol. 57, 2000, pp. 1260-1271.

Fiedler et al., "Nikkomycins: Microbial Inhibitors of Chitin Synthase," J. Chem. Tech. Biotechnol., vol. 32, 1982, pp. 271-280.

Goraya et al., "Peptides with antimicrobial activity from four different families isolated from the skins of the North American frogs *Rana luteiventris, Rana berlandieri and Rana pipiens*," Eur. J. Biochem., vol. 267, 2000, pp. 894-900.

Guichard et al., "Antigenic mimicry of natural L-peptides with retro-inverso-peptidomimetics," Proc. Natl. Acad. Sci. USA, vol. 91, Oct. 1994, pp. 9765-9769.

Iijima et al., "A novel antimicrobial peptide from the sea hare *Dolabella auricularia*," Developmental & Comparative Immunology, vol. 27, 2003, pp. 305-311.

Koo et al., "Two hevein homologs isolated from the seed of *Pharbitis nil L*. exhibit potent antifungal activity,". Biochimica et Biophysica Acta, vol. 1382, 1998, pp. 80-90.

Jones et al- "Paneth Cells of the Human Small Intestine Express an Antimicrobial Peptide Gene," The Journal of Biological Chemistry, vol. 267, No. 32, Nov. 1992, pp. 23216-23225.

Lee et al., "Purification and cDNA Cloning of an Antifungal Protein from the Hemolymph of *Holotrichia diomphalia* Larvae," Biol. Pharm. Bull., vol. 18, No. 8, 1995, pp. 1049-1052.

Mandard et al., "Solution structure of thanatin, a potent bactericidal and fungicidal insect peptide, determined from proton two-dimensional nuclear magnetic resonance data," Eur. J. Biochem., vol. 256, 1998, pp. 404-410.

Mandard et al., "Androctonin, a Novel Antimicrobial Peptide from Scorpion *Androctonus australis*: Solution Structure and Molecular Dynamics Simulations in the Presence of a Lipid Monolayer," Journal of Biomolecular Structure & Dynamics, vol. 17, No. 2, 1999, pp. 367-380.

Nagaoka et al., "Cloning and characterization of the guinea pig neutrophil cationic peptide-1 and -2 genes," J. DNA Sequencing & Mapping, vol. 4, 1993, pp. 123-128.

Qu et al., "Insect Immunity: Isolation and Structure of Cecropins B and D from Pupae of the Chinese Oak Silk Moth, *Antheraea pernyi*," Eur. J. Biochem., vol. 127, 1982, pp. 219-224.

Soedjanaatmadja et al., "Demonstration by mass spectrometry that pseudo-hevein and hevein have ragged C-terminal sequences," Biochimica et Biophysica Acta, vol. 1209, 1994, pp. 144-148.

Theil et al., "Purification and Spectral Characterization of Seminalplasmin, an Antimicrobial Protein from Bull Semen," Hoppe-Seyler's Z. Physiol. Chem. Bd., vol. 364, Aug. 1983, pp. 1003-1009.

Xu et al., "Primary Structure and Anticandidal Actificy of the Major Histatin from Parotid Secretion of the Subhuman Primate, *Macaca fascicularis*," J. Dent. Res., vol. 69, No. 11, Nov. 1990, pp. 1717-1723.

Yount et al., "Rat Neutrophil Defensins: Precursor Structures and Expression During Neutrophilic Myelopoiesis," The Journal of Immunology, vol. 155, 1995, pp. 4476-4484.

Zasloff et al., "Magainins, a class of antimicrobial peptides from *Xenopus* skin: Isolation, characterization of two active forms, and partial cDNA sequence of a precursor," Proc. Natl. Acad. Sci. USA, vol. 84, Aug. 1987, pp. 5449-5453.

Zhu et al., "Isolation and structure of corticostatin peptides from rabbit fetal and adult lung," Proc. Natl. Acad. Sci. USA, vol. 85, Jan. 1988, pp. 592-596.

Grau et al., "A Biophysical Study of the Interaction of the Lipopeptide Antibiotic Iturin A with Aqueous Phospholipid Bilayers," Archives of Biochemistry & Biophysics, vol. 377, No. 2, May 2000, pp. 315-323.

Gillatt, "Microbiological Protection of Waterborne Paint Formulations," Waterborne Coatings and Additives, © The Royal Society of Chemistry 1995, pp. 202-216.

Brunt, "A Silver Lining for Paints and Coatings—A Revolutionary Preservative System," Waterborne Coatings and Additives, © The Royal Society of Chemistry 1995, pp. 243-246.

Paints, Coatings and Solvents, Second Completely Revised Edition, Edited by Stoye and Freitag, © Wiley-VCH 1998, pp. 6, 12-19, 127, 165, 288-290.

International Search Report, PCT/US2004/021711, mailed Feb. 23, 2005.

Plueddemann, Silane Coupling Agents, © 1982 Plenum Press, pp. 224-229.

Cole et al., "Cutting Edge: IFN-Inducible ELR-CXC Chemokiness Display Defensin-Like Antimicrobial Activity," The Journal of Immunology, 2001, pp. 623-627.

Dathe et al., "Optimization of the antimicrobial activity of magainin peptides by modification of charge," FEBS Letters, vol. 501, 2001, pp. 146-150.

Abstract only, JP11124521, published May 1999.

Eisenberg et al., Structure Summary Printout for 2mlt, deposited to RCSB Protein Data Bank Oct. 1990.

Bulet et al., Sequence, Function, Subunit, Subcellular Location, Tissue Induction, Mass Spectrometry, and Amidation, submitted to Swiss-Prot. Data Bank Jul. 2002.

Michalowski et al., Sequence from Nucleic Acid, submitted to the EMBL/GenBank/DDGB Databases Jun. 1998.

ASTM D 964, Standard Specification for Metallic Copper Powder for Use in Antifouling Paints, published May 2003, 1 page.

ASTM D 2574, Standard Test Method for Resistance of Emulsion Paints in the Container to Attack by Microorganisms, published Sep. 1997, 4 pages.

ASTM D 3273, Standard Test Method for Resistance to Growth of Mold on the Surface of Interior Coatings in an Environmental Chamber, published Oct. 1994, 3 pages.

ASTM D 3274, Standard Test Method for Evaluating Degree of Surface Disfigurement of Paint Films by Microbial (Fungal or Algal) Growth or Soil and Dirt Accumulation, published Jun. 1995, 4 pages.

ASTM D 3456, Standard Practice for Determining by Exterior Exposure Tests the Susceptibility of Paint Films to Microbiological Attack, published May 1986, 4 pages.

ASTM D 3623, Standard Test Method for Testing Antifouling Panels in Shallow Submergence, published Jun. 2004, 8 pages.

ASTMD 4610, Standard Guide for Determining the Presence of and Removing Microbial (Fungal or Algal) Growth on Paint and Related Coatings, published Jun. 2004, 2 pages.

ASTM D 4938, Standard Test Method for Erosion Testing of Antifouling Paints Using High Velocity Water, published Jun. 1989, 4 pages.

ASTM D 4939, Standard Test Method for Subjecting Marine Antifouling Coating to Biofouling and Fluid Shear Forces in Natural Seawater, published May 2003, 5 pagse.

ASTM D 5108, Standard Test Method for Organotin Release Rates of Antifouling Coating Systems in Sea Water, published Feb. 1991, 6 pages.

ASTM D 5479, Standard Practice for Testing Biofouling Resistance of Marine Coatings Partially Immersed, published May 1994, 2 pages.

ASTM D 5589, Standard Practice Test Method for Determining the Resistance of Paint Films and Related Coatings to Algal Defacement, published Sep. 1997, 4 pages.

ASTM D 5590, Standard Test Method for Determining the Resistance of Paint Films and Related Coatings to Fungal Defacement by Accelerated Four-Week Agar Plate Assay, published Oct. 1994, 4 pages.

ASTM D 5618, Standard Test Method for Measurement of Barnacle Adhesion Strength in Shear, published Dec. 1994, 2 pages.

ASTMD 912, Standard Specification for Cuprous Oxide for Use in Antifouling Paints, Dec. 1981, 1 page.

Bell et al., "Reactive Coatings Literature Review," prepared for the U.S. Army Research Office, Dec. 2001, 41 pages.

"Green Marine Paint," Chemical Week, Apr. 2001, p. 33.

Flick, Handbook of Paint Raw Materials, 2nd Ed., published by Noyes Publications, Aug. 1989, pp. 263-285.

Wicks et al., Organic Coatings, Science and Technology, vol. 1: Film Formation, Components, and Appearance, published by Wiley-Interscience, Oct. 1992, pp. 318-320.

Wicks et al., Organic Coatings, Science and Technology, vol. 2: Applications, Properties, and Performance, published by Wiley-Interscience, Nov. 1993, pp. 145, 309, 319-323, 340-341.
"PPG Installs Cleaning System," PCI Magazine, Jul. 2002, pp. 68-70.
"Copper-8-Quinolinolate Chemistry for Specialty Wood Preservative," PCI Magazine, Jun. 2002, 3 pages.
"Emulsion Polymer Technologies," Paint Research Association, vol. 13, No. 12, Apr. 2002, 24 pages.
"The PCI 50 & Global Top 10," PCI Magazine, Jun. 2002, 34 pages.
Winkowski, "Controlling Microbial Contamination," PCI Magazine, Jun. 2002, 6 pages.
Paint and Surface Coatings, Theory and Practice, 2nd Ed., © 1999 Woodhead Publishing Ltd., pp. 2, 3, 10, 24, 51, 162, 193, 194, 371-383, 397, 448, 494-497, 533, 541-547, 700.
Drevon et al., "High-Activity Enzyme-Polyurethane Coatings," Biotechnology & Bioengineering, vol. 79, No. 7, 2002, pp. 785-794.
Handbook of Coatings Additives, © 1987 Marcel Dekker, Inc., pp. 43-63 and 177-224.
Almeida et al., "Solution Structure of *Pisum sativum* Defensin 1 by High Resolution NMR: Plant Defensins, Identical Backbone with Different Mechanisms of Action," J. Mol. Biol., vol. 315, 2002, pp. 749-757.
Bobek et al., "MUC7 20-Mer: Investigation of Antimicrobial Activity, Secondary Structure, and Possible Mechanism of Antifungal Action," Antimicrobial Agents & Chemotherapy, vol. 47, No. 2, Feb. 2003, pp. 643-652.
Cammue et al., "Isolation and Characterization of a Novel Class of Plant Antimicrobial Peptides from *Mirabilis jalapa* L. Seeds," The Journal of Biological Chemistry, vol. 267, No. 4, Feb. 1992, pp. 2228-2233.
Duvick et al., "Purification and Characterization of a Novel Antimicrobial Peptide from Maize (*Zea mays* L.) Kernels," The Journal of Biological Chemistry, vol. 267, No. 26, Sep. 1992, pp. 18814-18820.
Fernandes et al., "Anti-microbial properties of histone H2A from skin secretions of rainbow trout, *Oncorhynchus mykiss*," Biochem. J., vol. 368, 2002, pp. 611-620.
Fujitani et al., "Structure of the Antimicrobial Peptide Tachystatin A," The Journal of Biological Chemistry, vol. 277, No. 26, Jun. 2002, pp. 23651-23657.
Gao et al., "Solution Structure of PAFP-S: A New Knottin-Type Antifungal Peptide from the Seeds of *Phytolacca americana*," Biochemistry, vol. 40, 2001, pp. 10973-10978.
Gesell et al., "Two-dimensional 1H NMR experiments show that the 23-residue magainin antibiotic peptide is an α-helix in dodecylphosphocholine micelles, sodium dodecylsulfate micelles, and trifluoroethanol/water solution," Journal of Biololecular NMR, vol. 9, 1997, pp. 127-135.
Halverson et al., "Purification and characterization of antimicrobial peptides from the skin of the North American green frog *Rana clamitans*," Peptides, vol. 21, 2000, pp. 469-476.
Hara et al., "Effects of Peptide Dimerization on Pore Formation: Antiparallel Disulfide-Dimerized Magainin 2 Analogue," Biopolymers, vol. 58, 2001, pp. 437-446.
Hill et al., "Crystal Structure of Defensin HNP-3, an Amphiphilic Dimer: Mechanisms of Membrane Permeabilization," Science, New Series, vol. 251, No. 5000, Mar. 1991, pp. 1481-1485.
Hunter et al., "The Solution Structure of Human Hepcidin, a Peptide Hormone with Antimicrobial Activity that is Involved in Iron Uptake and Hereditary Hemochromatosis," The Journal of Biological Chemistry, vol. 277, No. 40, Oct. 2002, pp. 37597-37603.
Hwang et al., "Three-Dimensional Solution Structure of Lactoferricin B, an Antimicrobial Peptide Derived from Bovine Lactoferrin," Biochemistry, vol. 37, 1998, pp. 4288-4298.
Jones et al., "Defensin-6 mRNA in human Paneth cells: implications for antimicrobial peptides in host defense of the human bowel," FEBS Lett., vol. 315, No. 2, Jan. 1993, pp. 187-192.
Kokryakov et al., "Protegrins: leukocyte antimicrobial peptides that combine features of corticostatic defensins and tachyplesins," FEBS Lett., vol. 327, No. 2, Jul. 1993, pp. 231-236.
Lamberty et al., "Solution Structures of the Antifungal Heliomicin and a Selected Variant with both Antibacterial and Antifungal Activities," Biochemistry, vol. 40, 2001, pp. 11995-12003.

Lamberty et al., "Insect Immunity, Constitutive Expression of a Cysteine-Rich Antifungal and a Linear Antibacterial Peptide in a Termite Insect," The Journal of Biological Chemistry, vol. 276, No. 6, Feb. 2001, pp. 4085-4092.
Lee et al., "Antibiotic Activity of Reversed Peptides of α-Helical Antimicrobial Peptide, P18," Protein & Peptide Letters, vol. 9, No. 5, 2002, pp. 395-402.
Mak et al., "Isolation, Antimicrobial Activities, and Primary Structures of Hamster Neutrophil Defensins," Infection & Immunity, Nov. 1996, pp. 4444-4449.
Mandard et al., "The solution structure of gomesin, an antimicrobial cysteine-rich peptide from the spider," Eur. J. Biochem., vol. 269, 2002, pp. 1190-1198.
Martins et al., "1H NMR Study of the Solution Structure of Ac-AMP2, a Sugar Binding Antimicrobial Protein Isolated from *Amaranthus caudatus*," J. Mol. Biol., vol. 258, 1996, pp. 322-333.
Moerman et al., "Antibacterial and antifungal properties of α-helical, cationic peptides in the venom of scorpions from southern Africa," Eur. J. Biochem., vol. 269, 2002, pp. 4799-4810.
Moore et al., "Antimicrobial Peptides in the Stomach of *Xenopus laevis*," The Journal of Biological Chemistry, vol. 266, No. 29, Oct. 1991, pp. 19851-19857.
Mor et al., "Isolation and structure of novel defensive peptides from frog skin," Eur. J. Biochem. vol. 219, 1994, pp. 145-154.
Mor et al., "Skip peptide tyrosine-tyrosine, a member of the pancreatic polypeptide family: Isolation, structure, synthesis, and endrocrine activity," Proc. Natl. Acad. Sci. USA, vol. 91, Oct. 1994, pp. 10295-10299.
Nagaoka et al., "Characterization of cDNA clones encoding guinea pig neutrophil cationic peptides," FEBS, vol. 280, No. 2, Mar. 1991, pp. 287-291.
Olson III et al., "Pseudin-2: An Antimicrobial Peptide with Low Hemolytic Activity from the Skin of the Paradixical Frog," Biochem. & Biophys. Res. Comm., vol. 288, 2001, pp. 1001-1005.
Oppenheim et al., "Histatins, a Novel Family of Histidine-rich Proteins in Human Parotid Secretion," The Journal of Biological Chemistry, vol. 263, No. 16, Jun. 1988, pp. 7472-7477.
Orivel et al., "Ponericins, New Antibacterial and Insecticidal Peptides from the Venom of the Ant *Pachycondyla goeldii*," The Journal of Biological Chemistry, vol. 276, No. 21, May 2001, pp. 17823-17829.
Park et al., "Antimicrobial Peptides from the Skin of a Korean Frog, Rana Rugosa," Biochem. & Biophys. Res. Comm., vol. 205, No. 1, Nov. 1994, pp. 948-954.
Park et al., "A Novel Antimicrobial Peptide from *Bufo bufo gargarizans*," Biochem. & Biophys. Res. Comm., vol. 218, 1996, pp. 408-413.
Park et al., "Structural study of novel antimicrobial peptides, nigrocins, isolated from *Rana nigromaculata*," FEBS Letters, vol. 507, 2001, pp. 95-100.
Park et al., "A novel antimicrobial peptide from the loach, *Misgurnus anguillicaudatus*," FEBS Letters, vol. 411, 1997, pp. 173-178.
Raj et al., "Structure of Human Salivary Histatin 5 in Aqueous and Nonaqueous Solutions," Biopolymers, vol. 45, 1998, pp. 51-67.
Tailor et al., "A Novel Family of Small Cysteine-rich Antimicrobial Peptides from Seed of Impatiens balsamina is Derives from a Single Precursor Protein," The Journal of Biological Chemistry, vol. 272, No. 39, Sep. 1997, pp. 24480-24487.
Rebuffat et al., "Tricholongins BI and BII, 19-residue peptaibols from *Trichoderma longibrachiatum*," Eur. J. Biochem., vol. 201, 1991, pp. 661-674.
Robinette et al., "Antimicrobial activity in the skin of the channel catfish Ictalurus punctatus: characterization of broad-spectrum histone-like antimicrobial proteins," CMLS, vol. 54, 1998, pp. 467-475.
Rozek et al., "Structure of the Bovine Antimicrobial Peptide Indolicidin Bound to Dodecylphosphocholine and Sodium Dodecyl Sulfate Micelles," Biochemistry, vol. 39, 2000, pp. 15765-15774.
Rozek et al., "The antibiotic and anticancer active aurein peptides from the Australian Bell Frogs *Litoria aurea* and *Litoria raniformis*," Eur. J. Biochem. vol. 267, 2000, pp. 5330-5341.

Ruissen et al., "Histatin 5 and derivatives: Their localization and effects on the ultra-structural level," Peptides, vol. 23, 2002, pp. 1391-1399.

Schibli et al., "Structure of the Antimicrobial Peptide Tritrpticin Bound to Micelles: A Distinct Membrane-Bound Peptide Fold," Biochemistry, vol. 38, 1999, pp. 16749-16755.

Schonwetter et al., "Epithelial antibiotics induced at sites of inflammation," Science, vol. 267, No. 5204, Mar. 1995, pp. 1645-1648.

Scocchi et al., "Structural organization of the bovine cathelicidin gene family and identification of a novel member," FEBS Letters, vol. 417, 1997, pp. 311-315.

Selsted et al., "Primary Structures of MCP-1 and MCP-2, Natural Peptide Antibiotics of Rabbit Lung Macrophages," The Journal of Biological Chemistry, vol. 258, No. 23, Dec. 1983, pp. 14485-14489.

Skerlavaj et al., Biological Characterization of Two Novel Cathelicidin-derived Peptides and Identification of Structural Requirements for Their Antimicrobial and Cell Lytic Activities, The Journal of Biological Chemistry, vol. 271, No. 45, Nov. 1996, pp. 28375-28381.

Tang et al., "Isolation, Characterication, cDNA Cloning, and Antimicrobial Properties of Two Distinct Subfamilies of α-Defensins from Rhesus Macaque Leukocytes," Infection & Immunity, vol. 67, No. 11, Nov. 1999, pp. 6139-6144.

Terras et al., "A new family of basic cysteine-rich plant antifungal proteins from *Brassicaceae species*," FEBS, vol. 316, No. 3, Feb. 1993, pp. 233-240.

Tinoco et al., "NMR Structure of PW2 Bound to SDS Micelles," The Journal of Biological Chemistry, vol. 277, No. 39, Sep. 2002, pp. 36351-36356.

Ueta et al, "A novel bovine lactoferrin peptide, FKCRRWQWRM, suppresses *Candida* cell growth and activates neutrophils," J. Peptide Res., vol. 57, 2001, pp. 240-249.

Vogel et al., "Towards a structure-function analysis of bovine lactoferricin and related tryptophan- and arginine-containing peptides," Biochem. Cell Biol., vol. 80, 2002, pp. 49-63.

Broun, et al., "Catalytic Plasticity of Fatty Acid Modification Enzymes Underlying Chemical Diversity of Plant Lipids", Science, vol. 282, p. 1315 (1998).

Devos et al., "Practical Limits of Function Prediction", Proteins: Structure, Function, and Genetics, vol. 41, pp. 98-107 (2000).

Kisselev, "Polypeptide Release Factors in Prokaryotes and Eukaryotes: Same Function, Different Structure", Structure, vol. 10 (2002).

McDaniel et al., "Enzyme-based additives for paints and coatings", Progress in Organic Coating, vol. 55 (2006), pp. 182-188.

Seffernick et al., "Melamine Deaminase and Atrazine Clorohydrolase: 98 Percent Identical but Functionally Differen", Journal of Bacteriology, vol. 183 (2001), pp. 2405-2410.

Whisstock et al., "Prediction of protein function form protein sequence and structure", Quarterly Reviews of Biophysics vol. 36, No. 3 (2003), pp. 307-340.

Witkowski et al., "Conversion of a beta-Ketoacyl Systhase to a Malonyl Decarboxylase by Replacement of the Active-Site Cysteine with Glutamine", Biochemistry vol. 38 (1999), pp. 11643-11650.

\* cited by examiner

ID

SEQUENCE LISTING

```
<160> NUMBER OF SEQ ID NOS: 203

<210> SEQ ID NO 1
<211> LENGTH: 6
<212> TYPE: PRT
```

```
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 1

Xaa Xaa Xaa Xaa Arg Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 2

Xaa Xaa Xaa Xaa Phe His
1               5

<210> SEQ ID NO 3
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 3

Xaa Xaa Xaa Xaa Lys Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 4

Xaa Xaa Xaa Xaa Gln Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 5

Xaa Xaa Xaa Xaa Arg Met
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 6

Xaa Xaa Xaa Xaa His Met
1               5

<210> SEQ ID NO 7
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 7

Xaa Xaa Xaa Xaa Lys Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 8

Xaa Xaa Xaa Xaa Arg Leu
1               5

<210> SEQ ID NO 9
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 9

Xaa Xaa Xaa Leu Arg Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid
```

-continued

```
<400> SEQUENCE: 10

Xaa Xaa Xaa Ile Arg Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 11

Xaa Xaa Xaa Phe Arg Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 12

Xaa Xaa Xaa Trp Arg Phe
1               5

<210> SEQ ID NO 13
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 13

Xaa Xaa Xaa Met Arg Phe
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 14

Xaa Xaa Lys Leu Arg Phe
1               5

<210> SEQ ID NO 15
<211> LENGTH: 6
<212> TYPE: PRT
<213> ORGANISM: Artificial Sequence
<220> FEATURE:
```

```
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 15

Xaa Xaa Arg Leu Arg Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 16

Xaa Xaa His Leu Arg Phe
1               5

<210> SEQ ID NO 17
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 17

Xaa Xaa Thr Leu Arg Phe
1               5

<210> SEQ ID NO 18
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 18

Xaa Xaa Phe Leu Arg Phe
1               5

<210> SEQ ID NO 19
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 19

Xaa Xaa Ser Leu Arg Phe
1               5
```

```
<210> SEQ ID NO 20
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 20

Xaa Xaa Ile Leu Arg Phe
1               5

<210> SEQ ID NO 21
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 21

Xaa Xaa Leu Leu Arg Phe
1               5

<210> SEQ ID NO 22
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 22

Xaa Xaa Ala Leu Arg Phe
1               5

<210> SEQ ID NO 23
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 23

Xaa Xaa Trp Leu Arg Phe
1               5

<210> SEQ ID NO 24
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 24
```

```
Xaa Xaa Met Leu Arg Phe
1               5

<210> SEQ ID NO 25
<211> LENGTH: 3
<212> TYPE: PRT
<213> ORGANISM: Artificial Sequence
<220> FEATURE:
<223> OTHER INFORMATION: Synthesized

<400> SEQUENCE: 25

Phe Arg Phe
1

<210> SEQ ID NO 26
<211> LENGTH: 3
<212> TYPE: PRT
<213> ORGANISM: Artificial Sequence
<220> FEATURE:
<223> OTHER INFORMATION: Synthesized

<400> SEQUENCE: 26

Leu Arg Phe
1

<210> SEQ ID NO 27
<211> LENGTH: 3
<212> TYPE: PRT
<213> ORGANISM: Artificial Sequence
<220> FEATURE:
<223> OTHER INFORMATION: Synthesized

<400> SEQUENCE: 27

Trp Arg Phe
1

<210> SEQ ID NO 28
<211> LENGTH: 3
<212> TYPE: PRT
<213> ORGANISM: Artificial Sequence
<220> FEATURE:
<223> OTHER INFORMATION: Synthesized

<400> SEQUENCE: 28

His Arg Phe
1

<210> SEQ ID NO 29
<211> LENGTH: 4
<212> TYPE: PRT
<213> ORGANISM: Artificial Sequence
<220> FEATURE:
<223> OTHER INFORMATION: Synthesized

<400> SEQUENCE: 29

Phe Leu Arg Phe
1

<210> SEQ ID NO 30
<211> LENGTH: 4
<212> TYPE: PRT
<213> ORGANISM: Artificial Sequence
<220> FEATURE:
<223> OTHER INFORMATION: Synthesized

<400> SEQUENCE: 30

Trp Leu Arg Phe
```

```
<210> SEQ ID NO 31
<211> LENGTH: 5
<212> TYPE: PRT
<213> ORGANISM: Artificial Sequence
<220> FEATURE:
<223> OTHER INFORMATION: Synthesized

<400> SEQUENCE: 31

Phe His Leu Arg Phe
1               5

<210> SEQ ID NO 32
<211> LENGTH: 6
<212> TYPE: PRT
<213> ORGANISM: Artificial Sequence
<220> FEATURE:
<223> OTHER INFORMATION: Synthesized

<400> SEQUENCE: 32

Phe Phe Lys Leu Arg Phe
1               5

<210> SEQ ID NO 33
<211> LENGTH: 6
<212> TYPE: PRT
<213> ORGANISM: Artificial Sequence
<220> FEATURE:
<223> OTHER INFORMATION: Synthesized

<400> SEQUENCE: 33

Val Phe Lys Leu Arg Phe
1               5

<210> SEQ ID NO 34
<211> LENGTH: 6
<212> TYPE: PRT
<213> ORGANISM: Artificial Sequence
<220> FEATURE:
<223> OTHER INFORMATION: Synthesized

<400> SEQUENCE: 34

His Phe Lys Leu Arg Phe
1               5

<210> SEQ ID NO 35
<211> LENGTH: 6
<212> TYPE: PRT
<213> ORGANISM: Artificial Sequence
<220> FEATURE:
<223> OTHER INFORMATION: Synthesized

<400> SEQUENCE: 35

Ile Phe Lys Leu Arg Phe
1               5

<210> SEQ ID NO 36
<211> LENGTH: 6
<212> TYPE: PRT
<213> ORGANISM: Artificial Sequence
<220> FEATURE:
<223> OTHER INFORMATION: Synthesized

<400> SEQUENCE: 36

Lys Arg Lys Leu Arg Phe
1               5
```

```
<210> SEQ ID NO 37
<211> LENGTH: 6
<212> TYPE: PRT
<213> ORGANISM: Artificial Sequence
<220> FEATURE:
<223> OTHER INFORMATION: Synthesized

<400> SEQUENCE: 37

Leu Phe Lys Leu Arg Phe
1               5

<210> SEQ ID NO 38
<211> LENGTH: 6
<212> TYPE: PRT
<213> ORGANISM: Artificial Sequence
<220> FEATURE:
<223> OTHER INFORMATION: Synthesized

<400> SEQUENCE: 38

Tyr Phe Lys Leu Arg Phe
1               5

<210> SEQ ID NO 39
<211> LENGTH: 7
<212> TYPE: PRT
<213> ORGANISM: Artificial Sequence
<220> FEATURE:
<223> OTHER INFORMATION: Synthesized

<400> SEQUENCE: 39

Phe His Phe Lys Leu Arg Phe
1               5

<210> SEQ ID NO 40
<211> LENGTH: 7
<212> TYPE: PRT
<213> ORGANISM: Artificial Sequence
<220> FEATURE:
<223> OTHER INFORMATION: Synthesized

<400> SEQUENCE: 40

Ile His Phe Lys Leu Arg Phe
1               5

<210> SEQ ID NO 41
<211> LENGTH: 6
<212> TYPE: PRT
<213> ORGANISM: Artificial Sequence
<220> FEATURE:
<223> OTHER INFORMATION: Synthesized

<400> SEQUENCE: 41

Phe Arg Leu Lys Phe His
1               5

<210> SEQ ID NO 42
<211> LENGTH: 6
<212> TYPE: PRT
<213> ORGANISM: Artificial Sequence
<220> FEATURE:
<223> OTHER INFORMATION: Synthesized

<400> SEQUENCE: 42

Arg Phe Lys Leu Arg Phe
1               5

<210> SEQ ID NO 43
```

```
<211> LENGTH: 6
<212> TYPE: PRT
<213> ORGANISM: Artificial Sequence
<220> FEATURE:
<223> OTHER INFORMATION: Synthesized

<400> SEQUENCE: 43

Ser Phe Lys Leu Arg Phe
1               5

<210> SEQ ID NO 44
<211> LENGTH: 6
<212> TYPE: PRT
<213> ORGANISM: Artificial Sequence
<220> FEATURE:
<223> OTHER INFORMATION: Synthesized

<400> SEQUENCE: 44

Met Phe Lys Leu Arg Phe
1               5

<210> SEQ ID NO 45
<211> LENGTH: 6
<212> TYPE: PRT
<213> ORGANISM: Artificial Sequence
<220> FEATURE:
<223> OTHER INFORMATION: Synthesized

<400> SEQUENCE: 45

Thr Phe Lys Leu Arg Phe
1               5

<210> SEQ ID NO 46
<211> LENGTH: 6
<212> TYPE: PRT
<213> ORGANISM: Artificial Sequence
<220> FEATURE:
<223> OTHER INFORMATION: Synthesized

<400> SEQUENCE: 46

Gln Phe Lys Leu Arg Phe
1               5

<210> SEQ ID NO 47
<211> LENGTH: 6
<212> TYPE: PRT
<213> ORGANISM: Artificial Sequence
<220> FEATURE:
<223> OTHER INFORMATION: Synthesized

<400> SEQUENCE: 47

Trp Phe Lys Leu Arg Phe
1               5

<210> SEQ ID NO 48
<211> LENGTH: 44
<212> TYPE: PRT
<213> ORGANISM: Tachypleus tridentatus
<220> FEATURE:
<221> NAME/KEY: misc_feature
<223> OTHER INFORMATION: Tachystatin A Peptide

<400> SEQUENCE: 48

Tyr Ser Arg Cys Gln Leu Gln Gly Phe Asn Cys Val Val Arg Ser Tyr
1               5                   10                  15

Gly Leu Pro Thr Ile Pro Cys Cys Arg Gly Leu Thr Cys Arg Ser Tyr
            20                  25                  30
```

```
Phe Pro Gly Ser Thr Tyr Gly Arg Cys Gln Arg Tyr
            35                  40

<210> SEQ ID NO 49
<211> LENGTH: 25
<212> TYPE: PRT
<213> ORGANISM: Androctonus australis

<400> SEQUENCE: 49

Arg Ser Val Cys Arg Gln Ile Lys Ile Cys Arg Arg Gly Gly Cys
1               5                   10                  15

Tyr Tyr Lys Cys Thr Asn Arg Pro Tyr
            20                  25

<210> SEQ ID NO 50
<211> LENGTH: 13
<212> TYPE: PRT
<213> ORGANISM: Unknown
<220> FEATURE:
<223> OTHER INFORMATION: Synthetic Tritrpticin

<400> SEQUENCE: 50

Val Arg Arg Phe Pro Trp Trp Trp Pro Phe Leu Arg Arg
1               5                   10

<210> SEQ ID NO 51
<211> LENGTH: 30
<212> TYPE: PRT
<213> ORGANISM: Homo sapiens
<220> FEATURE:
<221> NAME/KEY: misc_feature
<223> OTHER INFORMATION: HNP-3 Defensin

<400> SEQUENCE: 51

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 52
<211> LENGTH: 38
<212> TYPE: PRT
<213> ORGANISM: Phytolacca americana

<400> SEQUENCE: 52

Ala Gly Cys Ile Lys Asn Gly Gly Arg Cys Asn Ala Ser Ala Gly Pro
1               5                   10                  15

Pro Tyr Cys Cys Ser Ser Tyr Cys Phe Gln Ile Ala Gly Gln Ser Tyr
            20                  25                  30

Gly Val Cys Lys Asn Arg
            35

<210> SEQ ID NO 53
<211> LENGTH: 23
<212> TYPE: PRT
<213> ORGANISM: Unknown
<220> FEATURE:
<223> OTHER INFORMATION: Synthetic construct Magainin 2

<400> SEQUENCE: 53

Gly Ile Gly Lys Tyr Leu His Ser Ala Lys Lys Phe Gly Lys Ala Trp
1               5                   10                  15

Val Gly Glu Ile Met Asn Ser
            20
```

```
<210> SEQ ID NO 54
<211> LENGTH: 13
<212> TYPE: PRT
<213> ORGANISM: Bos taurus

<400> SEQUENCE: 54

Ile Leu Pro Trp Lys Trp Pro Trp Trp Pro Trp Arg Arg
1               5                   10

<210> SEQ ID NO 55
<211> LENGTH: 44
<212> TYPE: PRT
<213> ORGANISM: Heliothis virescens

<400> SEQUENCE: 55

Asp Lys Leu Ile Gly Ser Cys Val Trp Gly Ala Val Asn Tyr Thr Ser
1               5                   10                  15

Asp Cys Asn Gly Glu Cys Lys Arg Arg Gly Tyr Lys Gly Gly His Cys
                20                  25                  30

Gly Ser Phe Ala Asn Val Asn Cys Trp Cys Glu Thr
            35                  40

<210> SEQ ID NO 56
<211> LENGTH: 44
<212> TYPE: PRT
<213> ORGANISM: Heliothis virescens

<400> SEQUENCE: 56

Asp Lys Leu Ile Gly Ser Cys Val Trp Gly Ala Val Asn Tyr Thr Ser
1               5                   10                  15

Asp Cys Asn Gly Glu Cys Lys Arg Arg Gly Tyr Lys Gly Gly His Cys
                20                  25                  30

Gly Ser Phe Ala Asn Val Asn Cys Trp Cys Glu Thr
            35                  40

<210> SEQ ID NO 57
<211> LENGTH: 46
<212> TYPE: PRT
<213> ORGANISM: Pisum sativum
<220> FEATURE:
<221> NAME/KEY: misc_feature
<223> OTHER INFORMATION: Seed of pea defensin 1 (psd1)

<400> SEQUENCE: 57

Lys Thr Cys Glu His Leu Ala Asp Thr Tyr Arg Gly Val Cys Phe Thr
1               5                   10                  15

Asn Ala Ser Cys Asp Asp His Cys Lys Asn Lys Ala His Leu Ile Ser
                20                  25                  30

Gly Thr Cys His Asn Trp Lys Cys Phe Cys Thr Gln Asn Cys
            35                  40                  45

<210> SEQ ID NO 58
<211> LENGTH: 18
<212> TYPE: PRT
<213> ORGANISM: Unknown
<220> FEATURE:
<223> OTHER INFORMATION: Synthetic Gomesin

<400> SEQUENCE: 58

Gln Cys Arg Arg Leu Cys Tyr Lys Gln Arg Cys Val Thr Tyr Cys Arg
1               5                   10                  15

Gly Arg
```

```
<210> SEQ ID NO 59
<211> LENGTH: 25
<212> TYPE: PRT
<213> ORGANISM: Bos taurus
<220> FEATURE:
<221> NAME/KEY: misc_feature
<223> OTHER INFORMATION: Lactoferricin B

<400> SEQUENCE: 59

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 60
<211> LENGTH: 12
<212> TYPE: PRT
<213> ORGANISM: Unknown
<220> FEATURE:
<223> OTHER INFORMATION: Synthetic PW2

<400> SEQUENCE: 60

His Pro Leu Lys Gln Tyr Trp Trp Arg Pro Ser Ile
1               5                   10

<210> SEQ ID NO 61
<211> LENGTH: 20
<212> TYPE: PRT
<213> ORGANISM: Homo sapiens
<220> FEATURE:
<221> NAME/KEY: misc_feature
<223> OTHER INFORMATION: Hepcidin 20

<400> SEQUENCE: 61

Ile Cys Ile Phe Cys Cys Gly Cys Cys His Arg Ser Lys Cys Gly Met
1               5                   10                  15

Cys Cys Lys Thr
            20

<210> SEQ ID NO 62
<211> LENGTH: 25
<212> TYPE: PRT
<213> ORGANISM: Homo sapiens
<220> FEATURE:
<221> NAME/KEY: misc_feature
<223> OTHER INFORMATION: Hepcidin 25

<400> SEQUENCE: 62

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 63
<211> LENGTH: 30
<212> TYPE: PRT
<213> ORGANISM: Amaranthus caudatus

<400> SEQUENCE: 63

Val Gly Glu Cys Val Arg Gly Arg Cys Pro Ser Gly Met Cys Cys Ser
1               5                   10                  15

Gln Phe Gly Tyr Cys Gly Lys Gly Pro Lys Tyr Cys Gly Arg
            20                  25                  30

<210> SEQ ID NO 64
```

```
<211> LENGTH: 78
<212> TYPE: PRT
<213> ORGANISM: Amaranthus caudatus

<400> SEQUENCE: 64

Gly Tyr Phe Cys Glu Ser Cys Arg Lys Ile Ile Gln Lys Leu Glu Asp
1               5                   10                  15

Met Val Gly Pro Gln Pro Asn Glu Asp Thr Val Thr Gln Ala Ala Ser
            20                  25                  30

Gln Val Cys Asp Lys Leu Lys Ile Leu Arg Gly Leu Cys Lys Lys Ile
        35                  40                  45

Met Arg Ser Phe Leu Arg Arg Ile Ser Trp Asp Ile Leu Thr Gly Lys
    50                  55                  60

Lys Pro Gln Ala Ile Cys Val Asp Ile Lys Ile Cys Lys Glu
65                  70                  75

<210> SEQ ID NO 65
<211> LENGTH: 23
<212> TYPE: PRT
<213> ORGANISM: Xenopus laevis
<220> FEATURE:
<221> NAME/KEY: misc_feature
<223> OTHER INFORMATION: Magainin 2

<400> SEQUENCE: 65

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 66
<211> LENGTH: 26
<212> TYPE: PRT
<213> ORGANISM: Apis mellifera
<220> FEATURE:
<221> NAME/KEY: misc_feature
<223> OTHER INFORMATION: venom Melittin B

<400> SEQUENCE: 66

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 67
<211> LENGTH: 21
<212> TYPE: PRT
<213> ORGANISM: Podisus maculiventris

<400> SEQUENCE: 67

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 68
<211> LENGTH: 38
<212> TYPE: PRT
<213> ORGANISM: Mesembryanthemum crystallinum
<220> FEATURE:
<221> NAME/KEY: misc_feature
<223> OTHER INFORMATION: Antimicrobial peptide 1

<400> SEQUENCE: 68
```

```
Ala Lys Cys Ile Lys Asn Gly Lys Gly Cys Arg Glu Asp Gln Gly Pro
1               5                   10                  15

Pro Phe Cys Cys Ser Gly Phe Cys Tyr Arg Gln Val Gly Trp Ala Arg
            20                  25                  30

Gly Tyr Cys Lys Asn Arg
            35

<210> SEQ ID NO 69
<211> LENGTH: 13
<212> TYPE: PRT
<213> ORGANISM: Bos taurus
<220> FEATURE:
<221> NAME/KEY: misc_feature
<223> OTHER INFORMATION: Melanotropin alpha (Alpha-MSH)

<400> SEQUENCE: 69

Ser Tyr Ser Met Glu His Phe Arg Trp Gly Lys Pro Val
1               5                   10

<210> SEQ ID NO 70
<211> LENGTH: 33
<212> TYPE: PRT
<213> ORGANISM: Oryctolagus cuniculus
<220> FEATURE:
<221> NAME/KEY: misc_feature
<223> OTHER INFORMATION: Corticostatin III (MCP-1)

<400> SEQUENCE: 70

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 71
<211> LENGTH: 33
<212> TYPE: PRT
<213> ORGANISM: Oryctolagus cuniculus
<220> FEATURE:
<221> NAME/KEY: misc_feature
<223> OTHER INFORMATION: Corticostatin IV (MCP-2)

<400> SEQUENCE: 71

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 72
<211> LENGTH: 35
<212> TYPE: PRT
<213> ORGANISM: Antheraea pernyi
<220> FEATURE:
<221> NAME/KEY: misc_feature
<223> OTHER INFORMATION: Cecropin B

<400> SEQUENCE: 72

Lys Trp Lys Ile Phe Lys Lys Ile Glu Lys Val Gly Arg Asn Ile Arg
1               5                   10                  15

Asn Gly Ile Ile Lys Ala Gly Pro Ala Val Ala Val Leu Gly Glu Ala
            20                  25                  30

Lys Ala Leu
        35
```

<210> SEQ ID NO 73
<211> LENGTH: 48
<212> TYPE: PRT
<213> ORGANISM: Bos taurus
<220> FEATURE:
<221> NAME/KEY: misc_feature
<223> OTHER INFORMATION: Seminalplasmin

<400> SEQUENCE: 73

Ser Asp Glu Lys Ala Ser Pro Asp Lys His Arg Phe Ser Leu Ser
1               5                   10                  15

Arg Tyr Ala Lys Leu Ala Asn Arg Leu Ala Asn Pro Lys Leu Leu Glu
            20                  25                  30

Thr Phe Leu Ser Lys Trp Ile Gly Asp Arg Gly Asn Arg Ser Val Lys
        35                  40                  45

<210> SEQ ID NO 74
<211> LENGTH: 34
<212> TYPE: PRT
<213> ORGANISM: Oryctolagus cuniculus
<220> FEATURE:
<221> NAME/KEY: misc_feature
<223> OTHER INFORMATION: NP-3A defensin

<400> SEQUENCE: 74

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 75
<211> LENGTH: 30
<212> TYPE: PRT
<213> ORGANISM: Homo sapiens
<220> FEATURE:
<221> NAME/KEY: misc_feature
<223> OTHER INFORMATION: HNP-1 Defensin

<400> SEQUENCE: 75

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 76
<211> LENGTH: 29
<212> TYPE: PRT
<213> ORGANISM: Homo sapiens
<220> FEATURE:
<221> NAME/KEY: misc_feature
<223> OTHER INFORMATION: HNP-2 Defensin

<400> SEQUENCE: 76

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 77
<211> LENGTH: 33
<212> TYPE: PRT
<213> ORGANISM: Homo sapiens
<220> FEATURE:

```
<221> NAME/KEY: misc_feature
<223> OTHER INFORMATION: HNP-4 Defensin

<400> SEQUENCE: 77

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 78
<211> LENGTH: 24
<212> TYPE: PRT
<213> ORGANISM: Homo sapiens
<220> FEATURE:
<221> NAME/KEY: misc_feature
<223> OTHER INFORMATION: Histatin 5

<400> SEQUENCE: 78

Asp Ser His Ala Lys Arg His His Gly Tyr Lys Arg Lys Phe His Glu
1               5                   10                  15

Lys His His Ser His Arg Gly Tyr
            20

<210> SEQ ID NO 79
<211> LENGTH: 32
<212> TYPE: PRT
<213> ORGANISM: Homo sapiens
<220> FEATURE:
<221> NAME/KEY: misc_feature
<223> OTHER INFORMATION: Histatin 3

<400> SEQUENCE: 79

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30

<210> SEQ ID NO 80
<211> LENGTH: 12
<212> TYPE: PRT
<213> ORGANISM: Unknown
<220> FEATURE:
<223> OTHER INFORMATION: Histatin 8

<400> SEQUENCE: 80

Lys Phe His Glu Lys His His Ser His Arg Gly Tyr
1               5                   10

<210> SEQ ID NO 81
<211> LENGTH: 38
<212> TYPE: PRT
<213> ORGANISM: Bos taurus
<220> FEATURE:
<221> NAME/KEY: misc_feature
<223> OTHER INFORMATION: Tracheal antimicrobial peptide

<400> SEQUENCE: 81

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35
```

```
<210> SEQ ID NO 82
<211> LENGTH: 37
<212> TYPE: PRT
<213> ORGANISM: Mirabilis jalapa
<220> FEATURE:
<221> NAME/KEY: misc_feature
<223> OTHER INFORMATION: antimicrobial peptidic agent1 (MJ-antimicrobial
      peptidic agent1)

<400> SEQUENCE: 82

Gln Cys Ile Gly Asn Gly Gly Arg Cys Asn Glu Asn Val Gly Pro Pro
1               5                   10                  15

Tyr Cys Cys Ser Gly Phe Cys Leu Arg Gln Pro Gly Gln Gly Tyr Gly
            20                  25                  30

Tyr Cys Lys Asn Arg
        35

<210> SEQ ID NO 83
<211> LENGTH: 36
<212> TYPE: PRT
<213> ORGANISM: Mirabilis jalapa
<220> FEATURE:
<221> NAME/KEY: misc_feature
<223> OTHER INFORMATION: antimicrobial peptidic agent2 (MJ-antimicrobial
      peptidic agent2)

<400> SEQUENCE: 83

Cys Ile Gly Asn Gly Gly Arg Cys Asn Glu Asn Val Gly Pro Pro Tyr
1               5                   10                  15

Cys Cys Ser Gly Phe Cys Leu Arg Gln Pro Asn Gln Gly Tyr Gly Val
            20                  25                  30

Cys Arg Asn Arg
        35

<210> SEQ ID NO 84
<211> LENGTH: 33
<212> TYPE: PRT
<213> ORGANISM: Zea mays
<220> FEATURE:
<221> NAME/KEY: misc_feature
<223> OTHER INFORMATION: MBP-1

<400> SEQUENCE: 84

Arg Ser Gly Arg Gly Glu Cys Arg Arg Gln Cys Leu Arg Arg His Glu
1               5                   10                  15

Gly Gln Pro Trp Glu Thr Gln Glu Cys Met Arg Arg Cys Arg Arg Arg
            20                  25                  30

Gly

<210> SEQ ID NO 85
<211> LENGTH: 23
<212> TYPE: PRT
<213> ORGANISM: Brassica napus
<220> FEATURE:
<221> NAME/KEY: misc_feature
<223> OTHER INFORMATION: AFP2

<400> SEQUENCE: 85

Gln Lys Leu Cys Glu Arg Pro Ser Gly Thr Trp Ser Gly Val Cys Gly
1               5                   10                  15

Asn Asn Asn Ala Cys Lys Asn
            20

<210> SEQ ID NO 86
```

```
<211> LENGTH: 27
<212> TYPE: PRT
<213> ORGANISM: Brassica rapa
<220> FEATURE:
<221> NAME/KEY: misc_feature
<223> OTHER INFORMATION: AFP1

<400> SEQUENCE: 86

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn
            20                  25

<210> SEQ ID NO 87
<211> LENGTH: 27
<212> TYPE: PRT
<213> ORGANISM: Brassica rapa
<220> FEATURE:
<221> NAME/KEY: misc_feature
<223> OTHER INFORMATION: AFP2

<400> SEQUENCE: 87

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Arg
            20                  25

<210> SEQ ID NO 88
<211> LENGTH: 33
<212> TYPE: PRT
<213> ORGANISM: Phyllomedusa bicolor
<220> FEATURE:
<221> NAME/KEY: misc_feature
<223> OTHER INFORMATION: Adenoregulin

<400> SEQUENCE: 88

Gly Leu Trp Ser Lys Ile Lys Glu Val Gly Lys Glu Ala Ala Lys Ala
1               5                   10                  15

Ala Ala Lys Ala Ala Gly Lys Ala Ala Leu Gly Ala Val Ser Glu Ala
            20                  25                  30

Val

<210> SEQ ID NO 89
<211> LENGTH: 16
<212> TYPE: PRT
<213> ORGANISM: Sus scrofa
<220> FEATURE:
<221> NAME/KEY: misc_feature
<223> OTHER INFORMATION: Protegrin 2

<400> SEQUENCE: 89

Arg Gly Gly Arg Leu Cys Tyr Cys Arg Arg Arg Phe Cys Ile Cys Val
1               5                   10                  15

<210> SEQ ID NO 90
<211> LENGTH: 18
<212> TYPE: PRT
<213> ORGANISM: Sus scrofa
<220> FEATURE:
<221> NAME/KEY: misc_feature
<223> OTHER INFORMATION: Protegrin 3

<400> SEQUENCE: 90

Arg Gly Gly Gly Leu Cys Tyr Cys Arg Arg Arg Phe Cys Val Cys Val
1               5                   10                  15

Gly Arg
```

<210> SEQ ID NO 91
<211> LENGTH: 38
<212> TYPE: PRT
<213> ORGANISM: Macaca fascicularis
<220> FEATURE:
<221> NAME/KEY: misc_feature
<223> OTHER INFORMATION: Histatin 1

<400> SEQUENCE: 91

Asp Ser His Glu Glu Arg His His Gly Arg His Gly His His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
        35

<210> SEQ ID NO 92
<211> LENGTH: 24
<212> TYPE: PRT
<213> ORGANISM: Xenopus laevis
<220> FEATURE:
<221> NAME/KEY: misc_feature
<223> OTHER INFORMATION: Peptide PGQ

<400> SEQUENCE: 92

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 93
<211> LENGTH: 20
<212> TYPE: PRT
<213> ORGANISM: Rana catesbeiana
<220> FEATURE:
<221> NAME/KEY: misc_feature
<223> OTHER INFORMATION: Ranalexin

<400> SEQUENCE: 93

Phe Leu Gly Gly Leu Ile Lys Ile Val Pro Ala Met Ile Cys Ala Val
1               5                   10                  15

Thr Lys Lys Cys
            20

<210> SEQ ID NO 94
<211> LENGTH: 30
<212> TYPE: PRT
<213> ORGANISM: Cavia cutleri
<220> FEATURE:
<221> NAME/KEY: misc_feature
<223> OTHER INFORMATION: GNCP-2

<400> SEQUENCE: 94

Arg Cys Ile Cys Thr Thr Arg Thr Cys Arg Phe Pro Tyr Arg Arg Leu
1               5                   10                  15

Gly Thr Cys Leu Phe Gln Asn Arg Val Tyr Thr Phe Cys Cys
            20                  25                  30

<210> SEQ ID NO 95
<211> LENGTH: 18
<212> TYPE: PRT
<213> ORGANISM: Sus scrofa
<220> FEATURE:
<221> NAME/KEY: misc_feature
<223> OTHER INFORMATION: Protegrin 4

```
<400> SEQUENCE: 95

Arg Gly Gly Arg Leu Cys Tyr Cys Arg Gly Trp Ile Cys Phe Cys Val
1               5                   10                  15

Gly Arg

<210> SEQ ID NO 96
<211> LENGTH: 18
<212> TYPE: PRT
<213> ORGANISM: Sus scrofa
<220> FEATURE:
<221> NAME/KEY: misc_feature
<223> OTHER INFORMATION: Protegrin 5

<400> SEQUENCE: 96

Arg Gly Gly Arg Leu Cys Tyr Cys Arg Pro Arg Phe Cys Val Cys Val
1               5                   10                  15

Gly Arg

<210> SEQ ID NO 97
<211> LENGTH: 27
<212> TYPE: PRT
<213> ORGANISM: Bos taurus
<220> FEATURE:
<221> NAME/KEY: misc_feature
<223> OTHER INFORMATION: BMAP-27

<400> SEQUENCE: 97

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 98
<211> LENGTH: 28
<212> TYPE: PRT
<213> ORGANISM: Bos taurus
<220> FEATURE:
<221> NAME/KEY: misc_feature
<223> OTHER INFORMATION: BMAP-28

<400> SEQUENCE: 98

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 99
<211> LENGTH: 39
<212> TYPE: PRT
<213> ORGANISM: Bufo bufo gargarizans
<220> FEATURE:
<221> NAME/KEY: misc_feature
<223> OTHER INFORMATION: Buforin 1

<400> SEQUENCE: 99

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 100
```

```
<211> LENGTH: 21
<212> TYPE: PRT
<213> ORGANISM: Bufo bufo gargarizans
<220> FEATURE:
<221> NAME/KEY: misc_feature
<223> OTHER INFORMATION: Buforin II

<400> SEQUENCE: 100

Thr Arg Ser Ser Arg Ala Gly Leu Gln Phe Pro Val Gly Arg Val His
1               5                   10                  15

Arg Leu Leu Arg Lys
            20

<210> SEQ ID NO 101
<211> LENGTH: 34
<212> TYPE: PRT
<213> ORGANISM: Bos taurus
<220> FEATURE:
<221> NAME/KEY: misc_feature
<223> OTHER INFORMATION: BMAP-34

<400> SEQUENCE: 101

Gly Leu Phe Arg Arg Leu Arg Asp Ser Ile Arg Arg Gly Gln Gln Lys
1               5                   10                  15

Ile Leu Glu Lys Ala Arg Arg Ile Gly Glu Arg Ile Lys Asp Ile Phe
            20                  25                  30

Arg Gly

<210> SEQ ID NO 102
<211> LENGTH: 19
<212> TYPE: PRT
<213> ORGANISM: Trichoderma longibrachiatum
<220> FEATURE:
<221> NAME/KEY: misc_feature
<223> OTHER INFORMATION: Tricholongin

<400> SEQUENCE: 102

Ala Gly Phe Ala Ala Gln Ala Ala Ala Ser Leu Ala Pro Val Ala Ala
1               5                   10                  15

Gln Gln Leu

<210> SEQ ID NO 103
<211> LENGTH: 34
<212> TYPE: PRT
<213> ORGANISM: Phyllomedusa sauvagei
<220> FEATURE:
<221> NAME/KEY: misc_feature
<223> OTHER INFORMATION: Dermaseptin 1

<400> SEQUENCE: 103

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 104
<211> LENGTH: 45
<212> TYPE: PRT
<213> ORGANISM: Hevea brasiliensis
<220> FEATURE:
<221> NAME/KEY: misc_feature
<223> OTHER INFORMATION: Pseudo-hevein (Minor hevein)

<400> SEQUENCE: 104
```

```
Glu Gln Cys Gly Arg Gln Ala Gly Gly Lys Leu Cys Pro Asn Asn Leu
1               5                   10                  15

Cys Cys Ser Gln Tyr Gly Trp Cys Gly Ser Ser Asp Asp Tyr Cys Ser
            20                  25                  30

Pro Ser Lys Asn Cys Gln Ser Asn Cys Lys Gly Gly Gly
            35                  40                  45
```

<210> SEQ ID NO 105
<211> LENGTH: 33
<212> TYPE: PRT
<213> ORGANISM: Rana rugosa
<220> FEATURE:
<221> NAME/KEY: misc_feature
<223> OTHER INFORMATION: Gaegurin-1

<400> SEQUENCE: 105

```
Ser Leu Phe Ser Leu Ile Lys Ala Gly Ala Lys Phe Leu Gly Lys Asn
1               5                   10                  15

Leu Leu Lys Gln Gly Ala Cys Tyr Ala Ala Cys Lys Ala Ser Lys Gln
            20                  25                  30

Cys
```

<210> SEQ ID NO 106
<211> LENGTH: 36
<212> TYPE: PRT
<213> ORGANISM: Phyllomedusa bicolor
<220> FEATURE:
<221> NAME/KEY: misc_feature
<223> OTHER INFORMATION: Skin peptide tyrosine-tyrosine

<400> SEQUENCE: 106

```
Tyr Pro Pro Lys Pro Glu Ser Pro Gly Glu Asp Ala Ser Pro Glu Glu
1               5                   10                  15

Met Asn Lys Tyr Leu Thr Ala Leu Arg His Tyr Ile Asn Leu Val Thr
            20                  25                  30

Arg Gln Arg Tyr
            35
```

<210> SEQ ID NO 107
<211> LENGTH: 50
<212> TYPE: PRT
<213> ORGANISM: Penaeus vannamei
<220> FEATURE:
<221> NAME/KEY: misc_feature
<223> OTHER INFORMATION: Penaeidin-1

<400> SEQUENCE: 107

```
Tyr Arg Gly Gly Tyr Thr Gly Pro Ile Pro Arg Pro Pro Pro Ile Gly
1               5                   10                  15

Arg Pro Pro Leu Arg Leu Val Val Cys Ala Cys Tyr Arg Leu Ser Val
            20                  25                  30

Ser Asp Ala Arg Asn Cys Cys Ile Lys Phe Gly Ser Cys Cys His Leu
            35                  40                  45

Val Lys
    50
```

<210> SEQ ID NO 108
<211> LENGTH: 33
<212> TYPE: PRT
<213> ORGANISM: Mesocricetus auratus
<220> FEATURE:
<221> NAME/KEY: misc_feature
<223> OTHER INFORMATION: Neutrophil defensin 1 (HANP-1)

```
<400> SEQUENCE: 108

Val Thr Cys Phe Cys Arg Arg Arg Gly Cys Ala Ser Arg Glu Arg His
1               5                   10                  15

Ile Gly Tyr Cys Arg Phe Gly Asn Thr Ile Tyr Arg Leu Cys Cys Arg
            20                  25                  30

Arg

<210> SEQ ID NO 109
<211> LENGTH: 33
<212> TYPE: PRT
<213> ORGANISM: Mesocricetus auratus
<220> FEATURE:
<221> NAME/KEY: misc_feature
<223> OTHER INFORMATION: Neutrophil defensin 3 (HANP-3)

<400> SEQUENCE: 109

Val Thr Cys Phe Cys Arg Arg Arg Gly Cys Ala Ser Arg Glu Arg Leu
1               5                   10                  15

Ile Gly Tyr Cys Arg Phe Gly Asn Thr Ile Tyr Gly Leu Cys Cys Arg
            20                  25                  30

Arg

<210> SEQ ID NO 110
<211> LENGTH: 21
<212> TYPE: PRT
<213> ORGANISM: Misgurnus anguillicaudatus
<220> FEATURE:
<221> NAME/KEY: misc_feature
<223> OTHER INFORMATION: Misgurin

<400> SEQUENCE: 110

Arg Gln Arg Val Glu Glu Leu Ser Lys Phe Ser Lys Lys Gly Ala Ala
1               5                   10                  15

Ala Arg Arg Arg Lys
            20

<210> SEQ ID NO 111
<211> LENGTH: 41
<212> TYPE: PRT
<213> ORGANISM: Pharbitis nil
<220> FEATURE:
<221> NAME/KEY: misc_feature
<223> OTHER INFORMATION: PN-antimicrobial peptidic agent

<400> SEQUENCE: 111

Gln Gln Cys Gly Arg Gln Ala Ser Gly Arg Leu Cys Gly Asn Arg Leu
1               5                   10                  15

Cys Cys Ser Gln Trp Gly Tyr Cys Gly Ser Thr Ala Ser Tyr Cys Gly
            20                  25                  30

Ala Gly Cys Gln Ser Gln Cys Arg Ser
        35                  40

<210> SEQ ID NO 112
<211> LENGTH: 19
<212> TYPE: PRT
<213> ORGANISM: Oncorhynchus mykiss
<220> FEATURE:
<221> NAME/KEY: misc_feature
<223> OTHER INFORMATION: Histone H2B-1(HLP-1)(Fragment)

<400> SEQUENCE: 112

Pro Asp Pro Ala Lys Thr Ala Pro Lys Lys Gly Ser Lys Lys Ala Val
1               5                   10                  15
```

Thr Lys Ala

<210> SEQ ID NO 113
<211> LENGTH: 17
<212> TYPE: PRT
<213> ORGANISM: Oncorhynchus mykiss
<220> FEATURE:
<221> NAME/KEY: misc_feature
<223> OTHER INFORMATION: Histone H2B-3(HLP-3)(Fragment)

<400> SEQUENCE: 113

Pro Asp Pro Ala Lys Thr Ala Pro Lys Lys Ser Lys Lys Ala Val
1               5                   10                  15

Thr

<210> SEQ ID NO 114
<211> LENGTH: 30
<212> TYPE: PRT
<213> ORGANISM: Macaca mulatta
<220> FEATURE:
<221> NAME/KEY: misc_feature
<223> OTHER INFORMATION: neutrophil defensin 2 (RMAD-2)

<400> SEQUENCE: 114

Ala Cys Tyr Cys Arg Ile Pro Ala Cys Leu Ala Gly Glu Arg Arg Tyr
1               5                   10                  15

Gly Thr Cys Phe Tyr Met Gly Arg Val Trp Ala Phe Cys Cys
            20                  25                  30

<210> SEQ ID NO 115
<211> LENGTH: 36
<212> TYPE: PRT
<213> ORGANISM: Pseudacanthotermes spiniger
<220> FEATURE:
<221> NAME/KEY: misc_feature
<223> OTHER INFORMATION: Termicin

<400> SEQUENCE: 115

Ala Cys Asn Phe Gln Ser Cys Trp Ala Thr Cys Gln Ala Gln His Ser
1               5                   10                  15

Ile Tyr Phe Arg Arg Ala Phe Cys Asp Arg Ser Gln Cys Lys Cys Val
            20                  25                  30

Phe Val Arg Gly
        35

<210> SEQ ID NO 116
<211> LENGTH: 25
<212> TYPE: PRT
<213> ORGANISM: Pseudacanthotermas spiniger
<220> FEATURE:
<221> NAME/KEY: misc_feature
<223> OTHER INFORMATION: Spingerin

<400> SEQUENCE: 116

His Val Asp Lys Lys Val Ala Asp Lys Val Leu Leu Leu Lys Gln Leu
1               5                   10                  15

Arg Ile Met Arg Leu Leu Thr Arg Leu
            20                  25

<210> SEQ ID NO 117
<211> LENGTH: 13
<212> TYPE: PRT
<213> ORGANISM: Litoria raniformis
<220> FEATURE:
<221> NAME/KEY: misc_feature
<223> OTHER INFORMATION: Aurein 1.1

```
<400> SEQUENCE: 117

Gly Leu Phe Asp Ile Ile Lys Lys Ile Ala Glu Ser Ile
1               5                   10

<210> SEQ ID NO 118
<211> LENGTH: 30
<212> TYPE: PRT
<213> ORGANISM: Pachycondyla goeldii
<220> FEATURE:
<221> NAME/KEY: misc_feature
<223> OTHER INFORMATION: Ponericin G1

<400> SEQUENCE: 118

Gly Trp Lys Asp Trp Ala Lys Lys Ala Gly Gly Trp Leu Lys Lys Lys
1               5                   10                  15

Gly Pro Gly Met Ala Lys Ala Ala Leu Lys Ala Ala Met Gln
            20                  25                  30

<210> SEQ ID NO 119
<211> LENGTH: 24
<212> TYPE: PRT
<213> ORGANISM: Rana berlandieri
<220> FEATURE:
<221> NAME/KEY: misc_feature
<223> OTHER INFORMATION: Brevinin-1BB

<400> SEQUENCE: 119

Phe Leu Pro Ala Ile Ala Gly Met Ala Ala Lys Phe Leu Pro Lys Ile
1               5                   10                  15

Phe Cys Ala Ile Ser Lys Lys Cys
            20

<210> SEQ ID NO 120
<211> LENGTH: 20
<212> TYPE: PRT
<213> ORGANISM: Rana clamitans
<220> FEATURE:
<221> NAME/KEY: misc_feature
<223> OTHER INFORMATION: Ranalexin-1CB

<400> SEQUENCE: 120

Phe Leu Gly Gly Leu Met Lys Ala Phe Pro Ala Ile Ile Cys Ala Val
1               5                   10                  15

Thr Lys Lys Cys
            20

<210> SEQ ID NO 121
<211> LENGTH: 31
<212> TYPE: PRT
<213> ORGANISM: Rana clamitans
<220> FEATURE:
<221> NAME/KEY: misc_feature
<223> OTHER INFORMATION: Ranatuerin-2CA

<400> SEQUENCE: 121

Gly Leu Phe Leu Asp Thr Leu Lys Gly Ala Ala Lys Asp Val Ala Gly
1               5                   10                  15

Lys Leu Leu Glu Gly Leu Lys Cys Lys Ile Ala Gly Cys Lys Pro
            20                  25                  30

<210> SEQ ID NO 122
<211> LENGTH: 27
<212> TYPE: PRT
<213> ORGANISM: Rana clamitans
<220> FEATURE:
```

<221> NAME/KEY: misc_feature
<223> OTHER INFORMATION: Ranatuerin-2CB

<400> SEQUENCE: 122

Gly Leu Phe Leu Asp Thr Leu Lys Gly Leu Ala Gly Lys Leu Leu Gln
1               5                   10                  15

Gly Leu Lys Cys Ile Lys Ala Gly Cys Lys Pro
            20                  25

<210> SEQ ID NO 123
<211> LENGTH: 40
<212> TYPE: PRT
<213> ORGANISM: Ginkgo biloba
<220> FEATURE:
<221> NAME/KEY: misc_feature
<223> OTHER INFORMATION: Ginkbilobin

<400> SEQUENCE: 123

Ala Asn Thr Ala Phe Val Ser Ser Ala His Asn Thr Gln Lys Ile Pro
1               5                   10                  15

Ala Gly Ala Pro Phe Asn Arg Asn Leu Arg Ala Met Leu Ala Asp Leu
            20                  25                  30

Arg Gln Asn Ala Ala Phe Ala Gly
        35                  40

<210> SEQ ID NO 124
<211> LENGTH: 20
<212> TYPE: PRT
<213> ORGANISM: Basella alba
<220> FEATURE:
<221> NAME/KEY: misc_feature
<223> OTHER INFORMATION: Alpha-basrubrin (Fragment)

<400> SEQUENCE: 124

Gly Ala Asp Phe Gln Glu Cys Met Lys Glu His Ser Gln Lys Gln His
1               5                   10                  15

Gln His Gln Gly
            20

<210> SEQ ID NO 125
<211> LENGTH: 24
<212> TYPE: PRT
<213> ORGANISM: Pseudis paradoxa
<220> FEATURE:
<221> NAME/KEY: misc_feature
<223> OTHER INFORMATION: Pseudin 1

<400> SEQUENCE: 125

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 126
<211> LENGTH: 45
<212> TYPE: PRT
<213> ORGANISM: Parabuthus schlechteri
<220> FEATURE:
<221> NAME/KEY: misc_feature
<223> OTHER INFORMATION: Parabutoporin

<400> SEQUENCE: 126

Phe Lys Leu Gly Ser Phe Leu Lys Lys Ala Trp Lys Ser Lys Leu Ala
1               5                   10                  15

Lys Lys Leu Arg Ala Lys Gly Lys Glu Met Leu Lys Asp Tyr Ala Lys

```
            20                  25                  30

Gly Leu Leu Glu Gly Gly Ser Glu Glu Val Pro Gly Gln
        35                  40                  45

<210> SEQ ID NO 127
<211> LENGTH: 44
<212> TYPE: PRT
<213> ORGANISM: Opistophthalmus carinatus
<220> FEATURE:
<221> NAME/KEY: misc_feature
<223> OTHER INFORMATION: Opistoporin 1

<400> SEQUENCE: 127

Gly Lys Val Trp Asp Trp Ile Lys Ser Thr Ala Lys Lys Leu Trp Asn
1               5                   10                  15

Ser Glu Pro Val Lys Glu Leu Lys Asn Thr Ala Leu Asn Ala Ala Lys
            20                  25                  30

Asn Leu Val Ala Glu Lys Ile Gly Ala Thr Pro Ser
        35                  40

<210> SEQ ID NO 128
<211> LENGTH: 44
<212> TYPE: PRT
<213> ORGANISM: Opistophthalmus carinatus
<220> FEATURE:
<221> NAME/KEY: misc_feature
<223> OTHER INFORMATION: Opistoporin 2

<400> SEQUENCE: 128

Gly Lys Val Trp Asp Trp Ile Lys Ser Thr Ala Lys Lys Leu Trp Asn
1               5                   10                  15

Ser Glu Pro Val Lys Glu Leu Lys Asn Thr Ala Leu Asn Ala Ala Lys
            20                  25                  30

Asn Phe Val Ala Glu Lys Ile Gly Ala Thr Pro Ser
        35                  40

<210> SEQ ID NO 129
<211> LENGTH: 12
<212> TYPE: PRT
<213> ORGANISM: Oncorhynchus mykiss
<220> FEATURE:
<221> NAME/KEY: misc_feature
<223> OTHER INFORMATION: Histone H2A (Fragment)

<400> SEQUENCE: 129

Ala Glu Arg Val Gly Ala Gly Ala Pro Val Tyr Leu
1               5                   10

<210> SEQ ID NO 130
<211> LENGTH: 33
<212> TYPE: PRT
<213> ORGANISM: Dolabella auricularia
<220> FEATURE:
<221> NAME/KEY: misc_feature
<223> OTHER INFORMATION: Dolabellanin B2

<400> SEQUENCE: 130

Ser His Gln Asp Cys Tyr Glu Ala Leu His Lys Cys Met Ala Ser His
1               5                   10                  15

Ser Lys Pro Phe Ser Cys Ser Met Lys Phe His Met Cys Leu Gln Gln
            20                  25                  30

Gln

<210> SEQ ID NO 131
```

```
<211> LENGTH: 35
<212> TYPE: PRT
<213> ORGANISM: Heliothis virescens
<220> FEATURE:
<221> NAME/KEY: misc_feature
<223> OTHER INFORMATION: Cecropin A

<400> SEQUENCE: 131

Arg Trp Lys Val Phe Lys Lys Ile Glu Lys Val Gly Arg Asn Ile Arg
1               5                   10                  15

Asp Gly Val Ile Lys Ala Ala Pro Ala Ile Glu Val Leu Gly Gln Ala
            20                  25                  30

Lys Ala Leu
        35

<210> SEQ ID NO 132
<211> LENGTH: 35
<212> TYPE: PRT
<213> ORGANISM: Homo sapiens
<220> FEATURE:
<221> NAME/KEY: misc_feature
<223> OTHER INFORMATION: HNP-5 Defensin

<400> SEQUENCE: 132

Gln Ala Arg Ala Thr Cys Tyr Cys Arg Thr Gly Arg Cys Ala Thr Arg
1               5                   10                  15

Glu Ser Leu Ser Gly Val Cys Glu Ile Ser Gly Arg Leu Tyr Arg Leu
            20                  25                  30

Cys Cys Arg
        35

<210> SEQ ID NO 133
<211> LENGTH: 35
<212> TYPE: PRT
<213> ORGANISM: Homo sapiens
<220> FEATURE:
<221> NAME/KEY: misc_feature
<223> OTHER INFORMATION: HNP-6 Defensin

<400> SEQUENCE: 133

Ser Thr Arg Ala Phe Thr Cys His Cys Arg Arg Ser Cys Tyr Ser Thr
1               5                   10                  15

Glu Tyr Ser Tyr Gly Thr Cys Thr Val Met Gly Ile Asn His Arg Phe
            20                  25                  30

Cys Cys Leu
        35

<210> SEQ ID NO 134
<211> LENGTH: 84
<212> TYPE: PRT
<213> ORGANISM: Holotrichia diomphalia
<220> FEATURE:
<221> NAME/KEY: misc_feature
<223> OTHER INFORMATION: Holotricin 3

<400> SEQUENCE: 134

Tyr Gly Pro Gly Asp Gly His Gly Gly Gly His Gly Gly Gly His Gly
1               5                   10                  15

Gly Gly His Gly Asn Gly Gln Gly Gly Gly His Gly His Gly Pro Gly
            20                  25                  30

Gly Gly Phe Gly Gly Gly His Gly Gly Gly His Gly Gly Gly Gly Arg
        35                  40                  45

Gly Gly Gly Gly Ser Gly Gly Gly Ser Pro Gly His Gly Ala Gly
    50                  55                  60
```

Gly Gly Tyr Pro Gly Gly His Gly Gly Gly His His Gly Gly Tyr Gln
65                  70                  75                  80

Thr His Gly Tyr

<210> SEQ ID NO 135
<211> LENGTH: 45
<212> TYPE: PRT
<213> ORGANISM: Bos taurus
<220> FEATURE:
<221> NAME/KEY: misc_feature
<223> OTHER INFORMATION: Lingual antimicrobial peptide

<400> SEQUENCE: 135

Gly Phe Thr Gln Gly Val Arg Asn Ser Gln Ser Cys Arg Arg Asn Lys
1               5                   10                  15

Gly Ile Cys Val Pro Ile Arg Cys Pro Gly Ser Met Arg Gln Ile Gly
            20                  25                  30

Thr Cys Leu Gly Ala Gln Val Lys Cys Cys Arg Arg Lys
        35                  40                  45

<210> SEQ ID NO 136
<211> LENGTH: 29
<212> TYPE: PRT
<213> ORGANISM: Rattus norvegicus
<220> FEATURE:
<221> NAME/KEY: misc_feature
<223> OTHER INFORMATION: RatNP-3

<400> SEQUENCE: 136

Cys Ser Cys Arg Thr Ser Ser Cys Arg Phe Gly Glu Arg Leu Ser Gly
1               5                   10                  15

Ala Cys Arg Leu Asn Gly Arg Ile Tyr Arg Leu Cys Cys
            20                  25

<210> SEQ ID NO 137
<211> LENGTH: 31
<212> TYPE: PRT
<213> ORGANISM: Cavia cutleri
<220> FEATURE:
<221> NAME/KEY: misc_feature
<223> OTHER INFORMATION: GNCP-1

<400> SEQUENCE: 137

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 138
<211> LENGTH: 47
<212> TYPE: PRT
<213> ORGANISM: Penaeus vannamei
<220> FEATURE:
<221> NAME/KEY: misc_feature
<223> OTHER INFORMATION: Penaeidin-4a

<400> SEQUENCE: 138

His Ser Ser Gly Tyr Thr Arg Pro Leu Pro Lys Pro Ser Arg Pro Ile
1               5                   10                  15

Phe Ile Arg Pro Ile Gly Cys Asp Val Cys Tyr Gly Ile Pro Ser Ser
            20                  25                  30

Thr Ala Arg Leu Cys Cys Phe Arg Tyr Gly Asp Cys Cys His Arg
        35                  40                  45

```
<210> SEQ ID NO 139
<211> LENGTH: 6
<212> TYPE: PRT
<213> ORGANISM: Bos taurus
<220> FEATURE:
<221> NAME/KEY: misc_feature
<223> OTHER INFORMATION: hexapeptide

<400> SEQUENCE: 139

Arg Arg Trp Gln Trp Arg
1               5

<210> SEQ ID NO 140
<211> LENGTH: 18
<212> TYPE: PRT
<213> ORGANISM: Penaeus vannamei

<400> SEQUENCE: 140

Lys Trp Lys Leu Phe Lys Lys Ile Pro Lys Phe Leu His Leu Ala Lys
1               5                   10                  15

Lys Phe

<210> SEQ ID NO 141
<211> LENGTH: 20
<212> TYPE: PRT
<213> ORGANISM: Homo sapiens
<220> FEATURE:
<221> NAME/KEY: misc_feature
<223> OTHER INFORMATION: MUC7 20-Mer

<400> SEQUENCE: 141

Leu Ala His Gln Lys Pro Phe Ile Arg Lys Ser Tyr Lys Cys Leu His
1               5                   10                  15

Lys Arg Cys Arg
            20

<210> SEQ ID NO 142
<211> LENGTH: 21
<212> TYPE: PRT
<213> ORGANISM: Rana nigromaculata
<220> FEATURE:
<221> NAME/KEY: misc_feature
<223> OTHER INFORMATION: Nigrocin 2

<400> SEQUENCE: 142

Gly Leu Leu Ser Lys Val Leu Gly Val Gly Lys Lys Val Leu Cys Gly
1               5                   10                  15

Val Ser Gly Leu Cys
            20

<210> SEQ ID NO 143
<211> LENGTH: 33
<212> TYPE: PRT
<213> ORGANISM: Rana nigromaculata
<220> FEATURE:
<221> NAME/KEY: misc_feature
<223> OTHER INFORMATION: Nigrocin 1

<400> SEQUENCE: 143

Gly Leu Leu Asp Ser Ile Lys Gly Met Ala Ile Ser Ala Gly Lys Gly
1               5                   10                  15

Ala Leu Gln Asn Leu Leu Lys Val Ala Ser Cys Lys Leu Asp Lys Thr
            20                  25                  30

Cys
```

```
<210> SEQ ID NO 144
<211> LENGTH: 10
<212> TYPE: PRT
<213> ORGANISM: Unknown
<220> FEATURE:
<223> OTHER INFORMATION: lactoferrin (Lf) peptide 2

<400> SEQUENCE: 144

Phe Lys Cys Arg Arg Trp Gln Trp Arg Met
1               5                   10

<210> SEQ ID NO 145
<211> LENGTH: 18
<212> TYPE: PRT
<213> ORGANISM: Impatiens balsamina
<220> FEATURE:
<221> NAME/KEY: misc_feature
<223> OTHER INFORMATION: Ib-antimicrobial peptidic agent3

<400> SEQUENCE: 145

Arg His Arg Cys Cys Ala Trp Gly Pro Gly Arg Lys Tyr Cys Lys Arg
1               5                   10                  15

Trp Cys

<210> SEQ ID NO 146
<211> LENGTH: 18
<212> TYPE: PRT
<213> ORGANISM: Impatiens balsamina
<220> FEATURE:
<221> NAME/KEY: misc_feature
<223> OTHER INFORMATION: Ib-antimicrobial peptidic agent4

<400> SEQUENCE: 146

Gly Arg Arg Cys Cys Gly Trp Gly Pro Gly Arg Arg Tyr Cys Arg Arg
1               5                   10                  15

Trp Cys

<210> SEQ ID NO 147
<211> LENGTH: 14
<212> TYPE: PRT
<213> ORGANISM: Unknown
<220> FEATURE:
<223> OTHER INFORMATION: Synthesis dhvar4

<400> SEQUENCE: 147

Lys Arg Leu Phe Lys Lys Leu Leu Phe Ser Leu Arg Lys Tyr
1               5                   10

<210> SEQ ID NO 148
<211> LENGTH: 14
<212> TYPE: PRT
<213> ORGANISM: Unknown
<220> FEATURE:
<223> OTHER INFORMATION: Synthesis dhvar5

<400> SEQUENCE: 148

Leu Leu Leu Phe Leu Leu Lys Lys Arg Lys Lys Arg Lys Tyr
1               5                   10

<210> SEQ ID NO 149
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
```

```
<222> LOCATION: (1)..(6)
<223> OTHER INFORMATION: X = any amino acid

<400> SEQUENCE: 149

Xaa Xaa Xaa Xaa Xaa Cys
1               5

<210> SEQ ID NO 150
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 150

Xaa Xaa Xaa Xaa Phe Cys
1               5

<210> SEQ ID NO 151
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 151

Xaa Xaa Xaa Xaa Asn Cys
1               5

<210> SEQ ID NO 152
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 152

Xaa Xaa Xaa Xaa Trp Cys
1               5

<210> SEQ ID NO 153
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 153

Xaa Xaa Xaa Xaa Ile Cys
1               5

<210> SEQ ID NO 154
<211> LENGTH: 6
<212> TYPE: PRT
```

<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 154

Xaa Xaa Xaa Xaa Thr Cys
1               5

<210> SEQ ID NO 155
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 155

Xaa Xaa Xaa Xaa Tyr Cys
1               5

<210> SEQ ID NO 156
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 156

Xaa Xaa Xaa Xaa Val Cys
1               5

<210> SEQ ID NO 157
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 157

Xaa Xaa Xaa Xaa Met Cys
1               5

<210> SEQ ID NO 158
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 158

Xaa Xaa Xaa Xaa Gly Cys
1               5

```
<210> SEQ ID NO 159
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 159

Xaa Xaa Xaa Xaa Glu Cys
1               5

<210> SEQ ID NO 160
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 160

Xaa Xaa Xaa Xaa Ser Cys
1               5

<210> SEQ ID NO 161
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 161

Xaa Xaa Xaa Xaa Leu Cys
1               5

<210> SEQ ID NO 162
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 162

Xaa Xaa Xaa Xaa Pro Cys
1               5

<210> SEQ ID NO 163
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid
```

<400> SEQUENCE: 163

Xaa Xaa Xaa Xaa His Cys
1               5

<210> SEQ ID NO 164
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 164

Xaa Xaa Xaa Xaa Cys Cys
1               5

<210> SEQ ID NO 165
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 165

Xaa Xaa Xaa Xaa Ala Cys
1               5

<210> SEQ ID NO 166
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 166

Xaa Xaa Xaa Xaa Lys Cys
1               5

<210> SEQ ID NO 167
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 167

Xaa Xaa Xaa Xaa Gln Cys
1               5

<210> SEQ ID NO 168
<211> LENGTH: 6
<212> TYPE: PRT
<213> ORGANISM: Artificial Sequence
<220> FEATURE:

```
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 168

Xaa Xaa Xaa Xaa Arg Cys
1               5

<210> SEQ ID NO 169
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 169

Xaa Xaa Xaa Xaa Asp Cys
1               5

<210> SEQ ID NO 170
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 170

Xaa Xaa Xaa Xaa Cys Tyr
1               5

<210> SEQ ID NO 171
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 171

Xaa Xaa Xaa Xaa Cys Gln
1               5

<210> SEQ ID NO 172
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 172

Xaa Xaa Xaa Xaa Tyr Ser
1               5
```

```
<210> SEQ ID NO 173
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 173

Xaa Xaa Xaa Xaa Tyr Asp
1               5

<210> SEQ ID NO 174
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 174

Xaa Xaa Xaa Xaa Thr Gln
1               5

<210> SEQ ID NO 175
<211> LENGTH: 6
<212> TYPE: PRT
<213> ORGANISM: Artificial Sequence
<220> FEATURE:
<223> OTHER INFORMATION: Synthesized

<400> SEQUENCE: 175

Trp Thr Phe Arg Tyr Cys
1               5

<210> SEQ ID NO 176
<211> LENGTH: 6
<212> TYPE: PRT
<213> ORGANISM: Artificial Sequence
<220> FEATURE:
<223> OTHER INFORMATION: Synthesized

<400> SEQUENCE: 176

Cys Tyr Arg Phe Thr Trp
1               5

<210> SEQ ID NO 177
<211> LENGTH: 11
<212> TYPE: PRT
<213> ORGANISM: Glomerella cingulata

<400> SEQUENCE: 177

Gly Tyr Phe Ser Tyr Pro His Gly Asn Leu Phe
1               5                   10

<210> SEQ ID NO 178
<211> LENGTH: 13
<212> TYPE: PRT
<213> ORGANISM: Saccharomyces cerevisiae

<400> SEQUENCE: 178

Trp His Trp Leu Gln Leu Lys Pro Gly Gln Pro Met Tyr
1               5                   10
```

```
<210> SEQ ID NO 179
<211> LENGTH: 13
<212> TYPE: PRT
<213> ORGANISM: Saccharomyces kluyveri

<400> SEQUENCE: 179

Trp His Trp Leu Ser Phe Ser Lys Gly Gln Pro Met Tyr
1               5                   10

<210> SEQ ID NO 180
<211> LENGTH: 19
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (3)..(3)
<223> OTHER INFORMATION: Nle

<400> SEQUENCE: 180

Tyr Asn Leu Glu Asp His Pro Gln Gly Asp His Pro Lys Leu Gln Leu
1               5                   10                  15

Trp His Trp

<210> SEQ ID NO 181
<211> LENGTH: 15
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (3)..(3)
<223> OTHER INFORMATION: Nle

<400> SEQUENCE: 181

Tyr Asn Leu Glu Pro Gln Gly Pro Lys Leu Gln Leu Trp His Trp
1               5                   10                  15

<210> SEQ ID NO 182
<211> LENGTH: 13
<212> TYPE: PRT
<213> ORGANISM: Artificial Sequence
<220> FEATURE:
<223> OTHER INFORMATION: Synthesized

<400> SEQUENCE: 182

Tyr Met Pro Gln Gly Pro Lys Leu Gln Leu Phe His Trp
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthesized

<400> SEQUENCE: 183

Tyr Met Pro Gln Gly Pro Lys Leu Gln Leu Trp His
1               5                   10

<210> SEQ ID NO 184
<211> LENGTH: 13
<212> TYPE: PRT
<213> ORGANISM: Artificial Sequence
<220> FEATURE:
```

<223> OTHER INFORMATION: Synthesized

<400> SEQUENCE: 184

Tyr Met Pro Gln Gly Pro Arg Leu Asn Leu Trp His Trp
1               5                   10

<210> SEQ ID NO 185
<211> LENGTH: 26
<212> TYPE: PRT
<213> ORGANISM: Magnaporthe grisea

<400> SEQUENCE: 185

Met Ser Pro Ser Thr Lys Asn Ile Pro Ala Pro Val Ala Gly Ala Arg
1               5                   10                  15
Ala Gly Pro Ile His Tyr Cys Val Ile Met
            20                  25

<210> SEQ ID NO 186
<211> LENGTH: 24
<212> TYPE: PRT
<213> ORGANISM: Neurospora crassa

<400> SEQUENCE: 186

Met Pro Ser Thr Ala Ala Ser Thr Arg Val Pro Gln Thr Thr Met Asn
1               5                   10                  15
Phe Asn Gly Tyr Cys Val Val Met
            20

<210> SEQ ID NO 187
<211> LENGTH: 23
<212> TYPE: PRT
<213> ORGANISM: Cryphonectria parasitica

<400> SEQUENCE: 187

Met Pro Ser Asn Thr Gln Thr Ser Asn Ser Ser Met Gly Val Asn Gly
1               5                   10                  15
Tyr Ser Tyr Cys Val Val Met
            20

<210> SEQ ID NO 188
<211> LENGTH: 11
<212> TYPE: PRT
<213> ORGANISM: Magnaporthe grisea

<400> SEQUENCE: 188

Gln Trp Cys Pro Arg Arg Gly Gln Pro Cys Trp
1               5                   10

<210> SEQ ID NO 189
<211> LENGTH: 11
<212> TYPE: PRT
<213> ORGANISM: Neurospora crassa

<400> SEQUENCE: 189

Gln Trp Cys Arg Ile His Gly Gln Ser Cys Trp
1               5                   10

<210> SEQ ID NO 190
<211> LENGTH: 13
<212> TYPE: PRT
<213> ORGANISM: Saccharomyces cerevisiae

<400> SEQUENCE: 190

Trp His Trp Leu Gln Leu Lys Pro Gly Gln Pro Met Tyr

<210> SEQ ID NO 191
<211> LENGTH: 10
<212> TYPE: PRT
<213> ORGANISM: Cryphonectria parasitica

<400> SEQUENCE: 191

Trp Cys Leu Phe His Gly Glu Gly Cys Trp
1               5                   10

<210> SEQ ID NO 192
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(4)
<223> OTHER INFORMATION: X = any amino acid

<400> SEQUENCE: 192

Xaa Ala Ala Cys
1

<210> SEQ ID NO 193
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(10)
<223> OTHER INFORMATION: X = any amino acid

<400> SEQUENCE: 193

Trp Cys Xaa Xaa Gly Xaa Xaa Xaa Cys Trp
1               5                   10

<210> SEQ ID NO 194
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 194

Xaa Xaa Xaa Xaa Cys Ile
1               5

<210> SEQ ID NO 195
<211> LENGTH: 10
<212> TYPE: PRT
<213> ORGANISM: Fusarium graminearum

<400> SEQUENCE: 195

Trp Cys Gln Gln Lys Gly Gln Pro Cys Trp
1               5                   10

<210> SEQ ID NO 196
<211> LENGTH: 10
<212> TYPE: PRT
<213> ORGANISM: Fusarium graminearum

```
<400> SEQUENCE: 196

Trp Cys Thr Trp Lys Gly Gln Pro Cys Trp
1               5                   10

<210> SEQ ID NO 197
<211> LENGTH: 7
<212> TYPE: PRT
<213> ORGANISM: Artificial Sequence
<220> FEATURE:
<223> OTHER INFORMATION: Synthesized

<400> SEQUENCE: 197

Phe Arg Leu Lys Phe His Phe
1               5

<210> SEQ ID NO 198
<211> LENGTH: 6
<212> TYPE: PRT
<213> ORGANISM: Artificial Sequence
<220> FEATURE:
<223> OTHER INFORMATION: Synthesized

<400> SEQUENCE: 198

Phe Arg Leu Lys His Ile
1               5

<210> SEQ ID NO 199
<211> LENGTH: 5
<212> TYPE: PRT
<213> ORGANISM: Artificial Sequence
<220> FEATURE:
<223> OTHER INFORMATION: Synthesized

<400> SEQUENCE: 199

Phe Arg Leu His Phe
1               5

<210> SEQ ID NO 200
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: X = any amino acid

<400> SEQUENCE: 200

Phe Arg Xaa Xaa Xaa Xaa
1               5

<210> SEQ ID NO 201
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: X = any amino acid

<400> SEQUENCE: 201

Phe Arg Leu Xaa Xaa Xaa
1               5
```

```
-continued

<210> SEQ ID NO 202
<211> LENGTH: 6
<212> TYPE: PRT
<213> ORGANISM: Artificial Sequence
<220> FEATURE:
<223> OTHER INFORMATION: Synthesized

<400> SEQUENCE: 202

His Phe Lys Leu Arg Phe
1               5

<210> SEQ ID NO 203
<211> LENGTH: 5
<212> TYPE: PRT
<213> ORGANISM: Artificial Sequence
<220> FEATURE:
<223> OTHER INFORMATION: Synthesized

<400> SEQUENCE: 203

Phe Arg Leu His Phe
1               5
```

ANTIFUNGAL PAINTS AND COATINGS

CROSS-REFERENCE TO RELATED APPLICATIONS

The present application is a divisional application from prior U.S. patent application Ser. No. 10/884,355 filed Jul. 2, 2004 which claims priority to U.S. Provisional Application No. 60/485,234 filed Jul. 3, 2003.

BACKGROUND OF THE INVENTION

1. Field of the Invention

The present invention generally relates to antifungal and antibacterial compositions and methods employing such compositions to deter or prevent fungal growth in stored coatings and on susceptible surfaces. More particularly, the present invention relates to such compositions containing antifungal and antibacterial peptides, polypeptides or proteins and to methods of making and using such compositions.

2. Description of the Related Art

Fungal growth on indoor and outdoor surfaces is a major environmental concern today affecting home, work and recreational environments. Not only can fungus (e.g., mold, mildew) be unsightly on exposed surfaces, it can destroy wood, fiber and other materials if left untreated, causing severe damage to buildings and other structures and equipment. Over the past few years it has become increasingly apparent that exposure to certain fungi or their spores can seriously impact the health of humans, pets and other animals. Although fungi are certainly not the only factors that detrimentally affect indoor air quality, in many instances they have been identified as a primary contributor to indoor air quality problems. In fact, the term "sick building syndrome" was recently coined to describe buildings in which various physical, chemical and biological factors, including growing fungi and/or their spores, have severely compromised the air quality leading to discomfort or illness of the occupants. Concerns such as allergies, asthma, infections, and the long-term repercussions of mold toxins are just a few of the many real health effects associated with mold contamination of indoor and outdoor environments.

Fungi (including true fungi, molds and mildews) are eukaryotic organisms that have cell walls, similar to plants, but do not contain chlorophyll. There are between 100,000-200,000 species of fungi, mold and mildew, depending on which classification methods are used. Of particular concern are the pathogenic fungi, which can cause significant harm to individuals who are exposed to them. About 300 species are presently known to be pathogenic for man, but it is thought that there are many other as yet unrecognized fungal pathogens. The field of medical mycology has emerged as a result of the growing number of fungal-related illnesses and deaths.

Fungi grow as saprophytes, i.e., in a suitable moist environment they are able to decompose organic matter to obtain the nourishment needed for growth. Building and decorative materials such as wood, paper-coated wallboard, wallpaper, fabrics, carpet and leather can provide the necessary organic matter. Today, an especially problematic fungal genus sometimes found in buildings that have excess indoor moisture is *Stachybotrys*, *Stachybotrys chartarum*, commonly found in nature growing on cellulose-rich plant materials, has often been found in water-damaged building materials, such as ceiling tiles, wallpaper, Sheetrock® and cellulose resin wallboard (fiberboard). Depending on the particular conditions of temperature, pH and humidity in which the mold is growing, *Stachybotrys* may produce mycotoxins, compounds that have toxic properties.

Other common fungi that can grow in residential and commercial buildings are *Aspergillus* species (sp.), *Penicillium* sp., *Fusarium* sp., *Alternaria dianthicola*, *Aureobasidium pullulans* (aka *Pullularia pullulans*), *Phoma pigmentivora* and *Cladosporium* sp. The moist indoor environment which promotes growth of these fungi can arise from water damage, excessive humidity, water leaks, condensation, water infiltration, or flooding, in some cases due to defects in building construction, faulty mechanical system design, and/or operational problems. Even modern homes and commercial buildings are not immune to fungal invasion despite the use of technologically advanced building materials and more energy efficient construction and operation than in buildings of the past. Modern homes tend to be less well ventilated, and although the use of air conditioning reduces humidity making it harder for mold to grow, today's central air conditioning systems can also facilitate the spread of mold spores throughout a home. Increased use of paper products in homes and commercial buildings today further encourages mold growth. Heavy contamination of indoor or outdoor surfaces by dirt and/or oil can also provide a food source for a fungus. Vulnerable structures and materials that are difficult to access for cleaning, or for which cleaning is neglected, are particularly vulnerable to attack by fungi. Fungi are also known to contaminate stored paints, fuels, and many other industrial products.

Fungal colonies typically take on filamentous form, having long filament-like cells called hyphae. Under the right environmental conditions, hyphae grow into an intertwining network called the mycelium. A mycelium can be visible to the naked eye, appearing as unsightly fuzzy green, bluish-gray or black spots, for example. When conditions for growth are less favorable, many varieties of fungi can respond by forming spores on specialized hyphal cells. Spores are the primary means for dispersal and survival of fungi, and can remain dormant for months or even years—even withstanding extremely adverse conditions, to germinate and flourish again when environmental variables such as light, oxygen levels, temperature, and nutrient availability again become favorable. Thick-walled spores are substantially more resistant to common disinfective agents than are the thinner-walled vegetative fungal cells. According to the U.S. Environmental Protection Agency, there is no practical way to eliminate all mold and mold spores in the indoor environment.

As mentioned above, paints and paint films or coatings are known to be vulnerable to mold contamination due to the presence of common organic components that act as cellulosic thickeners, surfactants and defoamers, and which can also serve as a source of food for fungus cells. Some of these components are casein, acrylic, polyvinyl and other carbon polymers. For example, latex is a water-dispersed binder comprising a carbon polymer. Inside the paint can, certain fungi (e.g., yeasts) can convert enough carbon-containing food sources to $CO_2$ to swell or even explode the can. Fungi can also discolor and reduce the viscosity of the paint, and produce foul odors. Both in-can preservation of paints and protection of the end use paint films, and the surfaces they cover, from mold, mildew and yeasts is necessary. To combat fungi, a variety of coating materials have been formulated which include organic or inorganic chemicals to discourage or prevent the growth of mildew on the paint film. Ideally, these chemical fungicides or mildewcides slowly leach out of the paint to the surface, and maintain their inhibitory properties for the life of the paint film, causing little or no harm to the environment. In practice, however, the antifungal properties of most coating compositions in use today persist for variable lengths of time, depending on the amount of exposure to the elements, abrasion and erosion.

Most antifungal chemicals are non-specific as to the organism affected and can be detrimental to the environment, including toxicity to plant and animal life. It is more difficult to identify fungus-specific agents than it is to discover bacteria specific-agents because fungal cells share many similarities with the cells of higher organisms, whereas bacterial cells are distinctly different. For this reason, fungicides tend to be more toxic to humans and animals than are bactericides. U.S. Pat. No. 5,882,731 (Owens) describes a number of common and proprietary chemical mildewcide-containing products that have been investigated as additives for water-based latex mixtures. Some known antifungal agents that have been used in the coatings industry are: copper (II) 8-quinolinolate (CAS No. 10380-28-6); zinc oxide (CAS No. 1314-13-2); zinc-dimethyl dithiocarbamate (CAS No. 137-30-4); 2-mercapto-benzothiazole, zinc salt (CAS No. 155-04-4); barium metaborate (CAS No. 13701-59-2); tributyl tin benzoate (CAS No. 4342-36-3); bis tributyl tin salicylate (CAS No. 22330-14-9), tributyl tin oxide (CAS No. 56-35-9); parabens: ethyl parahydroxybenzoate (CAS No. 120-47-8), propyl parahydroxybenzoate (CAS No. 94-13-3) methyl parahydroxybenzoate (CAS No. 99-76-3) and butyl parahydroxybenzoate (CAS No. 94-26-8); methylenebis(thiocyanate) (CAS No. 6317-18-6); 1,2-benzisothiazoline-3-one (CAS No. 2634-33-5); 2-mercaptobenzo-thiazole (CAS No. 149-30-4); 5-chloro-2-methyl-3(2H)-isothiazolone (CAS No. 57373-19-0); 2-methyl-3(2H)-isothiazolone (CAS No. 57373-20-3); zinc 2-pyridinethiol-N-oxide (CAS No. 13463-41-7); tetra-hydro-3,5-di-methyl-2H-1,3,5-thiadiazine-2-thione (CAS No. 533-74-4); N-trichloromethyl-thio-4-cyclo-hexene-1,2-dicarboximide (CAS No. 133-06-2); 2-n-octyl-4-isothiazoline-3-one (CAS No. 26530-20-1); 2,4,5,6-tetrachloro-isophthalonitrile (CAS No. 1897-45-6); 3-iodo-2-propynyl butylcarbamate (CAS No. 55406-53-6); diiodomethyl-p-tolylsulfone (CAS No. 20018-09-1); N-(trichloromethyl-thio)phthalimide (CAS No. 133-07-3); potassium N-hydroxy-methyl-N-methyl-dithiocarbamate (CAS No. 51026-28-9); sodium 2-pyridinethiol-1-oxide (CAS No. 15922-78-8); 2-(thiocyanomethylthio) benzothiazole (CAS No. 21564-17-0); 2-4(-thiazolyl)benzimidazole (CAS No. 148-79-8). See V. M. King, "Bactericides, Fungicides, and Algicides," Ch. 29, pp. 261-267; and D. L. Campbell, "Biological Deterioration of Paint Films," Ch. 54, pp. 654-661; both in PAINT AND COATING TESTING MANUAL, 14$^{th}$ ed. of the Gardner-Sward Handbook, J. V. Koleske, Editor (1995), American Society for Testing and Materials, Ann Arbor, Mich. Currently, the Pesticide Action Network North America (PAN) lists in its Internet chemical database, www-.panna.org, the above-mentioned chemicals plus more than 700 additional chemicals designated as pesticides having antifungal properties in soil and wood.

The mode of action of some of the metal-based antifungal agents is thought to be chelation of metals that are necessary to growth of the organisms. Some of the nitrogen- and/or sulfur-containing antifungal agents are thought to act by uncoupling oxidative phosphorylation in the fungal cells, or inhibiting oxidation of glucose. The paraben compounds (aka hydroxybenzoate) are thought to affect membrane activity and integrity.

Due to environmental and safety concerns, there is increasing pressure today on the coatings industry to eliminate some of the more effective but more toxic chemical preservatives from paints and other coating compositions. Yet at the same time, consumers wish to avoid purchasing spoiled or poorly performing products. Thus, there is a great need in the industry today for safe and effective alternatives to conventional antifungal agents.

Various naturally occurring biological products that are said to possess antifungal activity are described in the background discussion of U.S. Pat. Nos. 6,020,312; 5,602,097; and 5,885,782 [each incorporated in their entirety by reference herein]. In many cases, the active component of those natural antifungal agents has not been identified nor completely characterized. Since most of the known naturally occurring antifungal agents are poorly characterized at best, the persistence and toxicity of such compounds in the environment is also unknown. Furthermore, the fact that many of those compounds are produced by microbes in the environment suggests that they may have a limited spectrum of antifungal activity. A drawback of most of the antifungal agents in use today is that they are as toxic to higher organisms as they are to the target fungi. The more target-specific antifungal agents tend to be very rare and/or costly.

Recently developed methods permit the preparation of synthetic peptide combinational libraries ("SPCLs") that are composed of equimolar mixtures of free peptides that can be used with in vitro methods to determine bioactivity (Furka, A., et al. Int. J. Pept. Protein Res. 37:487 (1991), Houghten, R. A., et al. Nature 354:84 (1991), Houghten, R. A., et al. BioTechniques 13:412 (1992). Libraries can consist of D- or L-amino acid stereoisomers or combinations of L- and D- and/or non-naturally-occurring amino acids. Other methods for synthesizing peptides of defined sequence are also known. Similarly, large-scale preparative methods are known. Certain recombinant methods for producing peptides have also been described, e.g., U.S. Pat. No. 4,935,351. While U.S. Pat. Nos. 6,020,312; 5,602,097; and 5,885,782 describe agricultural uses for certain synthetic antifungal peptides, none of those or any other peptidic agents have been previously investigated as additives for use in the paints and coatings industry.

Although significant advancement has been made in identifying various chemical agents and natural and synthetic peptides or proteins that demonstrate antifungal activity for certain uses (e.g., medical treatment or agricultural use), there is no indication that any such biomolecule could be used successfully in paints or other coating materials for protecting or treating non-living objects. Antifungal or fungus-resistant paints and other coating compositions are needed which do not suffer from the same limitations as conventional surface coating materials containing existing fungicides and antifungal agents. Ideally, an antifungal paint will contain fungus-specific fungus deterring/inhibiting/killing agents that are stable in paints and other coating mixtures during storage, persist in the resulting coat or film that is spread out over a surface in need of protection from fungal infestation, and which are safer to the environment. Better antifungal materials would be especially welcomed by original equipment manufacturers (OEMs), and by the architectural, marine and industrial maintenance industries. In particular, antifungal and antibacterial additives to paints and coatings that work alone or synergistically with existing antifungal agents would be desirable.

BRIEF SUMMARY OF THE INVENTION

The compositions and methods of the present invention overcome some of the disadvantages of previous antifungal or fungus-resistant paints, coatings and other compositions such as elastomers, textile finishes, adhesives, and sealants. It was not previously known to combine a natural, synthetic or recombinant antifungal peptide, polypeptide or peptide with a paint or other coating material to provide a coated surface with sustainable antifungal activity that protects the recipient surface from fungal infestation and defacement, and which also provides fungus resistance to the composition itself. It is now disclosed that antifungal peptidic agents offer a new tool in the arsenal of fungicidal and fungistatic chemicals. Accordingly, new antifungal and antibacterial paints, coatings, films and other compositions are provided which contain one or more bioactive peptides, polypeptides and/or proteins as antifungal and antibacterial peptidic agents. Methods of using the antifungal and antibacterial additives and compositions for treating existing fungal or bacterial colonies and/or for deterring or preventing fungal or bacterial infestations and inhibiting cell growth or proliferation on a variety of inanimate objects such as interior and exterior architectural surfaces and building materials are also provided. The compositions and methods disclosed herein avoid many of the drawbacks of existing methods and compositions which rely on non-specific chemical bacteriocides, fungicides, or antifungal agents. By application of a protective coating comprising one or more antifungal or antibacterial protein, polypeptide or peptide, one can prevent or deter or lessen the infestation and growth of fungus or bacterium. At the same time, the associated discoloration, disfiguration and/or degradation of the supporting substrate or surface can be avoided or reduced. The compositions of the invention are especially useful on surfaces where conditions are conducive to deposition and development of fungus or bacteria, and where control of fungal or bacterial growth is preferably accomplished with compositions which are not toxic to humans, pets and other animals or harmful to the environment.

In accordance with certain embodiments of the invention, an antifungal coating composition is provided that is effective for inhibiting the growth of *Stachybotrys* fungi. In some embodiments, an antifungal coating composition is provided that is effective for inhibiting the growth of one or more of the *Aspergillus, Penicillium, Fusarium, Alternaria,* and *Cladosporium* genera of fungi. In some embodiments, an antifungal coating composition is effective for inhibiting the growth of *Rhizoctonia, Ceratocystis, Pythium, Mycosphaerella,* and *Candida* genera of fungi. In certain instances, a coating is provided that is either antifungal, antibacterial, or both antifungal and antibacterial.

In certain embodiments of the present invention, compositions are formulated for use as paints and the like, for coating surfaces. In certain embodiments, such coating includes impregnating porous or semi-porous materials that are capable of supporting fungal growth. These compositions contain various antifungal peptides or proteins, as described herein, and may also contain chemicals and other substances that are conventional and well known in the art. One of the important benefits of certain preferred embodiments of the present invention is that little or no formulation modification, other than the inclusion of the presently described antifungal peptide component, is needed to obtain substantial enhancement of fungus resistant, antifungal or fungicidal properties of the coating composition.

A further embodiment comprises using a film or coat comprising the coating composition, or the composition itself, to protect an object or material selected from the group consisting of wood, paint, adhesive, glue, paper, textile, leather, plastic, cardboard, caulking, from infestation and growth of a fungus.

A preferred coating material comprises a paint or coating. In some embodiments the paint or coating is applied prophylactically over a "clean" surface that is not contaminated by fungal spores. In other embodiments the paint or coating is applied to a surface already contaminated by fungal spores or growing fungus.

In certain embodiments of the present invention, a paint or other surface-coating composition is provided that contains an antifungal protein, polypeptide or peptide additive that retains its antifungal activity after being admixed with said paint or other surface-coating composition, and retains antifungal activity after the paint or surface-coating composition is applied to a surface. Even after drying, the paint or other surface-coating composition renders the coated surface antifungal. More specifically, an antifungal paint or other surface-coating composition comprising antifungal protein, polypeptide or peptide additive is capable of biologically interacting with a susceptible fungus cell or spore in a manner that inhibits or prevents growth of the fungus, preferably for extended periods of time. Some additives of the present invention remained stable in the coating for an extended period of time (e.g., months) at ambient conditions. It is contemplated that with certain antifungal compositions, especially those containing microencapsulated antifungal peptides, the extended period of activity may comprise years. In a preferred embodiment, a polymer-based compound that prophalactically and continuously deters fungal infestation, inhibits or kills fungal cells is provided.

It is contemplated that in certain embodiments the compositions and methods of the present invention may be used to produce a fungal cell growth inhibitory surface, or a fungal cell killing surface, that remains active for extended periods. Such an antifungal surface may not need additional treatment with fungicide compositions, clean-up treatments to effect decontamination and cosmetic painting, thereby simplifying upkeep of the physical condition and appearance of fungus infestation prone surfaces such as building exteriors. It is contemplated that in some embodiments the compositions of the present invention may be easily applied to susceptible surfaces in advance of and/or during exposure to a fungus organism.

Isolated naturally occurring proteins, polypeptides and/or peptides are employed in some embodiments, and in preferred embodiments synthetic proteins, polypeptides and/or peptides are employed. In some embodiments, combinations of natural and/or synthetic proteins, polypeptides and peptides are employed. Still other embodiments employ at least one recombinant protein, polypeptide and/or peptide that is produced using specific expression vectors in a variety of host cells.

Antifungal peptides are chemically defined species that are easily synthesized and purified. They are not necessarily dependent upon the genetic stability or growth properties of microorganisms for their production. The methods and compositions of the present invention employ an array of different antibiotic compounds which are shown to have particular effectiveness in inhibiting the growth of or killing fungal cells. The compositions of the invention are effective in controlling the growth of fungi, and yet demonstrate a high degree of specificity to the target fungi, low toxicity and controlled persistence in the environment. Using the preferred methods it is possible to produce and identify desirable antifungal agents for use in paints and coatings in a much shorter time, and with a considerably higher-probability of success, than screening natural isolates for antifungal peptides. Since the preferred methods of production can control the chemical nature of the antifungal agents thus produced, synthesis and purification (if needed) of the peptides is much less problematic (e.g., cysteine is eliminated, which amino acid's free sulfhydryl groups can cause unwanted cross linking). Thus, in some embodiments, the paint compositions of the present invention comprise peptides of precisely known chemical structure and characteristics. The use of D-amino acids increases the stability of certain of these compounds by being insensitive to common biological degradation pathways that degrade L-amino acid peptides. For instance, L-amino acid peptides may be stabilized by addition of D-amino acids at one or both of the peptide termini. However, biochemical pathways are available which will degrade even D-amino acids in these peptides so that long-term environmental persistence is not a problem. Of course, where the compositions of the invention act rapidly or need not otherwise be stabilized, L-amino acids or mixtures of L- and D-amino acids may be useful. Unlike antifungal agents which only work as one or another stereoisomer, the compositions of the invention work well as either one or another stereoisomer or as a mixed stereoisomeric composition. Research leading to the current invention evaluated SPCLs for activity against fungal pathogens, including pathogens of plants as well as those of animals. The library was composed of 52,128,400 six-residue peptides, each peptide being composed of D-amino acids and having non-acetylated N-termini and amidated C-termini. However, it is not necessary for a peptide composition of demonstrable antibiotic activity to be completely defined as to each residue. In fact, in certain instances, especially where the peptide compositions of the invention are being used to treat an array of fungal target organisms each with a different causative agent, mixed peptide compositions will be preferred. This is also likely to be the case where there is a desire to treat a fungal target with lower concentrations of numerous antifungal additives rather than a higher concentration of a single chemical composition. In other instances where, for instance, due to the increased cost of testing or producing a completely defined peptide antibiotic is prohibitive, the mixed peptide compositions of the invention having one or more variable amino acid residues may be preferred. In other instances, it may be possible to use peptide antibiotic compositions in coatings that have not been purified, that have not had their side chains de-blocked, and/or have not been cleared from the synthetic resin used to anchor the growing amino acid chains. Thus, antibiotic compositions comprising equimolar mixture of peptides produced in a synthetic peptide combinatorial library utilizing the methods of the invention have been derived and shown to have desirable antibiotic activity. In certain embodiments, these relatively variable compositions are specifically those based upon the sequences of one or more of the peptides disclosed in any of the U.S. Pat. Nos. 6,020,312; 5,602,097; and 5,885,782.

The antibiotic compositions of the invention may also comprise a carrier. In certain instances, the carrier will be one suitable for permanent surface coating applications. In other instances, the carrier will be one suitable for use in applying the antibiotic compositions in semi-permanent or temporary coatings. In either instance, the carrier selected should preferably be a carrier whose chemical and/or physical characteristics do not significantly interfere with the antibiotic activity of the peptide composition. It is known, for instance that certain microsphere carriers may be effectively utilized with proteinaceous compositions in order to deliver these compositions to a site of preferred activity such as onto a surface. Liposomes may be similarly utilized to deliver labile antibiotics. Saline solutions, coating-acceptable buffers and solvents and the like may also be utilized as carriers for the peptide compositions of the invention. Those peptides have been demonstrated to inhibit the growth of fungal cells from at least the *Fusarium, Rhizoctonia, Ceratocystis, Pythium,* *Mycosphaerella* and *Candida* species, and are believed to be active against additional genera, including at least some of those that are capable of infesting building materials and other inanimate objects.

Similarly, processes for inhibiting growth of fungal cells comprise contacting the fungal cell with a paint or coating composition comprising at least one peptide. Using the techniques of the invention, selected pathogenic fungi, some pathogens of plants and others pathogens of animals, have been tested. The processes of the invention have, therefore, been specifically shown to be effective where the fungal cell is a fungal cell selected from the group of fungi consisting of *Fusarium* and *Aspergillus*. The processes of the invention are applied to fungal cells of a pathogen of an animal, such as a human. A method for selecting antibiotic compositions is also described. The method comprises first creating a synthetic peptide combinatorial library as described herein. Next, as further described in detail herein, a step of contacting a battery of fungal cells with aliquots of the synthetic peptide combinatorial library, each of which aliquots represents an equimolar mixture of peptides in which at least the two C-terminal amino acid residues are known and which residues are in common for each peptide in said mixture is accomplished. After allowing an appropriate period for growth, a next step is accomplished in which the growth of the battery of fungal cells as compared to untreated control cells is measured. Lastly, a determination is made of which of the aliquots most reduces the growth of fungal cells in a coating overall in the battery of fungal cells. Of course, the same method may be carried out in which each of the aliquots represents an equimolar mixture of peptides in which at least three, four, five or more C-terminal amino acid residues are known (depending upon the overall length of the ultimate peptide in the SPCL). Typically, such increasingly defined aliquots will be sequentially tested in order to select the succeeding best candidate peptides for testing. Thus, an additional step in the method entails utilizing the determination of which of the aliquots reduces the growth of fungal cells in a coating overall in said battery of fungal cells to select which aliquots to next test of a synthetic peptide combinatorial library where at least one additional C-terminal amino acid residue is known.

A method of treating or preventing growth of a fungus on a susceptible surface is also disclosed. These and other objects, features and advantages of the present invention will be readily apparent to one skilled in the art from the following detailed description and claims.

DETAILED DESCRIPTION OF THE PREFERRED EMBODIMENTS

The following detailed description, specific examples and claims, while indicating the preferred embodiments of the invention, are given by way of illustration only and are considered representative of other embodiments. Accordingly, it will be readily apparent to one skilled in the art from this detailed description and the claims which follow that various changes, substitutions and modifications may be made to the invention disclosed herein without departing from the scope and spirit of the invention.

Paints and other conventional protective or decorative coating materials typically contain polymeric substances such as casein, acrylic, polyvinyl and carbon polymers (e.g., binders) which can serve as nutrients for fungal cells. As discussed above in the Background of the Invention, not only can these nutrient substances support the growth of fungus on paint films or coated surfaces, fungus can also grow inside cans of liquid paints and coating compositions during storage. It was, therefore, an unexpected discovery that certain synthetic peptides, when added to a range of conventional paint and coating materials, render those compositions resistant to fungal infestation and growth. It was also surprising to find that such additives worked alone or in conjunction with existing biocides in a coating.

Example 1

Antifungal Peptide Additives for a Coating Composition

A group of preferred antifungal peptides that have either demonstrated activity as additives for coating mixtures, or that are expected to demonstrate such activity, are disclosed in U.S. Pat. No. 6,020,312 (Edwards); U.S. Pat. No. 5,885,782 (Edwards); and U.S. Pat. No. 5,602,097 (Edwards), the disclosures of which are hereby incorporated in their entirety herein by reference. Preferred sequences that will be employed include one or more of SEQ ID Nos. 1-47, preferably SEQ ID Nos. 25-47. These and other peptides with antifungal activity are identified using methods and testing protocols like those described in the above-referenced patents. Additional peptides that are expected to demonstrate the desired activity in coatings are listed in Table I. The screening method generally includes:

(a) creating a synthetic peptide combinatorial library using known methods and materials;

(b) testing a battery of fungal cells that are known to, or suspected of, infesting a building material or other object having a fungus-infestation susceptible surface with aliquots of the synthetic peptide library, wherein each aliquot comprises an equimolar mixture of peptides in which at least one of the C-terminal amino acid residues are known and which residues are in common for each peptide in the mixture;

(c) admixing said aliquots with a coating typically used on such building material and coating a surface with the admixture;

(d) allowing an appropriate period of time for growth of the fungal cell under suitable culture conditions;

(e) comparing the growth of the treated fungal cells with untreated control cells;

(f) identifying which of the aliquots reduced the growth of the fungal cells; and, optionally, assessing the relative growth inhibitory activity of each aliquot compared to that of other aliquots (e.g., comparing $IC_{50}$ data).

TABLE 1

| Name | Source | Seq. ID | Activity | Reference |
|------|--------|---------|----------|-----------|
|  | Synthetic | 1 | Fungi | U.S. Pat. No. 5,885,782 |
|  | Synthetic | 2 | Fungi | U.S. Pat. No. 5,885,782 |
|  | Synthetic | 3 | Fungi | U.S. Pat. No. 5,885,782 |
|  | Synthetic | 4 | Fungi | U.S. Pat. No. 5,885,782 |
|  | Synthetic | 5 | Fungi | U.S. Pat. No. 5,885,782 |
|  | Synthetic | 6 | Fungi | U.S. Pat. No. 5,885,782 |
|  | Synthetic | 7 | Fungi | U.S. Pat. No. 5,885,782 |
|  | Synthetic | 8 | Fungi | U.S. Pat. No. 5,885,782 |
|  | Synthetic | 9 | Fungi | U.S. Pat. No. 5,885,782 |
|  | Synthetic | 10 | Fungi | U.S. Pat. No. 5,885,782 |
|  | Synthetic | 11 | Fungi | U.S. Pat. No. 5,885,782 |
|  | Synthetic | 12 | Fungi | U.S. Pat. No. 5,885,782 |
|  | Synthetic | 13 | Fungi | U.S. Pat. No. 5,885,782 |
|  | Synthetic | 14 | Fungi | U.S. Pat. No. 5,885,782 |
|  | Synthetic | 15 | Fungi | U.S. Pat. No. 5,885,782 |
|  | Synthetic | 16 | Fungi | U.S. Pat. No. 5,885,782 |
|  | Synthetic | 17 | Fungi | U.S. Pat. No. 5,885,782 |
|  | Synthetic | 18 | Fungi | U.S. Pat. No. 5,885,782 |
|  | Synthetic | 19 | Fungi | U.S. Pat. No. 5,885,782 |
|  | Synthetic | 20 | Fungi | U.S. Pat. No. 5,885,782 |
|  | Synthetic | 21 | Fungi | U.S. Pat. No. 5,885,782 |
|  | Synthetic | 22 | Fungi | U.S. Pat. No. 5,885,782 |
|  | Synthetic | 23 | Fungi | U.S. Pat. No. 5,885,782 |
|  | Synthetic | 24 | Fungi | U.S. Pat. No. 5,885,782 |
|  | Synthetic | 25 | Fungi | U.S. Pat. No. 5,885,782 |
|  | Synthetic | 26 | Fungi | U.S. Pat. No. 5,885,782 |
|  | Synthetic | 27 | Fungi | U.S. Pat. No. 5,885,782 |
|  | Synthetic | 28 | Fungi | U.S. Pat. No. 5,885,782 |
|  | Synthetic | 29 | Fungi | U.S. Pat. No. 5,885,782 |
|  | Synthetic | 30 | Fungi | U.S. Pat. No. 5,885,782 |
|  | Synthetic | 31 | Fungi | U.S. Pat. No. 5,885,782 |
|  | Synthetic | 32 | Fungi | U.S. Pat. No. 5,885,782 |
|  | Synthetic | 33 | Fungi | U.S. Pat. No. 5,885,782 |
|  | Synthetic | 34 | Fungi | U.S. Pat. No. 5,885,782 |
|  | Synthetic | 35 | Fungi | U.S. Pat. No. 5,885,782 |
|  | Synthetic | 36 | Fungi | U.S. Pat. No. 5,885,782 |
|  | Synthetic | 37 | Fungi | U.S. Pat. No. 5,885,782 |
|  | Synthetic | 38 | Fungi | U.S. Pat. No. 5,885,782 |
|  | Synthetic | 39 | Fungi | U.S. Pat. No. 5,885,782 |
|  | Synthetic | 40 | Fungi | U.S. Pat. No. 5,885,782 |
|  | Synthetic | 41 | Fungi | U.S. Pat. No. 5,885,782 |
|  | Synthetic | 42 | Fungi | U.S. Pat. No. 5,885,782 |
|  | Synthetic | 43 | Fungi | U.S. Pat. No. 5,885,782 |
|  | Synthetic | 44 | Fungi | U.S. Pat. No. 5,885,782 |
|  | Synthetic | 45 | Fungi | U.S. Pat. No. 5,885,782 |

TABLE 1-continued

| Name | Source | Seq. ID | Activity | Reference |
|---|---|---|---|---|
| | Synthetic | 46 | Fungi | U.S. Pat. No. 5,885,782 |
| | Synthetic | 47 | Fungi | U.S. Pat. No. 5,885,782 |
| Tachystatin A | Horseshoe Crab | 48 | Gram+ & Gram−, Fungi | Fujitani (2002) |
| Androctonin | *Androctonus Australis* | 49 | Gram+ & Gram−, Fungi | Mandard (1999) |
| Tritrpticin | Synthetic | 50 | Gram+ & Gram−, Fungi | Schibli (1999) |
| HNP-3 Defensin | Human | 51 | Gram+ & Gram−, Virus, Fungi | Hill (1991) |
| Anti-fungal protein 1 (pafp-s) | *Phytolacca Americana* | 52 | Fungi | Gao (2001) |
| Magainin 2 | Synthetic construct | 53 | Gram+ & Gram−, Fungi | Hara (2001) |
| Indolicidin | *Bos Taurus* | 54 | Gram+ & Gram−, Virus, Fungi | Rozek (2000) |
| Defensin heliomicin | *Heliothis virescens* | 55 | Fungi | Lamberty (2001) |
| Defensin heliomicin | *Heliothis virescens* | 56 | Gram+ & Gram−, Fungi | Lamberty (2001) |
| Sativum defensin 1 (psd1) | Seed of Pea | 57 | Fungi | Almeida (2002) |
| Gomesin | Synthetic | 58 | Gram+ & Gram−, Fungi, Mammalian cells | Mandard (2002) |
| Lactoferricin B | Bovine | 59 | Gram+ & Gram−, Virus, Fungi, Cancer cells | Hwang (1998) |
| PW2 | Synthetic | 60 | Fungi | Tinoco (2002) |
| Hepcidin 20 | Human | 61 | Fungi | Hunter (2002) |
| Hepcidin 25 | Human | 62 | Fungi | Hunter (2002) |
| AC-AMP2 | *Amaranthus caudatus* | 63 | Gram+, Fungi | Martins (1996) |
| NK-Lysin | *Sus scrofa* | 64 | Gram+ & Gram−, Fungi | Liepinsh (1997) |
| Magainin 2 | African clawed frog | 65 | Gram+ & Gram−, Fungi, cancer cells | Gesell (1997) |
| Melittin B | Honey bee venom | 66 | Gram+ & Gram−, Fungi, Mammalian cells | Eisenberg |
| Thanatin | *Podisus maculiventris* | 67 | Gram+ & Gram−, Fungi | Mandard (1998) |
| Antimicrobial peptide 1 | Common ice plant | 68 | Gram+ & Gram−, Fungi | Michalowski (1998) |
| Melanotropin alpha (Alpha-MSH) | Bovine | 69 | Gram +, Fungi | Cutuli (2000) |
| CORTICOSTATIN III (MCP-1) | Rabbit | 70 | Gram+ & Gram−, Virus, Fungi | Selsted (1988) |
| CORTICOSTATIN III (MCP-1) | Rabbit | 71 | Gram+ & Gram−, Virus, Fungi | Selsted (1988) |
| Cecropin B | Chinese oak silk moth | 72 | Gram+ & Gram−, Fungi | Qu (1982) |
| Seminalplasmin | Bovine | 73 | Gram+ & Gram−, Fungi, Mammalian cells | Theil (1983) |
| NP-3A defensin | Rabbit | 74 | Gram+ & Gram−, Virus, Fungi | Zhu (1992) |
| HNP-1 Defensin | Human | 75 | Gram+ & Gram−, Virus, Fungi | Zhang (1992) |
| HNP-2 Defensin | Human | 76 | Gram+ & Gram−, Virus, Fungi | Selsted (1989) |
| HNP-4 Defensin | Human | 77 | Gram+ & Gram−, Fungi | Wilde (1989) |
| Histatin 5 | Human | 78 | Gram+ & Gram−, Fungi | Raj (1998) |
| Histatin 3 | Human | 79 | Gram+ & Gram−, Fungi | Oppenheim (1988) |
| Histatin 8 | Human | 80 | Gram+ & Gram−, Fungi | Yin (2003) |
| Tracheal antimicrobial peptide | Bovine | 81 | Gram+ & Gram−, Fungi | Zimmermann (1995) |
| AMP1 (MJ-AMP1) | Garden four-o'clock | 82 | Gram+, Fungi | Cammue (1992) |
| AMP2 (MJ-AMP2) | Garden four-o'clock | 83 | Gram+, Fungi | Cammue (1992) |

TABLE 1-continued

| Name | Source | Seq. ID | Activity | Reference |
|---|---|---|---|---|
| MBP-1 | Maize | 84 | Gram+ & Gram−, Fungi | Duvick (1992) |
| AFP2 | Rape | 85 | Fungi | Terras (1993) |
| AFP1 | Turnip | 86 | Fungi | Terras (1993) |
| AFP2 | Turnip | 87 | Fungi | Terras (1993) |
| ADENOREGULIN | Two coloured leaf frong | 88 | Gram+ & Gram−, Fungi | Mor (1994) |
| Protegrin 2 | Pig | 89 | Gram+ & Gram−, Virus, Fungi | Kokryakov (1993) |
| Protegrin 3 | Pig | 90 | Gram+ & Gram−, Virus, Fungi | Kokryakov (1993) |
| Histatin 1 | Crab eating macaque | 91 | Gram+ & Gram−, Fungi | Xu (1990) |
| Peptide PGQ | African clawed frog | 92 | Gram+ & Gram−, Fungi | Moore (1991) |
| Ranalexin | Bull frog | 93 | Gram+ & Gram−, Fungi | Halverson (2000) |
| GNCP-2 | Guinea pig | 94 | Gram+ & Gram−, Virus, Fungi | Nagaoka (1991) |
| Protegrin 4 | Pig | 95 | Gram+ & Gram−, Virus, Fungi | Zhao (1994) |
| Protegrin 5 | Pig | 96 | Gram+ & Gram−, Virus, Fungi | Zhao (1995) |
| BMAP-27 | Bovine | 97 | Gram+ & Gram−, Fungi | Skerlavaj (1996) |
| BMAP-28 | Bovine | 98 | Gram+ & Gram−, Fungi | Skerlavaj (1996) |
| Buforin I | Asian toad | 99 | Gram+ & Gram−, Fungi | Park (1996) |
| Buforin II | Asian toad | 100 | Gram+ & Gram−, Fungi | Yi (1996) |
| BMAP-34 | Bovine | 101 | Gram+ & Gram−, Fungi | Scocchi (1997) |
| Tricholongin | *Trichoderma longibrachiatum* | 102 | Gram+ & Gram−, Fungi | Rebuffat (1991) |
| Dermaseptin 1 | Sauvage's leaf frog | 103 | Gram+ & Gram−, Fungi | Mor (1994) |
| Pseudo-hevein (Minor hevin) | Para rubber tree | 104 | Fungi | Soedjanaatmadja (1994) |
| Gaegurin-1 | Wrinkled frog | 105 | Gram+ & Gram−, Fungi | Park (1994) |
| Skin peptide tyrosine-tyrosine | Two-colored leaf frog | 106 | Gram+ & Gram−, Fungi | Mor (1994) |
| Penaeidin-1 | Penoeid shrimp | 107 | Gram+ & Gram−, Fungi | Destoumieux (2000) |
| Neutrophil defensin 1 (HANP-1) | Golden hamster | 108 | Gram+, Fungi | Mak (1996) |
| Neutrophil defensin 3 (HANP-3) | Golden hamster | 109 | Gram+, Fungi | Mak (1996) |
| Misgurin | Oriental weatherfish | 110 | Gram+ & Gram−, Fungi | Park (1997) |
| PN-AMP | Japenese morning glory | 111 | Gram+, Fungi | Koo (1998) |
| Histone H2B-1 (HLP-1) (Fragment) | Rainbow trout | 112 | Gram+ & Gram−, Fungi | Robinette (1998) |
| Histone H2b-3 (HLP-3) (Fragment) | Rainbow trout | 113 | Fungi | Robinette (1998) |
| Neutrophil defensin 2 (RMAD-2) | Rhesus macaque | 114 | Gram+ & Gram−, Fungi | Tang (1999) |
| Termicin | *Pseudacanthotermes spiniger* | 115 | Gram+, Fungi | Lamberty (2001) |
| Spingerin | *Pseudacanthotermes spiniger* | 116 | Gram+ & Gram−, Fungi | Lamberty (2001) |
| Aurein 1.1 | Southern bell frog | 117 | Gram+ & Gram−, Fungi | Rozek (2000) |
| Ponericin G! | Ponerine ant | 118 | Gram+ & Gram−, Fungi | Orivel (2001) |
| Brevinin-1BB | Rio Grande leopard frog | 119 | Gram+ & Gram−, Fungi | Goraya (2000) |
| Ranalexin-1CB | Gree frog | 120 | Gram+ & Gram−, Fungi | Halverson (2000) |

TABLE 1-continued

| Name | Source | Seq. ID | Activity | Reference |
|---|---|---|---|---|
| Ranatuerin-2CA | Green frog | 121 | Gram+ & Gram−, Fungi | Halverson (2000) |
| Ranatuerin-2CB | Green frog | 122 | Gram+ & Gram−, Fungi | Halverson (2000) |
| Ginkbilobin | Ginkgo | 123 | Gram+ & Gram−, Virus, Fungi | Wang (2000) |
| Alpha-basrubrin (Fragment) | Malabar spinach | 124 | Virus, Fungi | Wang (2001) |
| Pseudin 1 | Paradoxical frog | 125 | Gram+ & Gram−, Fungi | Olson (2001) |
| Parabutoporin | Scorpion | 126 | Gram+ & Gram−, Fungi, Mammalian cells | Moerman (2002) |
| Opistoporin 1 | African yellow leg scorpion | 127 | Gram+ & Gram−, Fungi, Mammalian cells | Moerman (2002) |
| Opistoporin 2 | African yellow leg scorpion | 128 | Gram+ & Gram−, Fungi, Mammalian cells | Moerman (2002) |
| Histone H2A (fragment) | Rainbow trout | 129 | Gram+, Fungi | Fernandes (2002) |
| Dolabellanin B2 | Sea hare | 130 | Gram+ & Gram−, Fungi | Iijima (2002) |
| Cecropin A | Nocutuid moth | 131 | Gram+ & Gram−, Fungi | Bulet (2002) |
| HNP-5 Defensin | Human | 132 | Gram+ & Gram−, Fungi | Jones (1992) |
| HNP-6 Defensin | Human | 133 | Gram+ & Gram−, Fungi | Jones (1993) |
| Holotricin 3 | Holotrichia diomphalia | 134 | Fungi | Lee (1995) |
| Lingual antimicrobial peptide | Bovine | 135 | Gram+ & Gram−, Fungi | Schonwetter (1995) |
| RatNP-3 | Rat | 136 | Gram+ & Gram−, Virus, Fungi | Yount (1995) |
| GNCP-1 | Guinea pig | 137 | Gram+ & Gram−, Virus, Fungi | Nagaoka (1993) |
| Penaeidin-4a | Penoeid shrimp | 138 | Gram+ & Gram−, Fungi | Destoumieux (2000) |
| Hexapeptide | Bovine | 139 | Gram+ & Gram−, Virus, Fungi, Cancer cells | Vogle (2002) |
| P-18 |  | 140 | Gram+ & Gram−, Fungi, Cancer cells | Lee (2002) |
| MUC7 20-Mer | Human | 141 | Gram+ & Gram−, Fungi | Bobek (2003) |
| Nigrocin 2 | Rana nigromaculata | 142 | Gram+ & Gram−, Fungi | Park (2001) |
| Nigrocin 1 | Rana nigromaculata | 143 | Gram+ & Gram−, Fungi | Park (2001) |
| Lactoferrin (Lf) peptide 2 |  | 144 | Fungi | Ueta (2001) |
| Ib-AMP3 | Impatiens balsamina | 145 | Gram+, Fungi | Ravi (1997) |
| Ib-AMP4 | Impatiens balsamina | 146 | Gram+ Fungi | Ravi (1997) |
| Dhvar4 | Synthesis | 147 | Gram+ & Gram−, Fungi | Ruissen (2002) |
| Dhvar5 | Synthesis | 148 | Gram+ & Gram−, Fungi | Ruissen (2002) |
|  | Synthetic | 149 | Fungi | U.S. App. 10/601,207 |
|  | Synthetic | 150 | Fungi | U.S. App. 10/601,207 |
|  | Synthetic | 151 | Fungi | U.S. App. 10/601,207 |
|  | Synthetic | 152 | Fungi | U.S. App. 10/601,207 |
|  | Synthetic | 153 | Fungi | U.S. App. 10/601,207 |
|  | Synthetic | 154 | Fungi | U.S. App. 10/601,207 |
|  | Synthetic | 155 | Fungi | U.S. App. 10/601,207 |
|  | Synthetic | 156 | Fungi | U.S. App. 10/601,207 |
|  | Synthetic | 157 | Fungi | U.S. App. 10/601,207 |
|  | Synthetic | 158 | Fungi | U.S. App. 10/601,207 |
|  | Synthetic | 159 | Fungi | U.S. App. 10/601,207 |
|  | Synthetic | 160 | Fungi | U.S. App. 10/601,207 |
|  | Synthetic | 161 | Fungi | U.S. App. 10/601,207 |
|  | Synthetic | 162 | Fungi | U.S. App. 10/601,207 |
|  | Synthetic | 163 | Fungi | U.S. App. 10/601,207 |

TABLE 1-continued

| Name | Source | Seq. ID | Activity | Reference |
|---|---|---|---|---|
| | Synthetic | 164 | Fungi | U.S. App. 10/601,207 |
| | Synthetic | 165 | Fungi | U.S. App. 10/601,207 |
| | Synthetic | 166 | Fungi | U.S. App. 10/601,207 |
| | Synthetic | 167 | Fungi | U.S. App. 10/601,207 |
| | Synthetic | 168 | Fungi | U.S. App. 10/601,207 |
| | Synthetic | 169 | Fungi | U.S. App. 10/601,207 |
| | Synthetic | 170 | Fungi | U.S. App. 10/601,207 |
| | Synthetic | 171 | Fungi | U.S. App. 10/601,207 |
| | Synthetic | 172 | Fungi | U.S. App. 10/601,207 |
| | Synthetic | 173 | Fungi | U.S. App. 10/601,207 |
| | Synthetic | 174 | Fungi | U.S. App. 10/601,207 |
| | Synthetic | 175 | Fungi | U.S. App. 10/601,207 |
| | Synthetic | 176 | Fungi | U.S. App. 10/601,207 |
| | Synthetic | 177 | Fungi | U.S. App. 10/601,207 |
| | Synthetic | 178 | Fungi | U.S. App. 10/601,207 |
| | Synthetic | 179 | Fungi | U.S. App. 10/601,207 |
| | Synthetic | 180 | Fungi | U.S. App. 10/601,207 |
| | Synthetic | 181 | Fungi | U.S. App. 10/601,207 |
| | Synthetic | 182 | Fungi | U.S. App. 10/601,207 |
| | Synthetic | 183 | Fungi | U.S. App. 10/601,207 |
| | Synthetic | 184 | Fungi | U.S. App. 10/601,207 |
| | Synthetic | 185 | Fungi | U.S. App. 10/601,207 |
| | Synthetic | 186 | Fungi | U.S. App. 10/601,207 |
| | Synthetic | 187 | Fungi | U.S. App. 10/601,207 |
| | Synthetic | 188 | Fungi | U.S. App. 10/601,207 |
| | Synthetic | 189 | Fungi | U.S. App. 10/601,207 |
| | Synthetic | 190 | Fungi | U.S. App. 10/601,207 |
| | Synthetic | 191 | Fungi | U.S. App. 10/601,207 |
| | Synthetic | 192 | Fungi | U.S. App. 10/601,207 |
| | Synthetic | 193 | Fungi | U.S. App. 10/601,207 |
| | Synthetic | 194 | Fungi | U.S. App. 10/601,207 |
| | Synthetic | 195 | Fungi | U.S. App. 10/601,207 |
| | Synthetic | 196 | Fungi | U.S. App. 10/601,207 |
| | Synthetic | 197 | Gram+ & Gram−, Fungi | U.S. App. 10/601,207 |
| | Synthetic | 198 | Gram+ & Gram−, Fungi | U.S. App. 10/601,207 |
| | Synthetic | 199 | Gram+ & Gram−, Fungi | U.S. App. 10/601,207 |

In the above-referenced U.S. Pat. Nos. 6,020,312; 5,885,782; and 5,602,097 an iterative process was used to identify active peptide sequences with broad spectrum antifungal activity. A representative method employs a hexapeptide library with the first two amino acids in each peptide chain individually and specifically defined and with the last four amino acids consisting of equimolar mixtures of 20 amino acids. Four hundred (400) ($20^2$) different peptide mixtures each consisting of 130,321 ($19^4$) (cysteine was eliminated) individual hexamers were evaluated. In such a peptide mixture, the final concentration for each peptide was 9.38 ng/ml, in a mixture composed of 1.5 mg (peptide mix)/ml solution. This mixture profile assumed that an average peptide has a molecular weight of 785. This concentration was sufficient to permit testing for antifungal activity. Both D- and L-amino acid containing peptides may be constructed and tested to identify peptide compositions that can inhibit or kill fungi that can grow on the surfaces of inanimate objects. Peptide compositions comprising substantially homogeneous peptide compositions, as well as mixtures of peptides derived from amino acids that are between 3 to 25 residues in length (a length readily accomplished using standard peptide synthesis procedures), especially six residues in length, are disclosed in U.S. Pat. Nos. 6,020,312; 5,885,782; and 5,602,097. A preferred antifungal peptide that inhibits or kills one or more fungus that infests and grows on the surfaces of inanimate objects is a hexapeptide having the amino acid sequence Phe Arg Leu Lys Phe His (SEQ ID No. 41).

Homogeneous peptide compositions are chiefly composed of a single active peptide species of a well-defined sequence. Minor amounts (less than 20% by moles) of impurities may coexist with the peptide in these compositions so long as they do not interfere with the growth inhibitory properties of the active peptide(s). Target fungi include but are not limited to those fungi that can infest indoor and outdoor structures and building materials causing defacement (e.g., deterioration or discoloration), odor, environment hazards, and other undesirable effects. Alternatively to using one or more isolated antifungal peptides as the antifungal peptidic agent, the agent may instead be a peptide library aliquot containing a mixture of peptides in which at least two (and preferably three or four) of the N-terminal amino acid residues are known. If the peptidic agent is a mixture of peptides, at least one will have antifungal activity. As will be apparent in examples which follow, for ease of production and lower cost, in many instances it will be preferred to use a peptide library aliquot that contains at least one antifungal peptide, preferably the hexapeptide of SEQ ID No. 41, but is impure to the extent that it may also include peptides of unknown exact sequence which may or may not have antifungal activity. In addition, the peptide or peptide library may be one that has side chains blocked, is attached to the synthetic resin or both blocked and attached.

Example 2

Identifying Antifungal Peptides that Inhibit Target Organisms

The testing methods described in U.S. Pat. Nos. 6,020,312; 5,885,782; and 5,602,097 may be employed to screen the peptide library for antifungal activity against a wide variety of fungus genera and species. Preferably the methods are modified to screen against fungal organisms that are known to, or suspected of, infesting construction materials or other vulnerable materials and surfaces. More preferably, fungal cells used for screening the peptide library include members of the genera *Stachybotrys* (especially *Stachybotrys chartarum*), *Aspergillus* species (sp.), *Penicillium* sp., *Fusarium* sp., *Alternaria dianthicola, Aureobasidium pullulans* (aka *Pullularia pullulans*), *Phoma pigmentivora* and *Cladosporium* sp. Cell culture conditions may also be modified appropriately to provide favorable growth and proliferation conditions, as is within the capability of one of ordinary skill in the art. The above-mentioned methods will be used to identify peptides or groups of peptides that demonstrate broad-spectrum antifungal activity. Similar methods will be used to identify particular peptides or groups of peptides that target specific fungus genera or species. Alternatively, but less preferred, any other suitable peptide/polypeptide/protein screening method could be used instead to identify antifungal peptide candidates for testing as active antifungal agents in paints and other coating materials.

It is known that certain of the peptides of particular usefulness in the coatings of the invention, as disclosed in U.S. Pat. Nos. 6,020,312; 5,602,097; and 5,885,782, exhibit variable abilities to inhibit fungal growth as adjudged by the minimal inhibitory concentrations (MIC mg/ml) and/or the concentrations necessary to inhibit growth of fifty percent of a population of fungal spores (IC50 mg/ml). MICs may range depending upon peptide additive and target organism from about 3 to about 300 mg/ml, while IC50's may range depending upon peptide additive and target organisms from about 2 to about 100 mg/ml. Target organisms susceptible to these amounts include *Fusarium oxysporum, Fusariam Sambucinum, Rhizoctonia Solani, Ceratocystis Fagacearum, Pphiostoma ulmi, Pythium ultimum, Magaporthe Aspergillus nidulans, Aspergillus fumigatus*, and *Aspergillus Parasiticus*.

The mode of action of antifungal peptides, polypeptides and proteins, by which they exert their inhibitory or fungicidal effects, can be varied. For instance, certain peptides may operate to destabilize fungal cell membranes, while the modes of action of others could include disruptions of macromolecular synthesis or metabolism. While the modes of action of some known antifungal peptides have been determined (see, e.g., Fiedler, H. P., et al. 1982. Nikomycins: microbial inhibitors of chitin synthase. J. Chem. Technol. Biotechnol. 32:271-280; Isono, K. and S. Suzuki. 1979. The polyoxins: pyrimidine nucleoside peptide antibiotics inhibiting fungal cell wall biosynthesis. Heterocycles 13:333-351), mechanisms which explain their modes of action and specificity have typically not yet been determined. Initial studies to elucidate antifungal mode of action of peptides involves a physical examination of mycelia and cells to determine if the peptides can perturb membrane functions responsible for osmotic balance, as has been observed for other peptides (Zasloff, M. 1987. Proc. Natl. Acad. Sci. USA 84:5449-5453). Disruption of appressorium formation may also be the mechanism by which some peptides inhibit fungal growth (see e.g., published U.S. patent application Ser. No. 10/601,207, expressly incorporated herein by reference in its entirety). For the purposes of preparing and using antifungal peptides, polypeptides and/or proteins as active antifungal agents in paints and other coating compositions, it is not necessary to understand the mechanism by which the desired antifungal effect is exerted on fungus cells.

Example 3

Varying the Amino Acid Sequence of Antifungal Peptides

For the purposes of preparing antifungal paints and other coating compositions containing antifungal peptidic agents, it should be appreciated that it is not necessary for the amino acid sequence of a peptide having demonstrable antifungal activity to be completely defined. In certain situations, especially where an antifungal peptide is being used to target an array of fungal genera or species, mixed peptide additives may be preferable. This is also likely to be the case where there is a desire to treat or prevent infestation by a particular species of fungus using lower concentrations of numerous antifungal peptides rather than a higher concentration of a single peptide. In other situations where, for instance, due to the increased cost of testing or producing a completely defined peptide antifungal peptide is prohibitive, the mixed peptide compositions having one or more variable amino acid residues may be preferred. Similarly, it may be preferable to leave synthetic peptides of the invention blocked and/or covalently attached to the synthetic resin so long as sufficient antifungal activity is exhibited in the coating. Thus, antifungal additive compositions comprising equimolar mixtures of peptides produced in a synthetic peptide combinatorial library utilizing the methods described herein and/or in U.S. Pat. No. 6,020,312, U.S. Pat. No. 5,885,782, or U.S. Pat. No. 5,602,097 may be employed as antifungal agents in paints, coatings and films.

The antifungal peptide additives for the coatings of the invention may be constructed using a variety of amino acid precursors. Of course, the peptides may be homogenous compositions containing only D-, L- or cyclic (non-racemic) amino acids. The chemical structure of such amino acids (which term is used herein to include imino acids), regardless of stereoisomeric configuration, may be based upon that of the nineteen or twenty naturally-occurring amino acids: alanine (Ala; A), arginine (Arg; R), asparagine (Asn; N), aspartate (Asp; D), glutamine (Gln; Q), glutamate (Glu; E), glycine (Gly; G), histidine (His; H), isoleucine (Ile; I), leucine (Leu; L), lysine (Lys; K), methionine (Met; M), proline (Pro; P), phenylalanine (Phe; F), serine (Ser; S), threonine (Thr; T), tryptophan (Trp; W), tyrosine (Tyr; Y), and valine (Val; V). Cysteine (Cys; C) is preferably excluded to prevent disulfide linkage problems in the products. The compositions of the invention may also be non-homogenous, containing for instance both D-, L- and/or cyclic amino acids. The peptide compositions may also contain amino acids which are other than the naturally-occurring amino acids (e.g., norleucine), as are known to those of skill in the art. The peptides may also be constructed as retroinversopeptidomimetics of any of the peptides shown to be active in either the D- or L-configurations. It is known, for instance, that the retroinversopeptidomimetic of SEQ ID No. (41) is inhibitory (albeit less so than either the D- or L-configurations) against certain household fungi such as *Fusarium* and *Aspergillus* (Guichard, 1994).

Preferred antifungal paints and coatings will comprise one or more of the peptides disclosed in SEQ ID Nos. 1-199, more preferably SEQ ID Nos. 1-47. These sequences establish a number of precise chemical compositions which have been shown to have antifungal activity against a spectrum of fungi, but which were not previously known to be useful for treating and/or protecting building materials and other non-living objects from infestation by fungi. A highly preferred antifungal peptide is the hexapeptide of SEQ ID No. 41.

In certain instances, the peptides will have completely defined sequences. In other instances, the sequence of the antifungal peptide will be defined for only certain of the C-terminal amino acid residues leaving the remaining amino acid residues defined as equimolar ratios. For example, certain of the peptides of SEQ ID Nos. 1-199 have somewhat variable amino acid compositions. Thus, in each aliquot of the SPCL containing a given SEQ ID Nos. having a variable residue, the variable residues will each be uniformly represented in equimolar amounts by one of nineteen different naturally-occurring amino acids in one or the other stereoisomeric form. However, the variable residues may be rapidly defined using the method described in one or more of U.S. Pat. Nos. 6,020,312; 5,602,097; and 5,885,782 to identify peptides that possess activity for controlling fungal growth. In the cited patents it was demonstrated that peptides encompassed by the C-terminal sequence "XXXXRF" (SEQ ID No. 1) exhibited antifungal activity for a wide spectrum of fungi. For ease of reference, peptides herein are written in the C-terminal to N-terminal direction to denote the sequence of synthesis. However, the conventional N-terminal to C-terminal manner of reporting amino acid sequences is utilized in the Sequence Listings. This relatively variable composition, therefore, is described as an antifungal peptide even though it is likely that not every peptide encompassed by that general sequence will possess the same or any antifungal activity.

In the next round of identification of antifungal peptides encompassed by the general sequence "XXXXRF" (SEQ ID No. 1) parent composition of known antifungal activity, "XXXLRF" (SEQ ID No. 9) peptides mixtures were found to exhibit significant antibiotic activity (also disclosed in U.S. Pat. Nos. 6,020,312; 5,602,097; and 5,885,782). Similarly to the parent composition "XXXXRF" (SEQ ID No. 1), the "XXXLRF" (SEQ ID No. 9) peptides will have a mixed equimolar array of peptides representing the same nineteen amino acid residues, some of which may have antifungal activity and some of which may not have such activity. Overall, however, the "XXXLRF" (SEQ ID No. 9) peptide composition is itself an antifungal agent. This process is carried out to the point where completely defined peptides are produced and tested for their antifungal activity, as described in Example 2 or using any suitable method that would be known to one of skill in the art. As a result, and as was accomplished for the representative peptide "FHLRF" (SEQ ID No. 31), all amino acid residues in a six residue peptide will be known.

It will be recognized by those of skill in the art that the peptides to be employed as antifungal agents for paints, coatings and other compositions, once selected, may be modified to contain functionally equivalent amino acid substitutions and yet retain the same or similar antifungal characteristics. The importance of the hydropathic index of amino acids in conferring biological function on a protein has been discussed generally by Kyte and Doolittle, *J. Mol. Biol.*, 157: 105-132, 1982. It is well known that certain amino acids may be substituted for other amino acids having a similar hydropathic index or score and still retain similar if not identical biological activity. As displayed in Table 2 below, amino acids are assigned a hydropathic index on the basis of their hydrophobicity and charge characteristics. It is believed that the relative hydropathic character of the amino acid determines the secondary structure of the resultant protein, which in turn defines the interaction of the protein with the substrate molecule. Similarly, in peptides whose secondary structure is not a principal aspect of the interaction of the peptide, position within the peptide and the characteristic of the amino acid residue determine the interactions the peptide has in a biological system. It is proposed that biological functional equivalence may typically be maintained where amino acids having no more than a +/−1 to 2 difference in the index value, and more preferably within a +/−1 difference, are exchanged.

TABLE 2

| AMINO ACID | HYDROPATHIC INDEX |
|---|---|
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, it is expected that isoleucine, for example, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on. Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

TABLE 3

| Originally Screened Residue | Exemplary Substitutions |
|---|---|
| alanine | gly; ser |
| arginine | lys |
| asparagine | gln; his |
| aspartate | glu |
| cysteine | ser |
| glutamate | asp |
| glutamine | asn |
| glycine | ala |
| histidine | asn; gln |
| isoleucine | leu; val |
| leucine | ile; val |
| lysine | arg; gln; glu |
| methionine | met; leu; tyr |
| serine | thr |
| threonine | ser |
| tryptophan | tyr |
| tyrosine | trp; phe |
| valine | ile; leu |

Example 4

Stabilized Antifungal Peptide Compositions

A variety of modifications can be made to the peptides as long as antifungal activity is retained. Some modifications may be used to increase the intrinsic antifungal potency of the peptide. Other modifications may facilitate handling of the peptide. Peptide functional groups that may typically be modified include hydroxyl, amino, guanidinium, carboxyl, amide, phenol, imidazol rings or sulfhydryl. Typical reactions of these groups include but are not limited to acetylation of hydroxyl groups by alkyl halides. Carboxyl groups may be esterified, amidated or reduced to alcohols. Carbodiimides or other catalysts may be used to catalyze the amidation of carboxyl groups. The amide groups of asparagine or glutamine may be deamidated under acidic or basic conditions. Acylation, alkylation, arylation or amidation reactions readily occur with amino groups such as the primary amino group of the peptide or the amino group of lysine residues. The phenolic group of tyrosine can be halogenated or nitrated. Examples where solubility of a peptide could be decreased include acylating charged lysine residues or acetylating the carboxyl groups of aspartic and glutamic acids. Techniques and materials that are suitable for carrying out each of these modifications are well known in the art and have been described in the literature.

Another way in which the antifungal activity of the peptides may be stabilized in paints and other coatings and compositions is by linking or conjugation to another molecule. Peptides may be conjugated to soluble or insoluble carrier molecules to modify their solubility properties as needed. Examples of soluble carrier molecules include polymers of polyethyleneglycol and polyvinylpyrrolidone. Alternatively, a peptide may be chemically linked or tethered to an insoluble molecule. Examples of insoluble polymers include sand or other silicates, and polystyrene, cellulose and polyvinylchloride. Such polymers are often employed in coatings. The molecular size of the conjugated polymer chosen for conjugating with an antifungal peptide is preferably suited for carrying out the desired additional function in the coating. Techniques and materials for conjugating peptides to other molecules are well known in the art and have been described in the literature.

Still another way in which the antifungal activity may be controlled or stabilized is by microencapsulating the peptides to enhance their stability in liquid coating compositions and in the final paint film or coat. For example, polyester microspheres may be used to encapsulate and stabilize the peptides in a paint composition during storage, or to provide for prolonged, gradual release of the peptide after it is dispersed in a paint film covering a surface that is vulnerable to attachment and growth of fungal cells or spores. Any suitable microencapsulation technique as would be known to one of ordinary skill in the art may be employed. Such encapsulation may enhance, or confer a particulate nature to, one or more antifungal peptide. The encapsulating membrane may provide protection to the peptide from peptidases, proteases, and other peptide bond or side chain modifying substances, it may serve to increase the average particle size of the antifungal peptidic agent to a desired range, and it may allow controlled release of the peptide(s) from the encapsulating material, alter surface charge, hydrophobicity, hydrophilicity, solubility and/or dispersability of the particulate material, or any combination of those functions. Examples of microencapsulation (e.g., microsphere) compositions and techniques are described in Wang, H. T. et al., *J. of Controlled Release* 17:23-25, 1991; and U.S. Pat. Nos. 4,324,683; 4,839,046; 4,988,623; 5,026,650; 5,153,131; 6,485,983; 5,627,021 and 6,020,312). Other microencapsulation methods which may be employed are those described in U.S. Pat. Nos. 5,827,531; 6,103,271; and 6,387,399.

Example 5

Large-Scale Production of Antifungal Peptides

An antifungal peptide sequence identified as described above may be grown in bacterial, insect, or other suitable cells employing techniques and materials that are well known in the art, except DNA encoding the antifungal peptides described herein will be used instead of a previous DNA sequence. For example, an expression vector will include a DNA sequence encoding SEQ ID No. 1 in the correct orientation and reading frame with respect to the promoter sequence to allow translation of the DNA encoding the SEQ ID No. 1. Examples of the cloning and expression of an exemplary gene and DNAs are known. Either batch culture production methods or continuous fed-batch culture methods may be employed to produce commercial-scale quantities of antifungal peptides.

Example 6

Antifungal Additives Isolated from Microorganisms

Although synthetically obtained antifungal peptidic agents (i.e., peptides, polypeptides and proteins) that are identified and produced as described above are highly preferred, it is also possible to employ suitable naturally occurring antifungal peptidic agents, and microbes that produce such agents, as additives in paints and other coatings. A number of such naturally occurring peptide additives are listed in Table 1. A drawback to this is the time-consuming process of searching for naturally produced antifungal agents with very low-probability of success. The use of natural antifungal products isolated in commercial quantity from microorganisms is also limited in usefulness due in large part to purification problems. Large-scale cell culture of the antifungal agent-producing microorganism is required for the purification of the antifungal product. In many instances, the cultural isolate responsible for the production of the antifungal agent is not an isolate which is easily batch-cultured or it is entirely incapable of batch culturing. Furthermore, complicated purification strategies are often required to purify the active product to a reasonable level of homogeneity. A substantial disadvantage to the use of naturally derived antifungal agents is the potential for co-purification of unwanted microbial byproducts, especially byproducts which are undesirably toxic. In many cases, these factors lead to high production costs and make large-scale isolation of antifungal products from natural isolates impractical. Purifications may be even more difficult where racemized mixtures are possible where only a single stereoisomer is active, or where disulfide linkages are possible between peptide monomers. Even when desirable naturally occurring antifungal proteins or polypeptides are isolated, for example, and their amino acid sequences at least partially identified, synthesis of the native molecule, or portions thereof, may be problematic due to the need for specific disulfide bond formation, high histidine requirements, and so forth. Nonetheless, natural sources provide additional sequences to be explored as coating additives.

Example 7

Coating Formulations Containing Antifungal Peptide Additives

One or more of the antifungal peptides or peptide compositions, prepared as described in any of the foregoing examples, is mixed with a base paint or other coating, which may be any suitable commercially available product, a wide variety of which are well known in the art. Preferably the base composition is free of chemicals and other additives that are toxic to humans or animals, and/or that fail to comply with applicable environmental safety rules or guidelines. In some instances, it may be preferred to custom blend a paint or coating mixture using any combination of various naturally-occurring and synthetic components and additives that are known in the art and are also described in U.S. patent application Ser. No. 10/655,345 filed Sep. 4, 2003 or U.S. patent application Ser. No. 10/792,516 filed on Mar. 3, 2004, which are hereby expressly incorporated herein by reference in their entirety.

Coating components generally include a binder, a liquid component, a colorizing agent, one or more additive, or a combination of any of those. A coating typically comprises a material often referred to as a "binder," which is the primary material in a coating capable of producing a film. In most embodiments, a coating will comprise a liquid component (e.g., a solvent, a diluent, a thinner), which often confers and/or alters the coating's rheological properties (e.g., viscosity) to ease the application of the coating to a surface. Usually a coating (e.g., a paint) will comprise a colorizing agent (e.g., a pigment), which usually functions to alter an optical property of a coating and/or film. A coating will often comprise an additive, which is a composition incorporated into a coating to (a) reduce and/or prevent the development of a physical, chemical, and/or aesthetic defect in the coating and/or film; (b) confer some additional desired property to a coating and/or film; or (c) a combination thereof. Examples of an additive include an accelerator, an adhesion promoter, an antifloating agent, an antiflooding agent, an antifoaming agent, an antioxidant, an antiskinning agent, a buffer, a catalyst, a coalescing agent, a corrosion inhibitor, a defoamer, a dehydrator, a dispersant, a drier, an electrical additive, an emulsifier, a film-formation promoter, a fire retardant, a flow control agent, a gloss aid, a leveling agent, a light stabilizer, a marproofing agent, a matting agent, a neutralizing agent, a preservative, a rheology modifier, a slip agent, a viscosity control agent, a wetting agent, or a combination thereof. The content for an individual coating additive in a coating generally is 0.0001% to 20.0%, including all intermediate ranges and combinations thereof. However, in many instances it is preferred if the concentration of a single additive in a coating comprises between 0.0001% and 10.0%, including all intermediate ranges and combinations thereof.

Some of the usual types of components of paints and coatings are summarized as follows:

Binders: oil-based (e.g., oils, alkyd resins, oleoresinous binders, and fatty acid epoxy esters; polyester resins; modified cellulose; polyamide; amidoamine; amino resins; urethanes; phenolic resins; epoxy resins; polyhydroxyether; acrylic resins; polyvinyl binders; rubber resins; bituminous; polysulfide and silicone.

Liquid Components: solvents; thinners; diluents; plasticizers; and water (e.g., hydrocarbons; oxygenated solvents; chlorinated hydrocarbons, nitrated hydrocarbons, other organic liquids)

Colorants: pigments and dyes.

Additives: preservatives (e.g., biocides/bactericides/fungicides/algaecides); wetting agents; buffers (e.g., ammonium bicarbonate, both monobasic and dibasicphosphate buffers, Trizma base and zwitterionic buffers); rheology modifiers; defoamers; catalysts (e.g., driers, acids, bases, urethane catalysts); antiskinning agents; light stabilizers; corrosion inhibitors; dehydrators; electrical additives; and anti-insect additives.

Preservatives serve to reduce or prevent the deterioration of a coating and/or film by a microorganism, by acting as a biocide, which kills an organism, a biostatic, which reduces or prevents the growth of an organism, or a combination of effects. Examples of a biocide include, for example, a bactericide, a fungicide, an algaecide, or a combination thereof.

A preferred paint or coating composition contains, as a preservative, an antifungal peptidic agent (i.e., one or more peptides, polypeptides or proteins), according to any of Examples 1-6. An antifungal peptidic agent may be used as a partial or complete substitute ("replacement") for another fungicide and/or fungistatic that is typically used in a fungus prone composition. It is contemplated that 0.0001% to 100%, including all intermediate ranges and combinations thereof, of a conventional antifungal component in a coating formulation may be substituted by an antifungal peptidic agent. In some formulations, the concentration of antifungal peptidic agent may exceed 100%, by weight or volume, of the non-peptidic antifungal component (fungicide or fungistat) that is being replaced. A conventional non-peptidic antifungal component may be replaced with an antifungal peptidic agent equivalent to 0.001% to 500% (by weight, or by volume), including all intermediate ranges and combinations thereof, of the substituted antifungal component. For example, to produce a coating with similar fungal resistance properties as a non-substituted formulation, it may require that 20% (e.g., 0.2 kg) of a chemical fungicide may be replaced by 10% (e.g., 0.1 kg) of an antifungal peptidic agent. In another exemplary formulation, to produce a coating with similar fungal resistance as a non-substituted formulation, it may require replacing 70% of a chemical fungicide (e.g., 0.7 kg) with the equivalent of 127% (e.g., 1.27 kg) of antifungal peptidic agent. The various assays described herein, or as would be known to one of ordinary skill in the art in light of the present disclosure, may be used to determine the fungal resistance properties of a composition (e.g., a coating, a film) produced by direct addition of an antifungal peptidic agent and/or substitution of some or all of a non-peptidic or chemical antifungal component by an antifungal peptidic agent. Such additives may be directly admixed with the coating, applied as a primer coating, applied as an overcoat, or any combination of these application techniques.

A preservative may comprise an in-can preservative, an in-film preservative, or a combination thereof. An in-can preservative is a composition that reduces or prevents the growth of a microorganism prior to film formation. Addition of an in-can preservative during a water-borne coating production typically occurs with the introduction of water to a coating composition. Typically, an in-can preservative is added to a coating composition for function during coating preparation, storage, or a combination thereof. An in-film preservative is a composition that reduces or prevents the growth of a microorganism after film formation. Oftentimes an in-film preservative is the same chemical as an in-can preservative, but added to a coating composition at a higher (e.g., two-fold) concentration for continuing activity after film formation.

Examples of preservatives that have been used in coatings include a metal compound (e.g., an organo-metal compound) biocide, an organic biocide, or a combination thereof.

Examples of a metal compound biocide include barium metaborate (CAS No. 13701-59-2), which is a fungicide and bactericide; copper (II) 8-quinolinolate (CAS No. 10380-28-6), which is a fungicide; phenylmercuric acetate (CAS No. 62-38-4), tributyltin oxide (CAS No. 56-35-9), which is less preferred for use against Gram-negative bacteria; tributyltin benzoate (CAS No. 4342-36-3), which is a fungicide and bactericide; tributyltin salicylate (CAS No. 4342-30-7), which is a fungicide; zinc 2-pyridinethiol-N-oxide (CAS No. 13463-41-7), which is a fungicide; zinc oxide (CAS No. 1314-13-2), which is a fungistatic/fungicide and algaecide; a combination of zinc-dimethyldithiocarbamate (CAS No. 137-30-4) and zinc 2-mercaptobenzothiazole (CAS No. 155-04-4), which acts as a fungicide; zinc 2-pyridinethiol-N-oxide (CAS No. 13463-41-7), which is a fungicide; a metal soap; or a combination thereof. Examples of metals comprised in a metal soap biocide include copper, mercury, tin, zinc, or a combination thereof. Examples of an organic acid comprised in a metal soap biocide include a butyl oxide, a laurate, a naphthenate, an octoate, a phenyl acetate, a phenyl oleate, or a combination thereof. It is anticipated that the peptide additives of the present invention will work in combination with or synergistically with such preservatives.

An example of an organic biocide that acts as an algaecide includes 2-methylthio-4-tert-butylamino-6-cyclopropylamino-s-triazine (CAS No. 28159-98-0). Examples of an organic biocide that acts as a bactericide include a combination of 4,4-dimethyl-oxazolidine (CAS No. 51200-87-4) and 3,4,4-trimethyloxazolidine (CAS No. 75673-43-7); 5-hydroxy-methyl-1-aza-3,7-dioxabicylco (3.3.0.) octane (CAS No. 59720-42-2); 2(hydroxymethyl)-aminoethanol (CAS No. 34375-28-5); 2-(hydroxymethyl)-amino-2-methyl-1-propanol (CAS No. 52299-20-4); hexahydro-1,3,5-triethyl-s-triazine (CAS No. 108-74-7); 1-(3-chloroallyl)-3,5,7-triaza-1-azonia-adamantane chloride (CAS No. 51229-78-8); 1-methyl-3,5,7-triaza-1-azonia-adamantane chloride (CAS No. 76902-90-4); p-chloro-m-cresol (CAS No. 59-50-7); an alkylamine hydrochloride; 6-acetoxy-2,4-dimethyl-1,3-dioxane (CAS No. 828-00-2); 5-chloro-2-methyl-4-isothiazolin-3-one (CAS No. 26172-55-4); 2-methyl-4-isothiazolin-3-one (CAS No. 2682-20-4); 1,3-bis (hydroxymethyl)-5,5-dimethylhydantoin (CAS No. 6440-58-0); hydroxymethyl-5,5-dimethylhydantoin (CAS No. 27636-82-4); or a combination thereof. Examples of an organic biocide that acts as a fungicide include a parabens; 2-(4-thiazolyl)benzimidazole (CAS No. 148-79-8); N-trichloromethyl-thio-4-cyclohexene-1,2-dicarboximide (CAS No. 133-06-2); 2-n-octyl-4-isothiazoline-3-one (CAS No. 26530-20-1); 2,4,5,6-tetrachloro-isophthalonitrile (CAS No. 1897-45-6); 3-iodo-2-propynyl butyl carbamate (Cas No. 55406-53-6); N-(trichloromethyl-thio)phthalimide (Cas No. 133-07-3); tetrachloroisophthalonitrile (Cas No. 1897-45-6); potassium N-hydroxy-methyl-N-methyl-dithiocarbamate (Cas No. 51026-28-9); sodium 2-pyridinethiol-1-oxide (Cas No. 15922-78-8); or a combination thereof. Examples of a parbens include butyl parahydroxybenzoate (Cas No. 94-26-8); ethyl parahydroxybenzoate (Cas No. 120-47-8); methyl parahydroxybenzoate (Cas No. 99-76-3); propyl parahydroxybenzoate (Cas No. 94-13-3); or a combination thereof. Examples of an organic biocide that acts as an bactericide and fungicide include 2-mercaptobenzo-thiazole (Cas No. 149-30-4); a combination of 5-chloro-2-methyl-3(2H)-isothiazoline (Cas No. 26172-55-4) and 2-methyl-3(2H)-isothiazolone (Cas No. 2682-20-4); a combination of 4-(2-nitrobutyl)-morpholine (Cas No. 2224-44-4) and 4,4'-(2-ethylnitrotrimethylene dimorpholine (Cas No. 1854-23-5); tetra-hydro-3,5-dimethyl-2H-1,3,5-thiadiazine-2-thione (Cas No. 533-74-4); potassium dimethyldithiocarbamate (Cas No. 128-03-0); or a combination thereof. An example of an organic biocide that acts as an algaecide and fungicide includes diiodomethyl-p-tolysulfone (Cas No. 20018-09-1). Examples of an organic biocide that acts as an algaecide, bactericide and fungicide include glutaraldehyde (CAS No. 111-30-8); methylenebis (thiocyanate) (Cas No. 6317-18-6); 1,2-dibromo-2,4-dicyanobutane (CAS No. 35691-65-7); 1,2-benzisothiazoline-3-one (CAS No. 2634-33-5); 2-(thiocyanomethyl-thio) benzothiazole (CAS No. 21564-17-0); or a combination thereof. An example of an organic biocide that acts as an algaecide, bactericide, fungicide and molluskicide includes 2-(thiocyanomethyl-thio)benzothiozole (CAS No. 21564-17-0) and methylene bis(thiocyanate) (CAS No. 6317-18-6).

In certain situations of use, an applicable environmental law or regulation may encourage the selection of an organic biocide such as a benzisothiazolinone derivative. An example of a benzisothiazolinone derivative is Busan™ 1264 (Buckman Laboratories, Inc.), Proxel™ GXL (Avecia Inc.), or Preventol® VP OC 3068 (Bayer Corporation), which comprises 1,2-benzisothiazolinone (CAS No. 2634-33-5). In the case of Busan™ 1264, the primary use is a bactericide and/or fungicide at 0.03% to 0.5% in a water-borne coating.

Often, a preservative is a proprietary commercial formulation and/or a compound sold under a tradename. Examples include organic biocides under the tradename Nuosept® (International Specialty Products), which are typically used in a water-borne coating. Specific examples of a Nuosept® biocide includes Nuosept® 95, which comprises a mixture of bicyclic oxazolidines, and is typically added to 0.2% to 0.3% concentration to a coating composition; Nuosept® 145, which comprises an amine reaction product, and is typically added to 0.2% to 0.3% concentration to a coating composition; Nuosept® 166, which comprises 4,4-dimethyloxazolidine (CAS No. 51200-87-4), and is typically added to 0.2% to 0.3% concentration to a basic pH water-borne coating composition; or a combination thereof. A further example is Nuocide® (International Specialty Products) biocides, which are typically used fungicides and/or algaecides. Examples of a Nuocide® biocide is Nuocide® 960, which comprises 96% tetrachlorisophthalonitrile (CAS No. 1897-45-6), and is typically used at 0.5% to 1.2% in a water-borne or solvent-borne coating as a fungicide; Nuocide® 2010, which comprises chlorothalonil (CAS No. 1897-45-6) and IPBC (CAS No. 55406-53-6) at 30%, and is typically used at 0.5% to 2.5% in a coating as a fungicide and algaecide; Nuocide® 1051 and Nuocide® 1071, each which comprises 96% N-cyclopropyl-N-(1-dimethylethyl)-6-(methylthio)-1,3,5-triazine-2,4-diamine (CAS No. 28159-98-0), and is typically used as an algaecide in antifouling coatings at 1.0% to 6.0% or water-based coatings at 0.05% to 0.2%, respectively; and Nuocide® 2002, which comprises chlorothalonil (CAS No. 1897-45-6) and a triazine compound at 30%, and is typically used at 0.5% to 2.5% in a coating and/or a film as a fungicide and algaecide.

An additional example of a tradename biocide for coatings includes Vancide® (R. T. Vanderbilt Company, Inc.). Examples of a Vancide® biocide include Vancide® TH, which comprises hexahydro-1,3,5-triethyl-s-triazine (CAS No. 108-74-7), and is generally used in a water-borne coating; Vancide® 89, which comprises N-trichloromethylthio-4-cyclohexene-1,2-dicarboximide (CAS No. 133-06-2) and related compounds such as captan (CAS No. 133-06-2), and is used as a fungicide in a coating composition; or a combination thereof. A bactericide and/or fungicide for coatings, particularly a water-borne coating, is a Dowicil™ (Dow Chemical Company). Examples of a Dowicil™ biocide include Dowicil™ QK-20, which comprises 2,2-dibromo-3- nitrilopropionamide (CAS No. 10222-01-2), and is used as a bactericide at 100 ppm to 2000 ppm in a coating; Dowicil™ 75, which comprises 1-(3-chloroallyl)-3,5,7-triaza-1-azoniaadamantane chloride (CAS No. 51229-78-8), and is used as a bactericide at 500 ppm to 1500 ppm in a coating; Dowicil™ 96, which comprises 7-ethyl bicyclooxazolidine (CAS No. 7747-35-5), and is used as a bactericide at 1000 ppm to 2500 ppm in a coating; Bioban™ CS-1135, which comprises 4,4-dimethyloxazolidine (CAS No. 51200-87-4), and is used as a bactericide at 100 ppm to 500 ppm in a coating; or a combination thereof. An additional example of a tradename biocide for coatings includes Kathon® (Rohm and Haas Company). An example of a Kathon® biocide includes Kathon® LX, which typically comprises 5-chloro-2-methyl-4-isothiazolin-3-one (CAS no 26172-55-4) and 2-methyl-4-isothiazolin-3-one (CAS no 2682-20-4) at 1.5%, and is added from 0.05% to 0.15% in a coating. Examples of tradename fungicides and algaecides include those described for Fungitrol® (International Specialty Products), which are often formulated for solvent-borne and water-borne coatings, and in-can and film preservation. An example is Fungitrol® 158, which comprises 15% tributyltin benzoate (CAS No. 4342-36-3) (15%) and 21.2% alkylamine hydrochlorides, and is typically used at 0.35% to 0.75% in a water-borne coating for in-can and film preservation. An additional example is Fungitrol® 11, which comprises N-(trichloromethylthio) phthalimide (CAS No. 133-07-3), and is typically used at 0.5% to 1.0% as a fungicide for solvent-borne coating. A further example is Fungitrol® 400, which comprises 98% 3-iodo-2-propynl N-butyl carbamate ("IPBC") (Cas No. 55406-53-6), and is typically used at 0.15% to 0.45% as a fungicide for a water-borne or a solvent-borne coating. See Table 4.

TABLE 4

| Company | Product Roster |
| --- | --- |
| Arch Chemicals, Inc.<br>800.344.9168/Fax: 203.271.4060<br>E-mail: sales@archbiocides.com<br>www.archbiocides.com | Zinc Ornadine (Zinc Pyrithione/fungicide/algaecide)<br>Sodium Omadine (Sodium Pyrithione/fungicide-algaecide)<br>Copper Omadine (Copper Pyrithione/algaecide)<br>Triadine 174 (Triazine/bactericide)<br>Omacide IPBC (Iodopropynyl-butyl carbomate/fungicide)<br>Other: antifouling agents |
| Avecia Protection & Hygiene<br>Wilmington, DE<br>800.523.7391/Fax: 302.477.8120<br>E-mail: biocides@avecia.com<br>www.avecia.com/biocides | Proxel GXL (BIT)<br>Proxel BDZO (BIT)<br>Proxel BZ (BIT/ZPT)<br>Proxel TN (BIT/Triazine)<br>Proxel XL2 (BIT)<br>Densil C404 (Chlorthalonil)<br>Densil P (Densil P)<br>Densil DN (BUBIT)<br>Vantocil IB (PHMB) |
| BASF Corp.<br>Mount Olive, NJ<br>973.426.4358/Fax: 973.426.3863<br>www.biocides.basf-corp.com | Myacide AS Technical (Bronopol, solid)<br>Myacide AS 2, 30 and 15 (Bronopol, solutions)<br>Myacide GDA Technical (50% Glutaraldehyde)<br>Myacide GA 42, 26 & 15 (Glutaraldehyde, solut.)<br>Protectol PE (Phenoxyethanol, liquid)<br>Daomet Technical (Dazomet, solid)<br>Myacide HT Technical (Triazine, liquid) |
| Buckman Laboratories, Inc.<br>Memphis, TN<br>E-mail: knetix@buckman.com | Busan (wood preservative/pkg. pres.)<br>Butrol (corrosion inhibitor/rust inhibitor)<br>Busan (bactericide; mold inhibitor and biocide) |
| Cognis Corp.<br>Ambler, PA<br>800.445.2207/Fax: 215.628.1111<br>E-mail:<br>shruti.singhal@cognis.com<br>www.cognis.com | Nopcocide N400 (Cholorthalonil-40% solution)<br>Nopcocide N-98 (Chlorothalonil-100%)<br>Nopcocide P-20 (IPBC-20% solution)<br>Nopcocide P-40 (IPBC-40% solution)<br>Nopcocide P-100 (IPBC-100% active) |
| International Specialty Products<br>aka ISP<br>Wayne, NJ<br>800.622.4423/Fax: 973.628.4001<br>E-mail: info@ispcorp.com<br>www.ispcorp.com | Fungitrol (fungicides)<br>Biotrend (biocides)<br>Nuocide (fungicides/algaecides)<br>Nuosept (antimicrobial agents) |
| Rohm and Haas Company<br>Philadelphia, PA<br>www.rohmhaas.com | Katon LX 1.5% (preservative)<br>Rocima 550 (preservative)<br>Rocima 607 (preservative)<br>Rozone 2000 (dry film fungicide)<br>Skane M-8 (dry film fungicide) |
| Troy Corp.<br>Florham Park, NJ<br>Fax: 973.443.0843<br>E-mail: marketing@troycorp.com<br>www.troycorp.com | Polyphase 678<br>Polyphase 663<br>Polyphase CST<br>Polyphase 641<br>Troysan 680<br>Mergal K10N |

As would be known to one of ordinary skill in the art, determination of whether damage to a coating and/or film is due to microorganisms (e.g., film algal defacement, film fungal defacement), as well as the efficacy of addition of a preservative to a coating and/or film composition in reducing microbial damage to a coating and/or film, may be empirically determined by techniques such as those that are described in "ASTM Book of Standards, Volume 06.01, Paint—Tests for Chemical, Physical, and Optical Properties; Appearance," D3274-95, D4610-98, D2574-00, D3273-00, D3456-86, D5589-97, and D5590-00, 2002; and in "Paint and Coating Testing Manual, Fourteenth Edition of the Gardner-Sward Handbook," (Koleske, J. V. Ed.), pp. 654-661, 1995. Examples of microorganisms typically selected in such procedures as positive controls of a coating and/or film damaging microorganism include, for example, *Aspergillus oryzae* (ATCC 10196), *Aspergillus flavus* (ATCC 9643), *Aspergillus niger* (ATCC 9642), *Pseudomonas aeruginosa* (ATCC 10145), *Aureobasidium pullulans* (ATCC 9348), *Penicillium citrinum* (ATCC 9849), *Penicillium funiculosum* (ATCC 9644), or a combination thereof.

In general, a preservative, and use of a preservative in a coating, is known to those of skill in the art, and all such materials and techniques for using a preservative in a coating may be applied in the practice of the present invention (see, for example, Flick, E. W. "Handbook of Paint Raw Materials, Second Edition," 263-285 and 879-998, 1989; in "Paint and Coating Testing Manual, Fourteenth Edition of the Gardner-Sward Handbook," (Koleske, J. V. Ed.), pp 261-267 and 654-661, 1995; in "Paint and Surface Coatings, Theory and Practice, Second Edition," (Lambourne, R. and Strivens, T. A., Eds.), pp. 193-194, 371-382 and 543-547, 1999; Wicks, Jr., Z. W., Jones, F. N., Pappas, S. P. "Organic Coatings, Science and Technology, Volume 1: Film Formation, Components, and Appearance," pp. 318-320, 1992; Wicks, Jr., Z. W., Jones, F. N., Pappas, S. P. "Organic Coatings, Science and Technology, Volume 2: Applications, Properties and Performance," pp. 145, 309, 319-323 and 340-341, 1992; in "Paints, Coatings and Solvents, Second, Completely Revised Edition," (Stoye, D. and Freitag, W., Eds.) pp 6, 127 and 165, 1998; and in "Handbook of Coatings Additives", pp. 177-224, 1987).

It is contemplated that any previously described formulation of a fungal-prone composition may be modified to incorporate an antifungal peptidic agent. Examples of described coating compositions include over 200 industrial water-borne coating formulations (e.g., air dry coatings, air dry or force air dry coatings, anti-skid of non-slip coatings, bake dry coatings, clear coatings, coil coatings, concrete coatings, dipping enamels, lacquers, primers, protective coatings, spray enamels, traffic and airfield coatings) described in "Industrial water-based paint formulations," 1988, over 550 architectural water-borne coating formulations (e.g., exterior paints, exterior enamels, exterior coatings, interior paints, interior enamels, interior coatings, exterior/interior paints, exterior/interior enamels, exterior/interior primers, exterior/interior stains), described in "Water-based trade paint formulations," 1988, the over 400 solvent borne coating formulations (e.g., exterior paints, exterior enamels, exterior coatings, exterior sealers, exterior fillers, exterior primers, interior paints, interior enamels, interior coatings, interior primers, exterior/interior paints, exterior/interior enamels, exterior/interior coatings, exterior/interior varnishes) described in "Solvent-based paint formulations," 1977; and the over 1500 prepaint specialties and/or surface tolerant coatings (e.g., fillers, sealers, rust preventives, galvanizers, caulks, grouts, glazes, phosphatizers, corrosion inhibitors, neutralizers, graffiti removers, floor surfacers) described in Prepaint Specialties and Surface Tolerant Coatings, by Ernest W. Flick, Noyes Publications, 1991.

An exemplary exterior gloss alkyd house paint that comprises an antifungal peptidic agent is as follows in Table 5:

TABLE 5

| Component | Weight or Volume |
|---|---|
| Grind: | |
| first alkyd | 232.02 lb or 29.9 gallons |
| second alkyd | 154.2 lb or 20 gallons |
| aliphatic solvent: duodecane | 69.55 lb or 1.7 gallons |
| lecithin | 7.8 lb or 0.91 gallons |
| TiO$_2$ | 185.25 lb or 5.43 gallons |
| 10 micron silica | 59.59 lb or 2.7 gallons |
| bentonite clay | 18.00 lb or 1.44 gallons |
| second alkyd | 97.22 lb or 12.61 gallons |
| first alkyd | 69.84 lb or 9.00 gallons |
| antifungal peptidic agent - optionally, in combination with a conventional mildewcide | effective amount/up to 7.8 lb or 0.82 gallons |
| Letdown: | |
| aliphatic solvent: dudecane) | 19.50 lb or 3.00 gallons |
| first drier: 12% solution cobalt) | 2.00 lb or 0.23 gallons |
| second drier: 18% solution Zr) | 2.92 lb or 0.32 gallons |
| third drier: 10% solution Ca) | 8.00 lb or 0.98 gallons |
| Anti skinning agent: | |
| methyl ethyl ketoxime | 3.22 lb or 0.42 gallons |
| Aliphatic solvent | 9.75 lb or 1.50 gallons |

A preferred exterior flat latex house paint comprising an antifungal peptidic agent will contain the following components, listed in typical order of addition in Table 6:

TABLE 6

| Component | Weight or Volume |
|---|---|
| water | 244.5 lb or 29.47 gallons |
| hydroxyethylcellulose | 3 lb or 0.34 gallons |
| glycols | 60 lb or 6.72 gallons |
| polyacrylate dispersant | 6.8 lb or 0.69 gallons |
| Antifungal Peptidic Agent optionally, other biocide(s) | effective amount up to 10 lb or 1 gallons |
| non-ionic surfactant | 1 lb or 0.11 gallons |
| titanium dioxide | 225 lb or 6.75 gallons |
| silicate mineral | 160 lb or 7.38 gallons |
| calcined clay | 50 lb or 2.28 gallons |
| acrylic latex, @ 60% | 302.9 lb or 34.42 gallons |
| coalescent | 9.3 lb or 1.17 gallons |
| defoamers | 2 lb or 0.26 gallons |
| ammonium hydroxide | 2.2 lb or 0.29 gallons |
| 2.5% HEC solution | 76 lb or 9.12 gallons |
| antifungal peptidic agent | 1.8 lb or 0.82 gallons |

From these representative formulations, it will be readily appreciated that a wide variety of paints and other coating compositions may be improved by addition of an antifungal peptidic agent. Some of these include industrial water-borne coating formulations (e.g., air dry coatings, air dry or force air dry coatings, anti-skid of non-slip coatings, bake dry coatings, clear coatings, coil coatings, concrete coatings, dipping enamels, lacquers, primers, protective coatings, spray enamels, traffic and airfield coatings); architectural water-borne coating formulations (e.g., exterior paints, exterior enamels, exterior coatings, interior paints, interior enamels, interior coatings, exterior/interior paints, exterior/interior enamels, exterior/interior primers, and exterior/interior stains); solvent borne coating formulations (e.g., exterior paints, exterior enamels, exterior coatings, exterior sealers, exterior fillers, exterior primers, interior paints, interior enamels, interior coatings, interior primers, exterior/interior paints, exterior/interior enamels, exterior/interior coatings, and exterior/interior varnishes); and prepaint specialties and/or surface tolerant coatings (e.g., fillers, sealers, rust preventives, galvanizers, caulks, grouts, glazes, phosphatizers, corrosion inhibitors, neutralizers, graffiti removers and floor surfacers).

An antifungal paint or coating containing an antifungal peptidic agent may then be tested and used as described elsewhere herein, or the product may be employed for any other suitable purpose as would be recognized by one of skill in the art in light of this disclosure. For instance, the physical properties (e.g., purity, density, solubility, volume solids and/or specific gravity, rheology, viscometry, and particle size) of the resulting antifungal liquid paint or other coating product, can be assessed using standard techniques that are known in the art and/or as described in PAINT AND COATING TESTING MANUAL, 14$^{th}$ ed. of the Gardner-Sward Handbook, J. V. Koleske, Editor (1995), American Society for Testing and Materials (ASTM), Ann Arbor, Mich., and applicable published ASTM test methods. Alternatively, any other suitable testing method as would be known to one of ordinary skill in the art in light of the present disclosures, may be employed for assessing physical properties of the paint or coating mixture containing an above-described antifungal peptide additive.

Example 8

Inhibition of In-Can Mold Growth by Antifungal Peptides

As mentioned in the background discussion, the quality of a liquid coating mixture may suffer markedly if microorganisms degrade one or more of the components during storage. Since many of the coating products in use today contain ingredients that make it susceptible or prone to fungal infestation and growth, it is common practice to include a preservative. Although bacterial contamination may be a contributing factor, fungi are typically a primary cause of deterioration of a liquid paint or coating. Foul odor, discoloration, thinning and clumping of the product, and other signs of deterioration of components render the product commercially unattractive and/or unsatisfactory for the intended purpose. If the container will be opened and closed a number of times after its initial use, in some instances over a period of several months or years, it will inevitably be inoculated with ambient fungus organisms or spores subsequent to purchase by the consumer.

To avoid spoilage, it is especially desirable to ensure that the product will remain stable and usable for the foreseeable duration of storage and use by enhancing the long-term antifungal properties of the paint or coating with an antifungal peptide agent. The in-can stability and prospective shelf life of a paint or coating mixture containing an above-described antifungal peptide agent may be assessed using any appropriate testing method as would be known to one of skill in the art using conventional microbiological techniques. A fungus known to infect paints or other coatings is preferably employed as the test organism.

Example 9

Testing Protocols for Evaluating Antifungal Coatings

One suitable assay protocol for evaluating coatings containing an antifungal peptide is described by the American Society for Testing and Materials (ASTM) in D-5590-94 ("Standard Test Method for Determining the Resistance of Paint Films and Related Coatings to Fungal Defacement by Accelerated Four-Week Agar Plate Assay"), which is hereby incorporated herein by reference. The test method is modified as indicated below, and generally comprises:

(a) preparing a set of four 1×10 cm aluminum coupons approximately 1/32 in. thick are prepared as follows: (1) blank Al coupon; (2) Al coupon coated with an aqueous solution of a peptide produced and identified as described in the preceding examples, and allowed to dry; (3) Al coupon coated on both sides with a base paint composition, allowed to dry, and then the paint film is coated with a like amount of the same test peptide solution as applied to coupon 2; and (4) Al coupon painted with a paint mixture containing the same base paint composition as for coupon 3 and a like amount of the peptide, as for coupons 2 and 3. Preferably duplicate or triplicate sets of these specimens are prepared. Optionally, a conventional biocide may be included as a positive control. The base paint composition may be any suitable water-based latex paint, without biocides, which is available from a number of commercial suppliers.

(b) Each of the specimens from (a) is placed on a bed of nutrient agar and uniformly innoculated with a fungal suspension. A preferred test organism is *Fusarium oxysporum*. The fungal suspension may be applied by atomizer or by pipet, however a thin layer of nutrient agar mixed with the fungal innoculum is preferred.

(c) The specimens are incubated at about 28° C. under 85 to 90% relative humidity for 4 weeks.

(d) Fungal growth on each specimen is preferably rated weekly as follows: None=0; traces of growth (<10% coverage)=1; light growth (10-30%)=2; moderate growth (30-60%)=3; and heavy growth (60% to complete coverage)=4.

Another suitable assay protocol for testing the antifungal properties of a coating or paint film containing an antifungal peptide is described by the ASTM in D-5590-94 ("Standard Test Method for Resistance to Growth of Mold on the Surface of Interior Coatings in an Environmental Chamber"), which is hereby incorporated herein by reference. The testing protocol generally includes:

(a) Preparation of the Coated Surface. Duplicate or triplicate sets of approximately ½ in. thick, 3×4 in. untreated wooden or gypsum board panels are prepared as follows: (1) blank panel; (2) coated with an aqueous solution of a peptide produced and identified as described in the preceding examples, and allowed to dry; (3) coated on both sides with a base paint composition, allowed to dry, and then the paint film is coated with a like amount of the same test peptide solution as applied to panel 2; and (4) painted with a paint mixture containing the same base paint composition as for panel 3 and a like amount of the peptide, as for panels 2 and 3. Optionally, a conventional biocide may be included as a positive control.

(b) Contamination. The panels are randomly arranged and suspended in an environmental cabinet above moist soil that has been inoculated with the desired fungus, preferably *Fusarium oxysporum*. Enough free space is provided to allow free circulation of air and avoiding contact between the panels and the walls of the cabinet.

(c) Incubation. The panels are incubated for two weeks at 30.5-33.5° C. and 95-98% humidity.

(d) Scoring. A set of panels (test, control, and, optionally, a positive control) are removed for analysis at intervals, preferably weekly. The mold growth on the specimen panels is rated as described above.

Alternatively, one or more equivalent testing protocols may be employed, and field tests of coating compositions containing laboratory-identified antifungal peptides or candidate peptides may be carried out in accordance with conventional methods as would be known to those of skill in the art.

Example 10

Latex Paints with Antifungal Peptidic Agents

Both the interior latex (Olympic Premium, flat, ultra white, 72001) and acrylic paints (Sherwin Williams DTM, primer/finish, white, B66W1; 136-1500) appeared to be toxic to both *Fusarium* and *Aspergillus*. Therefore, eight individual wells (48-well microtito plate) of each paint type were extracted on a daily basis with 1 ml of phosphate buffer for 5 days (1-4 & 6) and then the plates were allowed to dry before running the assay. Each well contained 16 ul of respective paint.

Extract testing: The extract from two wells each of the two paints for each day was tested for toxicity by mixing the extract 1:1 with 2× medium and inoculating with spores (10E4) of *Aspergillus* or *Fusarium*. The extracts had no affect on growth of either test fungus.

Well testing: The extracted and non-extracted wells for each of the paints were tested with a range of inoculum levels in growth medium using the two different fungi. For *Fusarium* the range was 10E1-10E4 and for *Aspergillus* 10E2-10E5.

Well Testing of Acrylic Paint Plates: Both *Fusarium* and *Aspergillus* grew in all extracted wells at all inoculum levels. Only *Aspergillus* grew in non-extracted wells at the 10E5 level and not at lower levels indicative of an inherent biocidal capability.

Well Testing of Latex Paint Plates: *Fusarium* grew in the extracted wells only at the 10E4 inoculum level but not at 10E1-10E3. *Aspergillus* grew in all extracted wells showing an inoculum level effect. No growth was observed for either *Fusarium* or *Aspergillus* in non-extracted wells.

Conclusion: Extraction of the toxic factor(s) found in both paints was possible. However, it appeared that it may be less extractable from the latex paint.

Evaluation of peptide activity in presence of acrylic and latex paints: It was established that it was possible to extract both acrylic and latex paints dried in a 48-well format to make them non-toxic to the test microorganisms—*Fusarium* and *Aspergillus*. Using that information an experiment was designed to determine the effect the paint has on peptide activity against two test organisms.

Experimental design: (1.) Coat 48-well plastic plates with 16 μl of acrylic or latex paint. Dry for two days under hood. (2.) Extract designated wells with 1-ml phosphate buffer changing the buffer on a daily basis for 7 days. Control wells were not extracted to confirm paint toxicity. (3.) Add 20 μl of peptide series in duplicate to designated dry paint coated wells. Peptide, SEQ ID No. 41, series were added in a two-fold dilution series to wells and allowed to dry. The concentration of peptide added ranged from 200 μg/20 μl to 1.5 μg/20 μl.

Inoculated paint-coated plates as follows: (1.) Extracted control wells received 180 μl of medium+20 μl of spore suspension ($10^4$ spores/20 μl of medium). Inoculum was either *Fusarium* or *Aspergillus* in each case. (2.) Non-extracted control wells received 180 μl of medium+20 μl of spore suspension ($10^4$ spores/20 μl of medium). (3.) Extract wells with dried peptide series received 180 μl of medium+20 μl of spore suspension ($10^4$ spores/20 μl of medium). In duplicate. (4.) Extract wells that did not have dried peptide series received 160 μl of medium+20 μl of spore suspension ($10^4$/20 μl of medium)+20 μl peptide series as above. In duplicate. (5.) Plates were observed for growth over a 5-day period.

Growth and peptide controls: (1.) Use sterile non-paint coated 48 well plastic plates. (2.) Growth control wells for each test fungus received 180 μl of medium+20 μl of spore suspension ($10^4$ spores/20 μl of medium). (3.) Peptide activity controls received 160 μl of medium+20 μl of spore suspension ($10^4$ spores/20 μl of medium)+20 μl peptide series as above. Peptide series were added in a two-fold dilution series to wells and range from 200 μg/20 μl to 1.5 μg/20 μl. Therefore, the range of peptide tested was 200 μg/200 μl or 1.0 μg/μl (1000 μg/ml) to 0.0075 μg/μl (7.5 μg/ml). (4.) Uninoculated medium served as blank for absorbance readings taken at 24, 48, 72, 96 and 120 h.

Results:

Unextracted wells containing either latex or acrylic paint inhibited growth of both *Fusarium* and *Aspergillus*. Extracted wells containing either latex or acrylic paint allowed growth of both *Fusarium* and *Aspergillus*.

The calculated MIC for *Fusarium* in peptide activity control experiments was 15.62 μg/ml. For *Aspergillus* the calculated MIC was 61.4 μg/ml.

For extracted acrylic-coated plates the following results were obtained.

Controls as stated in above.

For *Fusarium* with dried peptide, inhibition was seen at 1000 and 500 g/ml after 5 days. Spores exposed to liquid peptide added to dry paint wells were inhibited at 1000, 500 and 250 μg/ml after 4 days, and 1000 and 500 μg/ml after 5 days.

For *Aspergillus* with dried peptide, inhibition was seen at 1000 μg/ml after 5 days. Spores exposed to liquid peptide added to dry paint wells were inhibited at 1000 and 500 g/ml after 5 days.

For extracted latex-coated plates the following results were obtained.

Controls as stated above.

For *Fusarium* with dried peptide, inhibition was seen at 1000 μg/ml after 5 days. Spores exposed to liquid peptide added to dry paint wells were inhibited at 1000 μg/ml after 5 days.

For *Aspergillus* with dried peptide, inhibition was seen at 1000 μg/ml after 5 days. Spores exposed to liquid peptide added to dry paint wells were inhibited at 1000 μg/ml after 5 days.

Example 11

Coating a Surface to Inhibit Fungus Infestation and Growth

When anchorage, food and moisture are available, fungus microorganisms are able to survive where temperatures permit. Particularly susceptible surfaces include porous materials such as stone, brick, wall board (Sheetrock®) and ceiling tiles; and semi-porous materials, including concrete, unglazed tile, stucco, grout, painted surfaces, roofing tiles, shingles, painted or treated wood and textiles. Any type of indoor or outdoor object, structure or material that is capable of providing anchorage, food and moisture to fungal cells is potentially vulnerable to infestation with mold, mildew or other fungus. Moisture generally appears due to condensation on surfaces that are at or below the dew point for a given relative humidity. To inhibit or prevent fungus infestation and growth, one or more antifungal peptidic agents from Example 1 or 3-6, preferably approximately 250-1000 mg/L of the hexapeptide of SEQ ID No. 41, is dissolved or suspended in water and applied by simply brushing or spraying the solution onto a pre-painted surface such as an exterior wall that is susceptible to mold infestation. Conventional techniques for applying or transferring a coating material to a surface are well known in the art and are suitable for applying the antifungal peptide composition. The selected peptides have activity for inhibiting or preventing the growth of one or more target fungi. The applied peptide solution is then dried on the painted surface, preferably by allowing it to dry under ambient conditions. If desired, drying can be facilitated with a stream of warm, dry air. Optionally, the application procedure may be repeated one or more times to increase the amount of antifungal peptide that is deposited per unit area of the surface. As a result of the treatment, when the treated surface is subsequently subjected to the target mold organisms or spores and growth promoting conditions comprising humidity above about typical indoor ambient humidity, presence of nutrients, and temperature above about typical indoor ambient temperature and not exceeding about 38° C., the ability of the surface to resistance fungal infestation and growth is enhanced compared to its pre-painted condition before application of the antifungal peptide.

A simple spray-coated surface may not provide sufficient durability for certain applications such as surfaces that are exposed to weathering. Longer-term protection may be provided against adhesion and growth of mold by mixing one or more of the antifungal peptides with a base paint or other coating composition, which may be any suitable, commercially available product as are well known in the art. Preferably the base composition is free of chemicals and other additives that are toxic to humans or animals, and/or that fail to comply with applicable environmental safety rules or guidelines. The typical components, additives and properties of conventional paints and coating materials, and film-forming techniques, are well known in the art and are also described in U.S. patent application Ser. No. 10/655,345 filed Sep. 4, 2003 and U.S. patent Ser. No. 10/792,516 filed Mar. 3, 2004, which is hereby incorporated herein by reference.

If additional, long-term protection against growth and adhesion of mold, mildew and fungus is desired, the paint or other coating composition may include a barrier material that resists moisture penetration and also prevents or deters penetration and adhesion of the microorganisms and the airborne contaminants which serve as food for the growing organisms. Some typical water repellent components are acrylic, siliconates, metal-stearates, silanes, siloxane and paraffinic waxes. The user will preferably take additional steps to deter mold infestation include avoiding moisture from water damage, excessive humidity, water leaks, condensation, water infiltration and flooding, and taking reasonable steps to avoid buildup of organic matter on the treated surface.

Example 12

Method of Treating a Fungus-Infested Surface

Although it is preferred that in situations where existing fungal growth is present, the mold colonies and spores are first removed or substantially eliminated before application of one of the present antifungal coatings, it is expected that in some situations an antifungal compositions will be applied to existing mold infected surfaces. In this case, the composition, containing one or more antifungal peptides, may inhibit, arrest the growth of, or substantially eradicate the mold. Early detection and treatment is highly preferred in order to minimize the associated discoloration or other deterioration of the underlying surface due to mold growth. The treatment procedure may consist of simply applying one or more coats of an antifungal peptide solution, paint or other coating composition as described above in Example 11.

Example 13

Method of Impregnating a Porous Substrate to Inhibit Fungus Growth

Porous or semi-porous objects or materials such as paper, fabrics, carpet, some types of stone, and many other items that are employed indoors or outdoors, have internal surface areas that can be susceptible to infestation by mold and are very difficult to treat effectively by conventional methods. It is within the scope of the present invention to impregnate such porous objects with a coating material containing one or more antifungal peptide, as described in one or more of the preceding examples. The liquidity of the composition is such that it is capable of penetrating into the pores of the object. In this way, an effective amount of the antifungal peptide is deposited on the internal surfaces as well as the exterior ones. Circumstances requiring treatment of a porous surface may benefit from using a relatively thin coating material rather than a thick, pigmented paint, in order to facilitate penetration of the pores.

Example 14

Coating a Fruit or Grain Storage Vessel to Inhibit Mold

The interior walls of grain silos or other fruit or grain storage or transportation tanks are coated with a peptidic antifungal composition of Example 12 or 13 to deter the attachment and growth of mold organisms inside the container. By selecting antifungal peptides that target specific organisms, and are non-toxic to humans or animals, mold contamination of a wide variety of agricultural products may be deterred.

Example 15

Use of Antifungal/Anti-Bacterial Peptides

Over the past decade, outbreaks of food poisoning and hospital-acquired infections by so-called "super bugs" have become increasingly frequent. These are strains of bacteria that are resistant to conventional antibiotics, such as Methicillin-resistant *Staphylococcus aureus* (MRSA) and Vero-cytotoxin producing variants of *Escherichia coli*. Worldwide public concern about hygienic surfaces have also been heightened today due to the emergence and spread of new viral infections such as SARS. The current proliferation of antimicrobial cleaners, utensils, food preparation surfaces and coating systems aimed at fulfilling the demands of an increasingly hygiene conscious public are a testament to those widespread concerns.

Some of the antifungal peptides, particularly the 8-10 amino acid residue long peptides also have the property of inhibiting the growth of bacteria, including disease-causing bacteria such as *Staphalococcus* and *Streptococcus*. Thus, it is known that peptides such as 41, 197, 198, and 199, can inhibit growth of *E. amylovora, E. carotovora, E. coli, R. solanocerum, S. aureus*, and *S. faecalis* in standard media at IC50's of between 10-1100 mg/ml and MIC's of between 20-1700 mg/ml. *Staphylococcus* and *Streptococcus* bacteria are of special concern in hospital environments where antibiotic resistance is increasingly common. A multipurpose paint or coating is prepared by combining one or more antifungal peptide selected as described in any of Examples 1-6 with one or more antibacterial peptide. One such combination is the peptide of SEQ ID No. 41 and the peptide of SEQ ID No. 41. Alternatively a peptide is selected with both antifungal and antibacterial peptides 6-10. Paints and other coatings containing the antifungal/antibacterial peptides will be applied to surfaces to lend antifungal and anti-bacterial properties to those surfaces. It is expected that the use of these and other antifungal/antibacterial peptidic agents will avoid the problem human toxicity that is associated with conventional biocidal compounds in today's paints and coatings. The advantage of combined antifungal and antibacterial activity will find particular usefulness in hospital environments and other health care settings.

Example 16

Combined Use of Antifungal Peptides and Other Antimicrobials

A paint composition containing one or more conventional antifungal substances may be modified by addition of one or more of the antifungal peptides described herein. As described in preceding examples, the antifungal peptidic agent may be a single peptide of precisely known sequence, preferably the hexapeptide of SEQ ID No. 198 or an antifungal/antibacterial peptide as described in Example 15. Alternatively, the peptidic agent may be a peptide library aliquot containing a mixture of peptides in which at least two (and preferably three or four) of the N-terminal amino acid residues are known. If the peptidic agent is a mixture of peptides, one or more peptides will have antifungal activity.

Combining a non-peptidic antifungal agent with one or more antifungal peptides may provide antifungal activity over and above that seen with either the peptide(s) or the non-peptidic agent alone. The expected additive inhibitory activity of the combination is calculated by summing the inhibition levels of each component alone. The combination is then tested on the test organism to derive an observed additive inhibition. If the observed additive inhibition is greater than that of the expected additive inhibition, synergy is exhibited. More specifically, a synergistic combination of an antifungal peptide, or an aliquot of a peptide library containing at least one antifungal peptide, occurs when two or more fungal cell growth-inhibitory substances distinct from the peptide or peptide library aliquot are observed to be more inhibitory to the growth of a test organism than the sum of the inhibitory activities of the individual components alone.

A testing method for determining additive or synergistic combinations comprises first creating a synthetic peptide combinatorial library. Each aliquot of the library represents an equimolar mixture of peptides in which at least the two C-terminal amino acid residues are known. Using the testing methods described in one or more of U.S. Pat. No. 6,020,312, U.S. Pat. No. 5,885,782, and U.S. Pat. No. 5,602,097 it is possible to determine for each such aliquot of the synthetic peptide combinatorial library, a precisely calculated concentration at which it will inhibit a test fungus in a coating. Next, the aliquot of the synthetic peptide combinatorial library is mixed with at least one non-peptide antifungal compound to create a test mixture. As with the peptide component of the mixture, the baseline ability of the non-peptide antifungal substance to inhibit the test fungus is determined initially. Next, the test fungus is contacted with the test mixture, and the inhibition of growth of the test organism is measured as compared to at least one untreated control. More controls are desirable, such as a control for each individual component of the mixture. Similarly, where there are more than two components being tested, the number of controls to be used must be increased in a manner well known to those of skill in the art of growth inhibition testing. From the separate test results for the peptidic and non-peptidic agents the expected additive effect on inhibition of growth is determined using standard techniques. After the growth inhibition tests are complete for the combination of peptidic and non-peptidic agents, the actual or observed effect on the inhibition of growth is determined. The expected additive effect and the observed effect are then compared to determine whether a synergistic inhibition of growth of the test fungus has occurred. The methods used to detect synergy may utilize non-peptide antimicrobial agents in combination with the inhibitory peptides described above.

As described above, an antifungal peptidic agent may be used in combination with one or more existing fungicides and/or fungistatics identified herein or as would be known to one of ordinary skill in the art. It is expected that some combinations of an antifungal peptidic agent with another fungicide and/or fungistatic may provide advantages such as a broader range of activity against various organisms, a synergistic antifungal or preservative effect, or a longer duration of effect.

Another potentially advantageous combination includes an antifungal peptidic agent and a preservative that acts against non-fungal organisms (e.g., a bactericide, an algaecide), as it is contemplated that many fungal prone compositions and surfaces coated with such compositions are also susceptible to damage by a variety of organisms. Examples of preservatives that an antifungal peptidic agent may substitute for and/or be combined include, but are not limited to those non-peptidic antimicrobial compounds (i.e., biocides, fungicides, algaecides and mildewcides) have been shown to be of utility and are currently available and approved for use in the U.S./NAFTA, Europe, and the Asia Pacific region. These antimicrobial agents are listed in Table 4, together with the name of a supplier.

Certain peptides contemplated for use as described herein have been shown (in one or more of U.S. Pat. Nos. 6,020,312; 5,602,097; and 5,885,782) to involve synergy between antifungal peptides and non-peptide antifungal agents that is useful in controlling growth of the *Fusarium, Rhizoctonia, Ceratocystis, Pythium, Mycosphaerella, Aspergillus* and *Candida* genera of fungi. In particular, synergistic combinations have been described and successfully used to inhibit the growth of *Aspergillus fumigatus* and *A. paraciticus*, and also *Fusarium oxysporum* with respect to agricultural applications. It is expected that these and other synergistic combinations of peptide and non-peptide agents will be useful as additives in paints, coatings and other compositions for deterring, preventing, or treating a fungal infestations.

Example 17

Combined Use of Antifungal Peptides and OP Degrading Agents

Beyond the concerns about food poisoning and hospital acquired infections by antibiotic-resistant "super bugs," and worries about SARS-like outbreaks, there is also a need to prevent or protect against the possibility of contamination of public facilities and surfaces by toxic chemicals due to accidental spills, improper application of certain insecticides, or as a result of deliberate criminal or terroristic acts. In particular, organophosphorus compounds ("organophosphate compounds" or "OP compounds") and organosulfur ("OS") compounds, which are used extensively as insecticides, are highly toxic to many organisms, including humans. OP compounds function as nerve agents, and some of the most toxic OP compounds are known to have been used as chemical warfare agents. As discussed in more detail in copending U.S. patent application Ser. No. 10/655,345 filed Sep. 4, 2003, some OP chemical warfare agents can be taken up through skin contact and can remain on material, equipment and terrain for long periods of time (e.g., weeks). By addition of a thickener (e.g., a variety of carbon polymers), even volatile OP agents may be rendered less volatile and more persistent on a contaminated surface.

Thus, it can be readily appreciated that in some situations a multifunctional surface treatment that combines antifungal properties with the ability to degrade organophosphorus compounds would be desirable. Such composition may be in the form of a coating, a paint, a non-film forming coating, an elastomer, an adhesive, an sealant, a material applied to a textile, or a wax, and may be modified by addition of one or more antifungal peptide selected as described in Examples 1-6 and an organophosphorus compound detoxifying agent such as an OP degrading enzyme or cellular material containing such activity. Suitable OP degrading agents are described in copending U.S. patent application Ser. No. 10/655,345 filed Sep. 4, 2003 and U.S. patent application Ser. No. 10/792,516 filed Mar. 3, 2004 and hereby incorporated herein by reference.

Example 18

Adhesives, Sealants and Elastomers Containing Antifungal Peptides

The antifungal additives described above are expected to be additionally useful for coating or mixing into sealants and elastomers such as grouts and caulks, especially those that are in frequent contact with, or constantly exposed to fungal nutrients and/or moisture. Examples of adhesives and sealants (e.g., caulks, acrylics, elastomers, phenolic resin, epoxy, polyurethane, anaerobic and structural acrylic, high-temperature polymers, water-based industrial type adhesives, water-based paper and packaging adhesives, water-based coatings, hot melt adhesives, hot melt coatings for paper and plastic, epoxy adhesives, plastisol compounds, construction adhesives, flocking adhesives, industrial adhesives, general purpose adhesives, pressure sensitive adhesives, sealants, mastics, urethanes) for various surfaces (e.g., metal, plastic, textile, paper), and techniques of preparation and assays for properties, have been described in Skeist, I., ed., Handbook of Adhesives, 3rd Ed., Van Nostrand Reinhold, New York, 1990; Satriana, M. J. Hot Melt Adhesives Manufacture and Applications, Noyes Data Corporation, New Jersey, 1974; Petrie, E. M., Handbook of Adhesives and Sealants, McGraw-Hill, New York, 2000; Hartshorn, S. R., ed., Structural Adhesives-Chemistry and Technology. Plenum Press, New York, 1986; Flick, E. W., Adhesive and Sealant Compound Formulations, 2nd Ed., Noyes Publications, New Jersey, 1984; Flick, E., Handbook of Raw Adhesives 2nd Ed., Noyes Publications, New Jersey, 1989; Flick, E., Handbook of Raw Adhesives, Noyes Publications, New Jersey, 1982; Dunning, H. R., Pressure Sensitive Adhesives—Formulations and Technology, 2nd Ed., Noyes Data Corporation, New Jersey, 1977; and Flick, E. W., Construction and Structural Adhesives and Sealants, Noyes Publications, New Jersey, 1988. An adhesive, sealant or elastomer composition containing one or more conventional antifungal substance may be modified by addition of one or more of the antifungal peptides described in Examples 1-6. The antifungal peptidic agent may be a single peptide of precisely known sequence, preferably the hexapeptide of SEQ ID No. 41 or an antifungal/antibacterial peptide as described in Example 14. Alternatively, the peptidic agent may be a peptide library aliquot containing a mixture of peptides in which at least two (and preferably three or four) of the N-terminal amino acid residues are known. If the peptidic agent is a mixture of peptides, at least one peptide will have antifungal activity.

Example 19

Antifungal Textile Finish

An antifungal peptidic agent may also be incorporated into a material applied to a textile, such as, for example, a textile finish. Textile finishes (e.g., soil-resistant finishes, stain-resistant finishes) and related materials for application to a textile are described, for example, in Johnson, K., ANTISTATIC COMPOSITIONS FOR TEXTILES AND PLASTICS, Noyes Data Corporation, New Jersey, 1976; Rouette, H. K., ENCYCLOPEDIA OF TEXTILE FINISHING, Springer, Verlag, 2001; TEXTILE FINISHING CHEMICALS: AN INDUSTRIAL GUIDE, by Ernest W. Flick, Noyes Publications, 1990; and HANDBOOK OF FIBER FINISH TECHNOLOGY, by Philip E. Slade, Marcel Dekker, 1998. One type of water repellent and/or oil repellent textile finish is Scotchguard™ (3M Corporate Headquarters, Maplewood, Minn., U.S.A.). A textile finish may be modified by addition of one or more of the antifungal peptides described in Examples 1-6. The antifungal peptidic agent may be a single peptide of precisely known sequence, preferably the hexapeptide of SEQ ID No. 41 or an antifungal/antibacterial peptide as described in Example 15. Alternatively, the peptidic agent may be a peptide library aliquot containing a mixture of peptides in which at least two (and preferably three or four) of the N-terminal amino acid residues are known. If the peptidic agent is a mixture of peptides, at least one peptide will have antifungal activity.

Example 20

Polymer-Linked Antifungal Peptides

In Example 4, above, conjugation of a peptide to a polymer carrier molecule or insoluble substrate is described for stabilizing the antifungal activity in the paint film or coating. That capability may also be used to advantage by chemically linking or otherwise associating one or more antifungal peptides to a polymeric material or plastic fabric which would otherwise be more susceptible to infestation, defacement or deterioration by fungus. Conventional techniques for linking the N- or C-terminus of a peptide to a long-chain polymer may be employed. The antifungal peptide may include additional amino acids on the linking end to facilitate linkage to the PVC polymer. A PVC-membrane such as a flexible or retractable roof or covering for an outdoor stadium is treated to chemically link antifungal peptides to at least a portion of the outer surface of the membrane prior to its installation. Where an installed polymer membrane covering is already infested by mold, and it is not practical for it to be removed and replaced by an antifungal peptide-linked polymer membrane, it may be feasible to clean the existing infestation or discoloration, and then apply or bond a suitable antifungal coating containing a stabilized antifungal peptide. PVC is only one of many well-known types of plastic or polymer-containing materials that could be linked to an antifungal peptide in this manner.

Example 21

Kit for Preparing an Antifungal Coating

For ease of production, in most instances an antifungal paint or coating product containing antifungal peptidic agents will be provided to the consumer as a single premixed formulation. Alternatively, in order to optimize the initial activity and extend the useful lifetime of the antifungal coating, the antifungal peptidic agent may instead be packaged separately from the paint or coating product into which the antifungal agent is to be added. For increased stability, the peptidic agent may also contain a suitable solid or liquid carrier. As in preceding examples, the antifungal peptidic agent may comprise one or more "pure" antifungal peptides of defined sequence, or it may include a peptide library aliquot containing a mixture of peptides in which at least two (and preferably three or four) of the N-terminal amino acid residues are known (as in SEQ ID Nos. 1-24). If the peptidic agent is a mixture of peptides, at least one will have antifungal activity.

In some situations it may also be preferred to store a fungal-prone material in a separate container ("pot") prior to application, in order to minimize the occurrence of fungal contamination prior to use and for other reasons. Separation of conventional coating components is typically done to reduce film formation during storage for certain types of coatings. Accordingly, some or all of the different components of the antifungal composition are stored in a plurality of containers, or as a multi-pack kit, and the components are admixed prior to and/or during application. For example, 0.001% to 100%, including all intermediate ranges and combinations thereof, of the antifungal peptidic agent may be stored in a separate container from one or more fungal-prone materials of the final composition. A multi-pack kit may include one or more pots of a fungal-prone material, preferably including 2- to 5-packs of fungal-prone material. A new antifungal composition may be prepared at or near the time of use by combining a fungal-prone material (e.g., carbon polymer-containing binder) with other coating components, including an antifungal peptide, polypeptide or protein, as described herein.

DEFINITIONS

The terms used herein have their customary and usual meanings, and are intended to encompass at least the following definitions, consistent with their use elsewhere herein:

As used herein other than the claims, the terms "a", "an", "the" and "said" means "at least one" or "one or more."

As used herein in the claim(s), when used in conjunction with the words "comprises" or "comprising," the words "a", "an", "the" or "said" may refer to one or more than one. As used herein "another" may mean at least a second or more.

"Fungus" includes multicellular and unicellular organisms in the fungus family, including the true fungi, molds, mildews and yeasts. "Mold" is sometimes used herein as a synonym for fungi, where the context permits, especially when referring to indoor contaminants. However, the term "mold" also, and more specifically, denotes certain types of fungi. For example, the plasmodial slime molds, the cellular slime molds, water molds, and the everyday common mold. True molds are filamentous fungi consisting of the mycelium, specialized, spore-bearing structures called conidiophores, and conidia (spores). "Mildew" is another common name for certain fungi, including the powdery mildews and the downy mildews. "Yeasts" are unicellular members of the fungus family. For the purposes of the present disclosure, where any of the terms fungus, mold, mildew and yeast is used, the others are implied where the context permits.

"Building materials" include, but are not limited to, conventional and non-conventional indoor and outdoor construction and decorative materials, such as wood, Sheetrock® (wallboard), paper or vinyl coated wallboard, fabrics (textiles), carpet, leather, ceiling tiles, cellulose resin wall board (fiberboard), stone, brick, concrete, unglazed tile, stucco, grout, painted surfaces, roofing tiles, shingles, and other materials that are cellulose-rich, or are capable of providing nutrients to fungi, or are capable of harboring nutrient materials and supporting fungal infestation.

"Bioactive" means having an effect on a living organism, especially fungal cells, when the context allows.

An "antifungal peptide" refers specifically to a contiguous amino acid sequence from 3 to 100 amino acid residues in length, including all intermediate ranges, and which is capable of exerting antifungal activity, as defined above. For simplicity, where the context permits, the term "antifungal peptide" also refers to antifungal polypeptides (i.e., a contiguous amino acid sequence from 101 to 10,000 amino acid residues in length, including all intermediate ranges, and antifungal proteins which are proteinaceous molecules having a contiguous amino acid sequence of more than 10,000 amino acid residues length. Preferably such peptides, polypeptides and proteins are not encoded by the genome of an organism.

"Antifungal peptidic agent" refers to a peptide, polypeptide or protein having the ability to inhibit the growth of one or more genera and/or species of fungi. It is also intended to encompass mixtures of such peptides, polypeptides and proteins, together with any associated stabilizers, carriers, and inactive peptides/polypeptides/proteins. Where the context allows, the term "antifungal peptidic agent" may also refer to a peptide library aliquot containing a mixture of peptides in which at least two of the N-terminal amino acid residues are known. If the peptidic agent is a mixture of peptides, at least one will have antifungal activity.

"Antifungal activity" refers to inhibition of fungal cell attachment and/or growth, and is may also refer to fungal cell killing, as the context permits. Accordingly, some antifungal peptidic agents can also be denoted as "fungistatic agents" or "fungicides."

"Inhibition of fungal growth" refers to cessation or reduction of fungal cell proliferation, and can also include inhibition of expression of cellularly produced proteins in static fungal cell colonies. Such inhibition can provide or facilitate disinfection, decontamination or sanitization of inanimate objects, which refer to the process of reducing the number of fungus microorganisms to levels that no longer pose a threat (e.g., to property or human health). Use of a bioactive antifungal agent can be accompanied by manual removal of mold-contaminated building materials, in some instances.

The term "biocide" as used herein refers to a substance that kills microorganisms and their spores. Depending on the type of microorganism killed, a biocidal substance may be further defined as a bactericide, fungicide, or algaecide. The term "biostatic" refers to a substance that prevents the growth of the microorganism and its spores, and encompasses bacteristatic, fungistatic and algaestatic compounds.

A "fungicide" is a biocidal substance used to kill or inactivate a specific microbial group, the fungi. The term "fungistatic," is used to denote substances that prevent fungal microorganisms from growing or reproducing, but do not result in substantial inactivation or killing.

An "effective amount" refers to a concentration of antifungal peptide that is capable of exerting the desired antifungal effect, as defined above.

An "inanimate object" refers to structures and objects other than living organisms. Examples of inanimate objects are architectural structures having painted or unpainted surfaces such as the exterior and interior walls of buildings, industrial equipment, outdoor sculptures and furniture, construction materials for indoor or outdoor use, such as wood, stone, brick, wall board (Sheetrock®), ceiling tiles, concrete, unglazed tile, stucco, grout, roofing tiles, shingles, painted or treated wood, synthetic composite materials, leather and textiles.

A "base" or "substrate" refers to any surface that can potentially support the infestation and/or growth of a fungus or spore under favorable conditions for such infestation or growth. It is intended to include exterior surfaces of objects as well as interior surfaces of porous and semiporous objects (e.g., high surface area porous stone structures), constitutes a surface on which a coating can be directly applied and/or impregnated.

The term "coating" has its usual meaning and specifically includes the process of applying (e.g., brushing, dipping, spreading, spraying) or otherwise producing a coated surface, which may also be referred to as a coating, coat, covering, film or layer on a surface.

Where the context so indicates, the term "coating" may instead refer to the coating composition or mixture that is applied. For example, a coating composition may be capable of undergoing a change from a fluent to a nonfluent condition by removal of solvents, vehicles or carriers, by setting, by chemical reaction or conversion, or by solidification from a molten state. The coating or film that is formed may be hard or soft, elastic or inelastic, permanent or transitory. Where the context allows, the act of coating also includes impregnating a surface or object by causing a coating material to extend or penetrate into the object, or into the interstices of a porous, cellular or foraminous material. The general composition and properties of conventional coating materials are described in U.S. patent application Ser. No. 10/655,345 filed Sep. 4, 2003, which is hereby incorporated herein by reference. Additionally, the use of the term "coating" ("coat," "surface coat," "surface coating") is also intended to be consistent with its use in PAINT and Coating Testing Manual, Fourteenth Edition of the Gardner-Sward Handbook (Koleske, J. V. Ed.), p. 696, 1995; and in "ASTM Book of Standards, Volume 06.01, Paint—Tests for Chemical, Physical, and Optical Properties; Appearance," D16-00, 2002, i.e., "a liquid, liquefiable or mastic composition that is converted to a solid protective, decorative, or functional adherent film after application as a thin layer." Examples of a coating include a clear coating and a paint.

A "paint" generally refers to a "pigmented liquid, liquefiable or mastic composition designed for application to a substrate in a thin layer which is converted to an opaque solid film after application. Used for protection, decoration or identification, or to serve some functional purpose such as the filling or concealing of surface irregularities, the modification of light and heat radiation characteristics, etc," [Paint and Coating Testing Manual, Fourteenth Edition of the Gardner-Sward Handbook (Koleske, J. V. Ed.), p. 696, 1995]. Surface treatments, particularly coatings and paints, have been described in U.S. patent application Ser. No. 10/655,345 filed Sep. 4, 2003.

"Elastomers" or rubbers are polymers that can undergo large, but reversible, deformations upon a relatively low physical stress. Elastomers (e.g., tire rubbers, polyurethane elastomers, polymers ending in an anionic diene, segmented polyerethane-urea copolymers, diene triblock polymers with styrene-alpha-methylstyrene copolymer end blocks, poly (p-methylstyrene-b-p-methylstyrene), polydimethylsiloxane-vinyl monomer block polymers, chemically modified natural rubber, polymers from hydrogenated polydienes, polyacrylic elastomers, polybutadienes, trans-polyisoprene, polyisobutene, cis-1,4-polybutadiene, polyolefin thermoplastic elastomers, block polymers, polyester thermoplastic elastomer, thermoplastic polyurethane elastomers) and techniques of elastomer synthesis and elastomer property analysis have been described, for example, in Walker, B. M., ed., Handbook of Thermoplastic Elastomers, Van Nostrand Reinhold Co., New York, 1979; Holden, G., ed., et. al., Thermoplastic Elastomers, 2nd Ed., Hanser Publishers, Verlag, 1996.

An "adhesive" is a composition that is capable of uniting, bonding or holding at least two surfaces together, preferably in a strong and permanent manner (e.g., glue, cement, paste).

A "sealant" is a composition capable of attaching to at least two surfaces, filling the space between them to provide a barrier or protective coating (e.g., by filling gaps or making a surface nonporous).

A "fungal-prone material" is a substance that is capable of serving as a food source for a fungus, or is a material that contains one or more such substance. For example, in the context of a paint or coating composition, a fungal-prone material may be a binder containing a carbon-based polymer that serves as a nutrient for a fungus.

All patents, published patent applications and other publications cited herein are hereby incorporated herein by reference to the extent that they describe materials and methods supplementary to that set forth herein. One skilled in the art will readily appreciate that the present invention is well adapted to carry out any objects and obtain the ends and advantages mentioned as well as those inherent therein. The preferred antifungal compositions and methods described herein are exemplary and intended to be representative of other embodiments which will be apparent to those skilled in the art in light of the present disclosure. For instance, in light of the present disclosure and representative examples, changes in the disclosed compositions and methods and other uses will occur to those skilled in the respective arts of preparing and using paints and coatings, textile finishes, waxes, elastomers, adhesives and sealants which are encompassed within the spirit of the invention and defined by the scope of the appended claims. The present examples, therefore, are not to be considered as limiting the scope of the present invention.

What is claimed:

1. A coating composition comprising:

the antifungal peptidic agent SEQ ID NO: 184 or a variant of SEQ ID NO: 184 having one or more functionally equivalent amino acids substituted therein, said substituted amino acids having no more than a +/−2 difference in hydropathic value of the Kyte-Doolittle scale compared to the hydropathic value of the Kyte-Doolittle scale of amino acids in SEQ ID NO: 184, wherein chiral amino acids of the peptidic agent are L-amino acids, and wherein said coating is a paint.

2. A coating composition comprising:

the antifungal peptidic agent SEQ ID NO: 184 or a variant of SEQ ID NO: 184 having one or more functionally equivalent amino acids substituted therein, said substituted amino acids having no more than a +/−2 difference in hydropathic value of the Kyte-Doolittle scale compared to the hydropathic value of the Kyte-Doolittle scale of amino acids in SEQ ID NO: 184, wherein said coating is a paint, said paint comprising at least one component selected from the group consisting of titanium dioxide, Bentonite clay, silicate mineral, and acrylic latex.

* * * * *